United States Patent
Corgie et al.

(10) Patent No.: US 9,597,672 B2
(45) Date of Patent: Mar. 21, 2017

(54) MESOPOROUS CATALYSTS OF MAGNETIC NANOPARTICLES AND FREE-RADICAL-PRODUCING ENZYMES, AND METHODS OF USE

(75) Inventors: Stephane C. Corgie, Ithaca, NY (US); Patarawan Kahawong, Nakhonsithammarat (TH); Emmanuel P. Giannelis, Ithaca, NY (US); Larry P. Walker, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 450 days.

(21) Appl. No.: 14/004,311

(22) PCT Filed: Mar. 9, 2012

(86) PCT No.: PCT/US2012/028392
§ 371 (c)(1),
(2), (4) Date: Sep. 10, 2013

(87) PCT Pub. No.: WO2012/122437
PCT Pub. Date: Sep. 13, 2012

(65) Prior Publication Data
US 2014/0004583 A1    Jan. 2, 2014

Related U.S. Application Data

(60) Provisional application No. 61/568,966, filed on Dec. 9, 2011, provisional application No. 61/451,360, filed on Mar. 10, 2011.

(51) Int. Cl.
| | | |
|---|---|---|
| B01J 31/00 | (2006.01) | |
| B82Y 30/00 | (2011.01) | |
| C12N 9/02 | (2006.01) | |
| C12N 11/14 | (2006.01) | |
| C02F 3/34 | (2006.01) | |

(52) U.S. Cl.
CPC ............ *B01J 31/003* (2013.01); *B82Y 30/00* (2013.01); *C02F 3/342* (2013.01); *C12N 9/0004* (2013.01); *C12N 11/14* (2013.01); *C02F 2305/08* (2013.01); *C12P 2201/00* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,152,210 A | 5/1979 | Robinson et al. |
| 6,440,711 B1 | 8/2002 | Dave et al. |
| 6,447,811 B1 | 9/2002 | Ravensberg et al. |
| 7,241,883 B2 | 7/2007 | Lugade et al. |
| 7,385,053 B2 | 6/2008 | Lugade et al. |
| 7,459,145 B2 | 12/2008 | Bao et al. |
| 7,485,367 B2 | 2/2009 | Chen et al. |
| 8,075,793 B2 | 12/2011 | Moreira et al. |
| 8,188,269 B1 | 5/2012 | Lugade et al. |
| 8,841,105 B2 | 9/2014 | Sakai et al. |
| 8,940,179 B2 | 1/2015 | Suh et al. |
| 9,035,003 B2 | 5/2015 | Hanson et al. |
| 2004/0039201 A1 | 2/2004 | Lugade et al. |
| 2006/0165910 A1 | 7/2006 | Kodas et al. |
| 2006/0286379 A1 | 12/2006 | Gao et al. |
| 2006/0289354 A1 | 12/2006 | Zhou et al. |
| 2008/0103061 A1 | 5/2008 | Lugade et al. |
| 2008/0287288 A1 | 11/2008 | Ying et al. |
| 2008/0305048 A1 | 12/2008 | Josephson et al. |
| 2009/0214885 A1 | 8/2009 | Her et al. |
| 2010/0056816 A1 | 3/2010 | Wallin et al. |
| 2010/0285376 A1 | 11/2010 | Hsueh et al. |
| 2012/0123026 A1 | 5/2012 | Lugade et al. |
| 2013/0196407 A1 | 8/2013 | Sheldon et al. |
| 2014/0004583 A1 | 1/2014 | Corgie et al. |
| 2014/0377789 A1 | 12/2014 | Moerman |
| 2015/0056145 A1 | 2/2015 | Chae et al. |
| 2015/0252352 A1* | 9/2015 | Corgie .................... A62D 3/02 210/606 |

FOREIGN PATENT DOCUMENTS

| | | |
|---|---|---|
| CN | 102329008 A | 1/2012 |
| CN | 102329008 B | 1/2013 |

(Continued)

OTHER PUBLICATIONS

Kim et al.,"A Magnetically Separable, Highly Stable Enzyme System Based on Nanocomposites of Enzymes and Magnetic Nanoparticles Shipped in Hierarchically Ordered Mesocellular, Mesoporous Silica", Small vol. 1 No. 12 pp. 1204-1207 (2005).*

Ahmad et al. Physico-Chemical Processes. Water Environment Research, vol. 77, No. 6, Literature Reviews [CD-ROM content], pp. 982-1156 (2005).

Adams et al. Specificity of Glucose Oxidase. Archives of Biochemistry and Biophysics 91 (1960) 230-234.

Ansari et al. Potential applications of enzymes immobilized on/in nano materials: A review. Biotechnology Advances 30 (2012) 512-523.

(Continued)

*Primary Examiner* — Anand Desai
(74) *Attorney, Agent, or Firm* — Scully Scott Murphy & Presser

(57) ABSTRACT

A composition comprising mesoporous aggregates of magnetic nanoparticles and free-radical producing enzyme (i.e., enzyme-bound mesoporous aggregates), wherein the mesoporous aggregates of magnetic nanoparticles have mesopores in which the free-radical-producing enzyme is embedded. Methods for synthesizing the enzyme-bound mesoporous aggregates are also described. Processes that use said enzyme-bound mesoporous aggregates for depolymerizing lignin, removing aromatic contaminants from water, and polymerizing monomers polymerizable by a free-radical reaction are also described.

19 Claims, 44 Drawing Sheets

(56) References Cited

FOREIGN PATENT DOCUMENTS

| EP | 1028628 B1 | 2/2003 |
|---|---|---|
| EP | 2110175 A1 | 10/2009 |
| EP | 2593544 A2 | 5/2013 |
| EP | 1476753 B1 | 8/2013 |
| JP | 2005532533 A | 10/2005 |
| JP | 4598403 B2 | 12/2010 |
| WO | WO9922597 A1 | 5/1999 |
| WO | WO03080796 A2 | 10/2003 |
| WO | WO2006004557 A1 | 1/2006 |
| WO | WO2009115335 A1 | 9/2009 |
| WO | 2012/122437 A2 | 9/2012 |
| WO | WO2012122437 A2 | 9/2012 |
| WO | WO2012122437 A3 | 9/2012 |
| WO | WO2013109057 A1 | 7/2013 |
| WO | WO2014055853 A1 | 4/2014 |
| WO | WO2015078241 A1 | 6/2015 |
| WO | WO2015111030 A2 | 7/2015 |
| WO | WO2015113047 A2 | 7/2015 |
| WO | WO2015145222 A2 | 10/2015 |
| WO | WO2015157530 A2 | 10/2015 |

OTHER PUBLICATIONS

Anthon et al. Colorimetric Method for the Determination of Lipoxygenase Activity. J. Agric. Food Chem. 49 (2001) 32-37.

Banerjee et al. A High-Throughput Amenable Colorimetric Assay for Enantioselective Screening of Nitrilase-Producing Microorganisms Using pH Sensitive Indicators. Journal of Biomolecular Screening 8(5); 2003, pp. 559-565.

Baskar et al. Magnetic immobilization and characterization of beta-amylase as nanobiocatalyst for hydrolysis of sweet potato starch. Biochemical Engineering Journal 102 (2015) 18-23.

Cassimjee. ω-Transaminase in Biocatalysis Methods. Reactions and Engineering. Doctoral Thesis KTH Royal Institute of Technology, School of Biotechnology Stockholm (2012).

Dong et al. Efficient biosynthesis of uridine diphosphate glucose from maltodextrin by multiple enzymes immobilized on magnetic nanoparticles. Carbohydrate Research 345, (2010)1622-1626.

Errede et al. Oxidation of ferrocytochrome c by mitochondrial cytochrome c oxidase. Proc. Nat. Acad. Sci. USA, vol. 73, No. 1, pp. 113-117, Jan. 1976.

Gebreyohannes et al. Nanoscale tuning of enzyme localization for enhanced reactor performance in a novel magnetic-responsive biocatalytic membrane reactor. Journal of Membrane Science 487(2015) 209-220.

Illanes et al. Recent trends in biocatalysis engineering. Bioresource Technology 115 (2012) 48-57.

Karn et al. Nanotechnology and in Situ Remediation: A Review of the Benefits and Potential Risks. Environmental Health Perspectives, vol. 117, No. 12 (Dec. 2009), pp. 1823-1831.

Khan et al. Hazardous Waste Treatment Technologies. Water Environment Research, vol. 79, No. 10, Literature Reviews [CD-ROM content] (2007), pp. 1858-1902.

Kim et al. Hazardous Waste Treatment Technologies. Water Environment Research, vol. 64, No. 4, 1992: Literature Review (Jun. 1992), pp. 469-479.

Kim et al. Single enzyme nanoparticles in nanoporous silica: A hierarchical approach to enzyme stabilization and mmobilization. Enzyme and Microbial Technology 39 (2006) 474-480.

Kim et al. Nanobiocatalysis and its potential applications. Trends in Biotechnology vol. 26, No. 11, (2008) 639-646.

Neto. Process Considerations for the Asymmetric Synthesis of Chiral Amines using w-Transaminase. Thesis, Center for Process Engineering and Technology Department of Chemical and Biochemical Engineering Technical University of Denmark, Aug. 2013, pp. 1-108 and 109-117.

Rai et al. Optimization for production of liquid nitrogen fertilizer from the degradation of chicken feather by iron-oxide (Fe3O4) magnetic nanoparticles coupled β-keratinase. Biocatalysis and Agricultural Biotechnology, vol. 4, Issue 4, Oct. 2015, pp. 1-13.

Sanders et al. Self-Assembly Using Dynamic Combinatorial Chemistry. Philosophical Transactions: Mathematical, Physical and Engineering Sciences, vol. 362, No. 1819, Organizing Atoms: Manipulation of Matter on the Sub-10 nm Scale (Jun. 15, 2004), pp. 1239-1245.

Sheldon et al. Enzyme immobilisation in biocatalysis: why, what and how. Chem. Soc. Rev. 2013, vol. 42, 6223-6225.

Tappel et al. E. Lipoxidase. H. F. Linskens et al. (eds.), Modem Methods of Plant Analysis / Moderne Methoden der Pflanzenanalyse © Springer-Verlag OHG. Berlin 500 Göttingen • Heidelberg 1964, pp. 469-471.

Tundo et al. Methods and Reagents for Green Chemistry: An Introduction. 2007. A John Wiley & Sons Inc. Publication, pp. 1-312 (333 pages total).

Villaverde et al. Hydroperoxide production from linoleic acid by heterologous Gaeumannomyces graminis tritici lipoxygenase: Optimization and scale-up. Chemical Engineering Journal 217 (2013) 82-90.

Villaverde et al. Analysis of linoleic acid hydroperoxides generated by biomimetic and enzymatic systems through an integrated methodology. Industrial Crops and Products 34 (2011) 1474-1481.

Wang et al. Enhanced phenol degradation in coking wastewater by immobilized laccase on magnetic mesoporous silica nanoparticles in a magnetically stabilized fluidized bed. Bioresource Technology 110 (2012) 120-124.

Wilson et al. Glucose oxidase: an ideal enzyme. Biosensors and Bioelectronics 7 (1992) 165-185.

Zheng et al. Effect of molecular mobility on coupled enzymatic reactions involving cofactor regeneration using nanoparticle-attached enzymes Journal of Biotechnology 154 (2011) 274-280.

The Journal Record News Briefs: Feb. 15, 2010, The Journal Record (Oklahoma City, OK) Feb. 15, 2010 Monday, pp. 1-5.

Three better ways to upcycle waste oil; NUS researchers offer cheaper, greener methods to produce biodiesel The Straits Times (Singapore), Apr. 18, 2015 Saturday, pp. 1-2.

English abstract only of International Application No. WO 03/084982.

Chinese Office Action dated Apr. 28, 2015 received from Application No. 201280022702.9, together with an English-language translation.

Azevedo A.M. et al., "Horseradish Peroxidase: A Valuable Tool in Biotechnology", Biotechnology Annual Review 9:199-247 (2003).

Chalkias N.G. et al., "Activity Increase of Horseradish Peroxidase in the Presence of Magnetic Particles", J. Am. Chem. Soc. 130:2910-2911 (2008).

Corgie S.C. et al., "Self-Assembled Complexes of Horseradish Peroxidase with Magnetic Nanoparticles Showing Enhanced Peroxidase Activity", Advanced Functional Materials 22:1940-1951 (Feb. 15, 2012).

Corvini P.F.X. et al., "LANCE: Laccase-Nanoparticle Conjugates for the Elimination of Micropollutants (Endocrine Disrupting Chemicals) from Wastewater in Bioreactors", Rev Environ Sci Biotechnol 9:23-27 (2010).

Huang J. et al., "Zinc Tetraaminophthalocyanine-Fe3O4 Nanoparticle Composite for Laccase Immobilization", International Journal of Nanomedicine 2(4):775-784 (2007).

Luo X-L et al., "Electrochemically Deposited Chitosan Hydrogel for Horseradish Peroxidase Immobilization Through Gold Nanoparticles Self-Assembly", Biosensors and Bioelectronics 21:190-196 (2005).

Tang D. et al., "Direct Electrochemical Immunoassay Based on Immobilization of Protein-Magnetic Nanoparticle Composites on to Magnetic Electrode Surfaces by Sterically Enhanced Magnetic Field Force", Biotechnology Letters 28:559-565 (2006).

Wang F. et al., "Magnetic Mesoporous Silica Nanoparticles: Fabrication and Their Laccase Immobilization Performance", Bioresource Technology 101:8931-8935 (2010).

Yang H-H et al., "Magnetite-Containing Spherical Silica Nanoparticles for Biocatalysis and Bioseparations", Analytical Chemistry 76(5):1316-1321 (Mar. 1, 2004).

(56) References Cited

OTHER PUBLICATIONS

International Search Report dated Oct. 10, 2012 received from the Korean Intellectual Property Office from related Application No. PCT/US2012/028392.

* cited by examiner (4A)

M25
Average perimeter: 56.6 nm
Average area: 74.5 nm$^2$
Average Equivalent Circular Diameter: 8.5 nm M25-BNCs
Average perimeter: 67.9 nm
Average area: 123.3 nm$^2$
Equivalent Circular Diameter: 11.6 nm M90
Average perimeter: 425 nm
Average area: 6752 nm$^2$
Average Equivalent Circular Diameter: 63.9 nm (5A)

(5B)

(5C)

M90-BNCs
Average perimeter: 652 nm
Average area: 18580 nm$^2$
Average Equivalent Circular Diameter: 102.3 nm (5D)

(5E)

(5F)

| In assay | In premix | | | | | | | |
|---|---|---|---|---|---|---|---|---|
| | A H₂O | | B 0.5x PBS | | C 1x PBS | | D 2x PBS | |
| | Normalized avtivity | Stdev | Normalized avtivity | Stdev | Normalized avtivity | Stdev | Normalized avtivity | Stdev |
| 1 H₂O | 25.95 | 1.14 | 8.28 | 1.77 | 2.81 | 0.63 | 1.23 | 0.10 |
| 2 0.5x PBS | 22.80 | 1.49 | 5.44 | 0.45 | 0.91 | 0.07 | 1.09 | 0.02 |
| 3 1x PBS | | | 4.74 | 0.93 | 1.29 | 0.05 | 1.10 | 0.09 |
| 4 2x PBS | 20.87 | 0.29 | 4.26 | 0.05 | 1.37 | 0.19 | 0.94 | 0.10 |

FIG. 11B

| In assay | | In premix | | | | | | | |
|---|---|---|---|---|---|---|---|---|---|
| | | A H₂O | | B 0.5x SMB | | C 1x SMB | | D 2x SMB | |
| | | Normalized avtivity | Stdev | Normalized avtivity | Stdev | Normalized avtivity | Stdev | Normalized avtivity | Stdev |
| 1 | H₂O | 18.18 | 1.79 | 19.16 | 0.91 | 19.83 | 4.96 | 13.96 | 0.37 |
| 2 | 0.5x SMB | 20.26 | 2.84 | 17.69 | 2.03 | 16.42 | 0.24 | 14.52 | 1.06 |
| 3 | 1x SMB | 23.78 | 0.71 | 17.61 | 1.91 | 16.42 | 1.82 | 12.07 | 0.67 |
| 4 | 2x SMB | 26.58 | 3.16 | 18.52 | 1.14 | 18.06 | 1.00 | 13.21 | 0.15 |

FIG. 12B

|  | In assay | In premix | | | | | | | |
|---|---|---|---|---|---|---|---|---|---|
|  |  | A H₂O | | B 0.5x STB | | C 1x STB | | D 2x STB | |
|  |  | Normalized avtivity | Stdev | Normalized avtivity | Stdev | Normalized avtivity | Stdev | Normalized avtivity | Stdev |
| 1 | H₂O | 23.96 | 2.60 | 15.54 | 0.51 | 14.27 | 1.32 | 10.09 | 1.22 |
| 2 | 0.5x STB | 17.15 | 1.34 | 9.07 | 1.57 | 4.65 | 0.40 | 2.82 | 0.19 |
| 3 | 1x STB | 11.32 | 3.14 | 7.96 | 0.43 | 4.46 | 0.36 | 2.06 | 0.01 |
| 4 | 2x STB | 14.75 | 0.87 | 0.67 | 0.01 | 4.46 | 0.09 | 0.30 | 0.01 |

FIG. 13B

MESOPOROUS CATALYSTS OF MAGNETIC NANOPARTICLES AND FREE-RADICAL-PRODUCING ENZYMES, AND METHODS OF USE

CROSS-REFERENCE TO RELATED APPLICATIONS

This application claims priority from U.S. Provisional Application No. 61/568,966, filed Dec. 9, 2011, and U.S. Provisional Application No. 61/451,360, filed Mar. 10, 2011, both of which are herein incorporated by reference in their entirety.

STATEMENT REGARDING FEDERALLY SPONSORED RESEARCH

This invention was made with government support under contract to the Northeast Sun Grant Initiative at Cornell University US Department of Transportation Assistance #DTOS59-07-G-00052. The government has certain rights in the invention.

BACKGROUND OF THE DISCLOSURE

Peroxidases (EC 1.11.1) are widely found in biological systems and form a subset of oxidoreductases that reduce hydrogen peroxide ($H_2O_2$) to water in order to oxidize a large variety of aromatic compounds ranging from phenol to aromatic amines. The reaction cycle of peroxidases is quite complex and begins with activation of heme by $H_2O_2$ to form the two-electron activated Compound I (N. C. Veitch, *Phytochemistry*, 2004, 65, 249). Compound I is then reduced by one electron by the oxidation of the organic substrate leading to the formation of Compound II that is one electron above the resting state. The second reduction recovers the enzyme to its resting state to start a new cycle. Overall, for each molecule of hydrogen peroxide consumed, two aromatic free radicals are produced and can readily react in secondary reactions.

Peroxidases are highly sensitive to substrate inhibition, mostly by $H_2O_2$, which can lead to the formation of the reversible inactivated form of the enzyme (Compound III). Their activities are also deterred by product inhibition. Therefore, the complex kinetics associated with peroxidase enzymes can restrict their use in many processes and bioprocesses. Increasing the activities of this family of enzymes and their tolerance to different process conditions could improve their current use, as well as pave the way for their use in new applications.

BRIEF SUMMARY OF THE DISCLOSURE

It has been discovered herein that bionanocatalysts (BNCs) consisting of a free-radical-producing (FRP) enzyme, e.g., horseradish peroxidase (HRP), self-assembled with magnetic nanoparticles (MNPs) enhance enzymatic activity. In particular, it has herein been surprisingly found that the self-assembled clusters of FRP enzyme and magnetic nanoparticles generally possess faster turnover and lower inhibition of the enzyme as compared with the free enzyme or the magnetic nanoparticle clusters without enzyme. It has herein furthermore been found that the size and magnetization of the MNPs affect the formation and ultimately the structure of the BNCs, all of which have a significant impact on the activity of the entrapped enzymes. Particularly by virtue of their surprising resilience under various reaction conditions, the BNCs described herein can be used as an improved FRP agent where other such agents are currently used, and they can furthermore be used in other applications where FRP enzyme has not yet been considered or found applicable.

The approach described herein sharply differs from classical methods that rely on protein conjugation on surface-modified particles by complex biochemistries, oftentimes at the expense of enzymatic activities and reaction efficiencies. By the instant methodology, HRP kinetics are substantially modified only when the enzymes are in close association with the MNPs, e.g., as a self-assembled cluster (agglomeration) of primary MNP crystallites and peroxidase enzyme. The overall activities of the resulting BNCs can advantageously be orders of magnitude higher than those of free enzymes or MNPs at biologically relevant substrate concentration.

In one aspect, the invention is directed to a composition in which FRP enzyme is embedded (i.e., entrapped) in magnetic nanoparticles or clusters thereof. In particular embodiments, the composition is a mesoporous clustered assembly of magnetic nanoparticles and one or a combination of FRP enzyme. The mesoporous clustered assemblies possess mesopores in which FRP enzyme is embedded. In other embodiments, the foregoing cluster composition includes magnetic nanoparticles that are surface-coated with gold. In yet other embodiments, the foregoing cluster composition further includes micron- or submicron-sized magnetic microparticles on which FRP-embedded magnetic nanoparticles reside.

In other aspects, the invention is directed to processes in which the above-described FRP-embedded magnetic nanoparticle compositions are useful. In particular embodiments, the FRP-embedded magnetic nanoparticle compositions are directed to a process for depolymerizing lignin, a process for removing aromatic contaminants from water, and a process for producing a polymer by polymerizing a monomer by a free radical mechanism.

In yet another aspect, the invention is directed to a process for producing the FRP-embedded magnetic nanoparticle compositions described above. In some embodiments, magnetic nanoparticles or aggregates thereof are first prepared, and FRP enzyme is subsequently absorbed therein or attached thereto. In other embodiments, the FRP-embedded magnetic nanoparticle composition is produced by performing a magnetic nanoparticle synthesis in the presence of a FRP enzyme, thereby embedding the FRP enzyme in clusters of MNPs by a self-assembly mechanism.

BRIEF DESCRIPTION OF THE FIGURES

FIGS. 11A, 11B. 96-well plate for the phenol/AAP assay and lay-out used for determining effect of PBS buffer on BNC formation and activity (FIG. 11A), and chart showing increased activity data (normalized by the activity of the free enzyme) for M90-BNCs in $H_2O$ and varying concentration of phosphate buffer saline (PBS) (FIG. 11B). The conditions to form BNCs were investigated with the phenol/AAP assay with a fixed concentration of $H_2O_2$ (i.e., peroxide) at 1 mM. BNCs were formed in PBS buffer at different ionic strengths (up to 200 mM). The increase in activity decreased when the ionic strength of the buffer increased. The highest increase in activity was observed for the BNCs formed in water (no ionic compensation charge). BNCs formed in water showed an increase in activity up to 26 times and can be used at higher concentration of PBS in the assay.

FIGS. 12A, 12B. 96-well plate for the phenol/AAP assay and lay-out used for determining effect of malonate buffer on BNC formation and activity (FIG. 12A), and chart showing increased activity data (normalized by the activity of the free enzyme) for M90-BNCs in $H_2O$ and varying concentration of sodium malonate buffer (SMB) (FIG. 12B). The conditions to form BNCs were investigated with the phenol/AAP assay with a fixed concentration of peroxide (1 mM). BNCs were formed in an organic buffer (sodium malonate: SMB) at different ionic strengths (up to 200 mM). The increase in activity decreased when the ionic strength of the buffer increased, but was an order of magnitude higher than the BNCs formed in PBS. The highest increase in activity was observed for the BNCs formed in water (no ionic compensation charge). BNCs formed in SMB showed an increase in activity up to 26 times and can be used at higher concentration of SMB in the assay.

FIGS. 13A, 13B. 96-well plate for the phenol/AAP assay and lay-out used for determining effect of tartrate buffer on BNC formation and activity (FIG. 13A), and chart showing increased activity data (normalized by the activity of the free enzyme) for M90-BNCs in $H_2O$ and varying concentration of sodium tartrate buffer (STB) (FIG. 13B). The conditions to form BNCs were investigated with the phenol/AAP assay with a fixed concentration of peroxide (1 mM). BNCs were formed in an organic buffer (sodium tartrate: STB) at different ionic strengths (up to 200 mM). The increase in activity decreased when the ionic strength of the buffer increased, but was an order of magnitude higher than the BNCs formed in PBS. The highest increase in activity was observed for the BNCs formed in water (no ionic compensation charge). BNCs formed in STB showed an increase in activity up to 24 times and can be used at higher concentration of STB in the assay.

FIG. 28A compares solutions of HRP/Gox (left) and HRP/Gox BNCs (right) in 1 mM glucose solution. FIG. 28B compares the same solutions after exposure to an external magnet.

FIG. 28C shows the μBNCs stirred by an external rotating magnet. As shown, the μBNCs can be retrieved from solution after the reaction in a matter of seconds even with low magnetic fields, and can also be easily stirred with external magnetic fields. The darker color of the HRP/Gox-BNC system immobilized on microparticles (right tube) also indicated that the extent of the reaction is higher compared to the free enzyme (left tube) after 10 hours.

DETAILED DESCRIPTION OF THE DISCLOSURE

Figure 1:
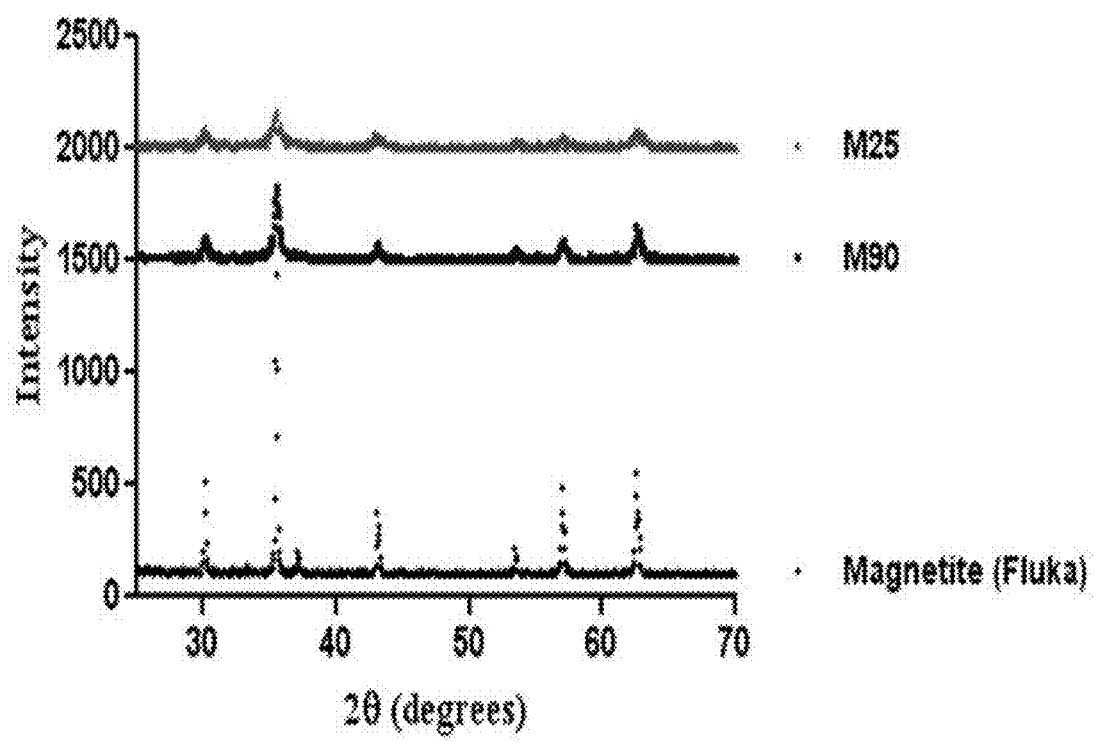
FIG. 1. X-ray diffraction patterns of magnetite nanoparticles synthesized at 25° C. and 90° C. The synthesized nanoparticles show the characteristic X-ray diffraction pattern of magnetite. The intensity of the crystallite diffraction peaks differs between the nanoparticles formed at 25° C. (smaller size) and the ones formed at 90° C. (bigger size).

In one aspect, the invention is directed to a free-radical producing (FRP) composition that includes magnetic nanoparticles bound to FRP enzyme. Magnetic nanoparticles bound to FRP enzyme is herein also referred to as a "bionanocatalyst" or "BNC". As used herein, the term "bound" is intended to include any of the means by which FRP enzyme can be attached to magnetic nanoparticles without the release of FRP enzyme from the magnetic nanoparticles under conditions in which they are used or stored for later use. The FRP enzyme can be bound by, for example, covalent, ionic, hydrogen bonding, affinity, or van der Waals interactions. The FRP enzyme may be located anywhere on the magnetic nanoparticle, e.g., on the surface and/or embedded within the magnetic nanoparticle, such as in mesopores of the magnetic nanoparticles if the magnetic nanoparticles are porous. As used herein, the term "magnetic" encompasses all types of useful magnetic characteristics, including permanent magnetic, superparamagnetic, paramagnetic, ferromagnetic, and ferrimagnetic behaviors.

The magnetic nanoparticle or BNC has a size in the nanoregime, i.e., generally no more than 500 nm. As used herein, the term "size" can refer to a diameter of the magnetic nanoparticle when the magnetic nanoparticle is approximately or substantially spherical. In a case where the magnetic nanoparticle is not approximately or substantially spherical (e.g., substantially ovoid or irregular), the term "size" can refer to either the longest the dimension or an average of the three dimensions of the magnetic nanoparticle. The term "size" may also refer to an average of sizes over a population of magnetic nanoparticles (i.e., "average size"). In different embodiments, the magnetic nanoparticle has a size of no more than, for example, 500 nm, 400 nm, 300 nm, 200 nm, 100 nm, 50 nm, 40 nm, 30 nm, 25 nm, 20 nm, 15 nm, 10 nm, 5 nm, 4 nm, 3 nm, 2 nm, or 1 nm, or a size within a range bounded by any two of the foregoing exemplary sizes.

The magnetic nanoparticles described above or BNCs thereof may be clustered, i.e., as aggregates or agglomerations, in which case the above-described magnetic nanoparticles are considered to be primary nanoparticles (i.e., primary crystallites) and the magnetic nanoparticle sizes provided above can be considered to be primary nanoparticle sizes. The aggregates generally have a size (i.e., secondary size) of at least 5 nm. In different embodiments, the aggregates have a size of precisely, about, or at least, for example, 5 nm, 8 nm, 10 nm, 12 nm, 15 nm, 20 nm, 25 nm, 30 nm, 35 nm, 40 nm, 45 nm, 50 nm, 60 nm, 70 nm, 80 nm, 90 nm, 100 nm, 150 nm, 200 nm, 300 nm, 400 nm, 500 nm, 600 nm, 700 nm, or 800 nm, or a size within a range bounded by any two of the foregoing exemplary sizes.

Typically, the primary and/or aggregate magnetic nanoparticles or BNCs thereof have a distribution of sizes, i.e., they are generally dispersed in size, either narrowly or broadly dispersed. In different embodiments, any range of primary or aggregate sizes can constitute a major or minor proportion of the total range of primary or aggregate sizes. For example, in some embodiments, a particular range of primary particle sizes (for example, at least 1, 2, 3, 5, or 10 nm and up to 15, 20, 25, 30, 35, 40, 45, or 50 nm) or a particular range of aggregate particle sizes (for example, at least 5, 10, 15, or 20 nm and up to 50, 100, 150, 200, 250, or 300 nm) constitutes at least or above 50%, 60%, 70%, 80%, 90%, 95%, 98%, 99%, or 100% of the total range of primary particle sizes. In other embodiments, a particular range of primary particle sizes (for example, less than 1, 2, 3, 5, or 10 nm, or above 15, 20, 25, 30, 35, 40, 45, or 50 nm) or a particular range of aggregate particle sizes (for example, less than 20, 10, or 5 nm, or above 25, 50, 100, 150, 200, 250, or 300 nm) constitutes no more than or less than 50%, 40%, 30%, 20%, 10%, 5%, 2%, 1%, 0.5%, or 0.1% of the total range of primary particle sizes.

The aggregates of magnetic nanoparticles (i.e., "aggregates") or BNCs thereof can have any degree of porosity, including a substantial lack of porosity depending upon the quantity of individual primary crystallites they are made of. In particular embodiments, the aggregates are mesoporous by containing interstitial mesopores (i.e., mesopores located between primary magnetic nanoparticles, formed by packing arrangements). The mesopores are generally at least 2 nm and up to 50 nm in size. In different embodiments, the mesopores can have a pore size of precisely or about, for example, 2, 3, 4, 5, 10, 12, 15, 20, 25, 30, 35, 40, 45, or 50 nm, or a pore size within a range bounded by any two of the foregoing exemplary pore sizes. Similar to the case of particle sizes, the mesopores typically have a distribution of sizes, i.e., they are generally dispersed in size, either narrowly or broadly dispersed. In different embodiments, any range of mesopore sizes can constitute a major or minor proportion of the total range of mesopore sizes or of the total pore volume. For example, in some embodiments, a particular range of mesopore sizes (for example, at least 2, 3, or 5, and up to 8, 10, 15, 20, 25, or 30 nm) constitutes at least or above 50%, 60%, 70%, 80%, 90%, 95%, 98%, 99%, or 100% of the total range of mesopore sizes or of the total pore volume. In other embodiments, a particular range of mesopore sizes (for example, less than 2, 3, 4, or 5 nm, or above 10, 15, 20, 25, 30, 35, 40, 45, or 50 nm) constitutes no more than or less than 50%, 40%, 30%, 20%, 10%, 5%, 2%, 1%, 0.5%, or 0.1% of the total range of mesopore sizes or of the total pore volume.

The magnetic nanoparticles can have any of the compositions known in the art. In some embodiments, the magnetic nanoparticles are or include a zerovalent metallic portion that is magnetic. Some examples of such zerovalent metals include cobalt, nickel, and iron, and their mixtures and alloys. In other embodiments, the magnetic nanoparticles are or include an oxide of a magnetic metal, such as an oxide of cobalt, nickel, or iron, or a mixture thereof. In some embodiments, the magnetic nanoparticles possess distinct core and surface portions. For example, the magnetic nanoparticles may have a core portion composed of elemental iron, cobalt, or nickel and a surface portion composed of a passivating layer, such as a metal oxide or a noble metal coating, such as a layer of gold, platinum, palladium, or silver. In other embodiments, metal oxide magnetic nanoparticles or aggregates thereof are coated with a layer of a noble metal coating. The noble metal coating may, for example, reduce the number of charges on the magnetic nanoparticle surface, which may beneficially increase dispersibility in solution and better control the size of the BNCs. Noble metal coating protects the particles against oxidation, solubilization by leaching or by chelation when chelating organic acids such as citrate, malonate, tartrate for examples are used in the biochemical reactions or processes. The passivating layer can have any suitable thickness, and particularly, at least, up to, or less than, for example, 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, or 10 nm, or a thickness in a range bounded by any two of these values.

In particular embodiments, the magnetic nanoparticles have an iron oxide composition. The iron oxide composition can be any of the magnetic or superparamagnetic iron oxide compositions known in the art, e.g., magnetite ($Fe_3O_4$), hematite ($\alpha$-$Fe_2O_3$), maghemite ($\gamma$-$Fe_2O_3$), or a spinel ferrite according to the formula $AB_2O_4$, wherein A is a divalent metal (e.g., $Zn^{2+}$, $Ni^{2+}$, $Mn^{2+}$, $Co^{2+}$, $Ba^{2+}$, $Sr^{2+}$, or combination thereof) and B is a trivalent metal (e.g., $Fe^{3+}$, $Cr^{3+}$, or combination thereof).

In some embodiments, the magnetic nanoparticles or aggregates thereof or BNCs thereof reside on the surface of ferromagnetic sub-micrometric particles. By residing on the surface of ferromagnetic microparticles, the magnetic nanoparticles or aggregates or BNCs are attached to the surface of the ferromagnetic microparticles by any suitable associative, adsorptive, or bonding interaction. The ferromagnetic microparticles may or may not be coated with a metal oxide or noble metal coating layer. Moreover, the ferromagnetic microparticles may possess any suitable surface groups, as well known in the art, which may promote attachment of the magnetic nanoparticles thereto. In different embodiments, the ferromagnetic microparticles have a size of about, precisely, or at least 20, 30, 40, or 50, 60, 70, 80, 90, 100, 100, 200, 300, 400, 500, 600, 700, 800, 900, 1000 nm, or a size within a range bounded by any two of the foregoing exemplary sizes. By virtue of their larger size (ultrastructure), BNCs attached onto the surface of ferromagnetic particles can be more easily captured by an external magnetic field. The larger size also helps to preserve enzymatic activities. These bigger magnetic particles can be easily captured by external magnetic fields. BNCs attached onto the surface of ferromagnetic submicrometric particles are not prone to over aggregation when subjected to magnetic fields.

The magnetic nanoparticles or aggregates thereof or BNCs thereof possess any suitable degree of magnetism. For example, the magnetic nanoparticles or aggregates thereof or BNCs thereof can possess a saturated magnetization ($M_s$) of at least or up to 5, 10, 15, 20, 25, 30, 40, 45, 50, 60, 70, 80, 90, or 100 emu/g. The magnetic nanoparticles or aggregates thereof preferably possess a remanent magnetization ($M_r$) of no more than (i.e., up to) or less than 5 emu/g, and more preferably, up to or less than 4 emu/g, 3 emu/g, 2 emu/g, 1 emu/g, 0.5 emu/g, or 0.1 emu/g. The surface magnetic field of the magnetic nanoparticles or aggregates thereof can be about or at least, for example, 5, 10, 50, 100, 200, 300, 400, 500, 600, 700, 800, 900, or 1000 Gauss (G), or a magnetic field within a range bounded by any two of the foregoing values.

The magnetic nanoparticles or aggregates thereof can be made to adsorb a suitable amount of FRP enzyme, up to or below a saturation level, depending on the application, to produce the resulting BNC. In different embodiments, the magnetic nanoparticles or aggregates thereof may adsorb about, at least, up to, or less than, for example, 1, 5, 10, 15, 20, 25, or 30 pmol/m$^2$ of FRP enzyme. Alternatively, the magnetic nanoparticles or aggregates thereof may adsorb an amount of FRP enzyme that is about, at least, up to, or less than, for example, 10%, 20%, 30%, 40%, 50%, 60%, 70%, 80%, 90%, or 100% of a saturation level.

The magnetic nanoparticles or aggregates thereof or BNCs thereof possess any suitable pore volume. For example, the magnetic nanoparticles or aggregates thereof can have a pore volume of about, at least, up to, or less than, for example, 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm$^3$/g, or a pore volume within a range bounded by any two of the foregoing values.

The magnetic nanoparticles or aggregates thereof or BNCs thereof possess any suitable specific surface area. For example, the magnetic nanoparticles or aggregates thereof can have a specific surface area of about, at least, up to, or less than, for example, 50, 60, 70, 80, 90, 100, 110, 120, 130, 140, 150, 160, 170, 180, 190, or 200 m$^2$/g.

The FRP enzyme can be any enzyme that produces free radicals. Moreover, the FRP enzyme can be from any source, e.g., fungal, microbial, animal, or plant. In particular embodiments, the FRP enzyme is an oxidoreductase belonging to the EC 1 family of enzymes. The EC 1 oxidoreductase can be, for example, an EC 1.1 oxidoreductase acting on the CH—OH groups of donors, an EC 1.2 oxidoreductase acting on the aldehyde or oxo group of donors, an EC 1.3 oxidoreductase acting on the CH—CH group of donors, an EC 1.4 oxidoreductase acting on the CH—NH$_2$ group of donors, an EC 1.5 oxidoreductase acting on the CH—NH group of donors, an EC 1.6 oxidoreductase acting on NADH or NADPH, an EC 1.7 oxidoreductase acting on various nitrogenous compounds as donors, an EC 1.8 oxidoreductase acting on a sulfur group as donor, an EC 1.9 oxidoreductase acting on a heme group of donors, an EC 1.10 oxidoreductase acting on diphenols and related substances as donors, an EC 1.11 oxidoreductase acting on peroxide as an acceptor, an EC 1.12 oxidoreductase acting on hydrogen as a donor, an EC 1.13 oxidoreductase acting on single donors with incorporation of molecular oxygen (oxygenases), an EC 1.14 oxidoreductase acting on paired donors with incorporation or reduction of molecular oxygen, an EC 1.15 oxidoreductase acting on superoxide as an acceptor, an EC 1.16 oxidoreductase that oxidize metal ions, an EC 1.17 oxidoreductase acting on CH or CH$_2$ groups, an EC 1.18 oxidoreductase acting on iron-sulfur proteins as a donor, an EC 1.19 oxidoreductase acting on reduced flavodoxin as a donor, an EC 1.20 oxidoreductase acting on phosphorus or arsenic as a donor, an EC 1.21 oxidoreductase acting on X—H and Y—H to form an X—Y bond, an EC 1.97 oxidoreductase, an EC 1.98 oxidoreductase that uses hydrogen as a reductant, and an EC 1.99 oxidoreductase that uses oxygen as an oxidant. The oxidoreductase may also be more particularly identified as belonging to a sub-genus of any of the EC 1.1 groupings provided above.

In a first particular set of embodiments, the FRP enzyme is selected from the EC 1.1 genus of oxidoreductase enzymes. The EC 1.1 enzyme can further be identified as belonging to any of the following sub-genuses: EC 1.1.1 with NAD or NADP as acceptor, EC 1.1.2 with a cytochrome as acceptor, EC 1.1.3 with oxygen as acceptor, EC 1.1.4 with disulfide as acceptor, EC 1.1.5 with quinone or similar compound as acceptor, and EC 1.1.99 with other acceptors. In more particular embodiments, the FRP enzyme is identified as belonging to a sub-genus of any of the EC 1.1 sub-genuses provided above. For example, the FRP enzyme can be identified as belonging to any of the sub-genuses of EC 1.1.3, such as EC 1.1.3.3 (malate oxidase), EC 1.1.3.4 (glucose oxidase), EC 1.1.3.5 (hexose oxidase), EC 1.1.3.6 (cholesterol oxidase), EC 1.1.3.7 (aryl-alcohol oxidase), EC 1.1.3.8 (L-gulonolactone oxidase), EC 1.1.3.9 (galactose oxidase), EC 1.1.3.10 (pyranose oxidase), EC 1.1.3.11 (L-sorbose oxidase), EC 1.1.3.12 (pyridoxine 4-oxidase), EC 1.1.3.13 (alcohol oxidase), EC 1.1.3.14 (catechol oxidase), EC 1.1.3.15 (2-hydroxy acid oxidase), EC 1.1.3.16 (ecdysone oxidase), EC 1.1.3.17 (choline oxidase), EC 1.1.3.18 (secondary-alcohol oxidase), EC 1.1.3.19 (4-hydroxymandelate oxidase), EC 1.1.3.20 (long-chain alcohol oxidase), EC 1.1.3.21 (glycerol-3-phosphate oxidase), EC 1.1.3.22, EC 1.1.3.23 (thiamine oxidase), EC 1.1.3.24 (L-galactonolactone oxidase), EC 1.1.3.25, EC 1.1.3.26, EC 1.1.3.27 (hydroxyphytanate oxidase), EC 1.1.3.28 (nucleoside oxidase), EC 1.1.3.29 (N-acylhexosamine oxidase), EC 1.1.3.30 (polyvinyl alcohol oxidase), EC 1.1.3.31, EC 1.1.3.32, EC 1.1.3.33, EC 1.1.3.34, EC 1.1.3.35, EC 1.1.3.36, EC 1.1.3.37 D-arabinono-1,4-lactone oxidase), EC 1.1.3.38 (vanillyl alcohol oxidase), EC 1.1.3.39 (nucleoside oxidase, H$_2$O$_2$ forming), EC 1.1.3.40 (D-mannitol oxidase), and EC 1.1.3.41 (xylitol oxidase).

In a second particular set of embodiments, the FRP enzyme is selected from the EC 1.10 genus of oxidoreductase enzymes. The EC 1.10 enzyme can further be identified as belonging to any of the following sub-genuses: EC 1.10.1 with NAD or NADP as acceptor EC 1.10.2 with cytochrome as acceptor, EC 1.10.3 with oxygen as acceptor, and EC 1.10.99 with other acceptors. The EC 1.10.1 enzyme can be more specifically, for example, EC 1.10.1.1, i.e., trans-acenaphthene-1,2-diol dehydrogenase. The EC 1.10.2 enzyme can be more specifically, for example, EC 1.10.2.1 (cytochrome-b5 reductase) or EC 1.10.2.2 (cytochrome-c reductase). The EC 1.10.3 enzyme can be more specifically, for example, EC 1.10.3.1 (catechol oxidase), EC 1.10.3.2 (laccase), EC 1.10.3.3 (L-ascorbate oxidase), EC 1.10.3.4 (o-aminophenol oxidase), EC 1.10.3.5 (3-hydroxyanthranilate oxidase), EC 1.10.3.6 (rifamycin-B oxidase), EC 1.10.3.7, or EC 1.10.3.8. The EC 1.10.99 enzyme can be more specifically, for example, EC 1.10.99.1 (plastoquinol-plastocyanin reductase), EC 1.10.99.2 (ribosyldihydronicotinamide dehydrogenase, quinone), or EC 1.10.99.3 (violaxanthin de-epoxidase).

In a third particular set of embodiments, the FRP enzyme is selected from the EC 1.11 genus of oxidoreductase enzymes. The EC 1.11 enzyme can further be identified as belonging to the sub-genus EC 1.11.1 (peroxidases). The EC 1.11.1 enzyme can be more specifically, for example, EC 1.11.1.1 (NADH peroxidase), EC 1.11.1.2 (NADPH peroxidase), EC 1.11.1.3 (fatty acid peroxidase), EC 1.11.1.4, EC 1.11.1.5 (cytochrome-c peroxidase), EC 1.11.1.6 (catalase), EC 1.11.1.7 (peroxidase), EC 1.11.1.8 (iodide peroxidase), EC 1.11.1.9 (glutathione peroxidase), EC 1.11.1.10 (chloride peroxidase), EC 1.11.1.11 (L-ascorbate peroxidase), EC 1.11.1.12 (phospholipid-hydroperoxide glutathione peroxidase), EC 1.11.1.13 (manganese peroxidase), EC 1.11.1.14 (diarylpropane peroxidase), or EC 1.11.1.15 (peroxiredoxin).

In particular embodiments, the FRP enzyme is a peroxidase. The peroxidase may also be further specified by function, e.g., a lignin peroxidase, manganese peroxidase, or versatile peroxidase. The peroxidase may also be specified as a fungal, microbial, animal, or plant peroxidase. The peroxidase may also be specified as a class I, class II, or class III peroxidase. The peroxidase may also be specified as a myeloperoxidase (MPO), eosinophil peroxidase (EPO), lactoperoxidase (LPO), thyroid peroxidase (TPO), prostaglandin H synthase (PGHS), glutathione peroxidase, haloperoxidase, catalase, cytochrome c peroxidase, horseradish peroxidase, peanut peroxidase, soybean peroxidase, turnip peroxidase, tobacco peroxidase, tomato peroxidase, barley peroxidase, or peroxidasin. In particular embodiments, the peroxidase is horseradish peroxidase.

In some embodiments, a single FRP enzyme is used. In other embodiments, a combination of FRP enzymes is used, such as any two or three oxidoreductase enzymes selected from any of the above classes or sub-classes therein. In some embodiments, a combination of FRP enzymes (e.g., EC 1 enzymes) is used. In particular embodiments, a combination of EC 1.1 enzymes is used. In other particular embodiments, a combination of EC 1.10 enzymes is used. In other particular embodiments, a combination of EC 1.11 enzymes is used. In other embodiments, a combination of any of the particular FRP enzymes described above and a peroxidase is used (e.g., a combination of a EC 1.1 or EC 1.1.3 enzyme and a peroxidase). When a combination of FRP enzymes is used, the two or more enzymes may be arranged in a core-shell type of arrangement, i.e., a first FRP enzyme is either in a core portion or surface portion of the magnetic nanoparticle or aggregate thereof, and a second (different) FRP enzyme covers the region where the first FRP enzyme is located. The second FRP enzyme may be an aggregate of the magnetic nanoparticle or on the surface thereof, overlaying the first enzyme. In the case of multiple enzyme systems, manipulating the distribution of the different enzymes within the mesoporous aggregates offers the advantage of decoupling the different reactions and permitting diffusion of the substrates and products of the reactions from one layer to another layer or to the core of the BNCs. Therefore, when performing the enzymatic reactions in the confined pore structures of the BNCs, core/shell distributions offer the possibility of better controlling the kinetics of the different entrapped FRP enzymes. Combining enzymes that perform similar reactions (such as two, or more, peroxidases or a peroxidase and a laccase for example) but having different reaction requirements (substrates, substrate concentration, etc.) can beneficially increase the versatility of the BNCs to perform in broad and variable process conditions at a high level of efficiency. Combining enzymes with coupled reactions can ensure the production of the substrate in the vicinity of the enzyme and bypass the need for hazardous and labile chemical substrates, such as hydrogen peroxide. For example, a glucose oxidase enzyme can generate hydrogen peroxide from glucose, which is an inexpensive and non-hazardous compound.

The invention is also directed to methods of producing the enzyme-included (i.e., enzyme-bound, enzyme-trapped, or enzyme-embedded) magnetic nanoparticles and aggregates thereof. In particular embodiments, the enzyme-included magnetic nanoparticles or aggregates thereof are prepared by including an FRP enzyme in the reaction conditions used for preparing the magnetic nanoparticles or aggregates. For example, an FRP enzyme can be included in the process of generating metallic nanoparticles (e.g., cobalt, nickel, or iron) or metal oxide magnetic nanoparticles (e.g., an oxide of cobalt, nickel, or iron). Synthetic methods for producing metallic and metal oxide magnetic nanoparticles are well known in the art. One known method for producing metallic nanoparticles includes the reduction of metal ions (e.g., as a metal salt) in solution. The reduction can be accomplished by, for example, a reductive chemical method (e.g., by reaction with a reducing agent, such as hydrogen, a borane, hydrazine, hypophosphate, or citrate) or a reductive or decompositional physical method (e.g., sonication or thermal treatment in solution). The method may alternatively decompose a zerovalent metal complex (e.g., a $Ni^0$ carbonyl or phosphine complex) by, for example, sonication, thermal treatment, or exposure to a radiative source, such as ultraviolet light. A particular known method for producing metal oxide magnetic nanoparticles involves alkaline reaction with a metal salt (e.g., a metal halide) under conditions where metal oxide nanoparticles precipitate. For example, by well-established procedures, iron oxide nanoparticles can be produced by co-precipitation of iron (II) and iron (III) ions (e.g., as found in $FeCl_2$ and $FeCl_3$) in solution by reaction with a base, such as NaOH. The FRP enzyme can be included in any such method, as long as the method is not substantially detrimental to the activity of the FRP enzyme.

In other embodiments, the magnetic nanoparticles or aggregates thereof are first prepared, and then FRP enzyme is included on or in the magnetic nanoparticles or aggregates thereof. Particularly in the situation where the magnetic nanoparticles or aggregates are porous, the FRP enzyme can be embedded into the pores of the magnetic nanoparticles or aggregates in an aqueous-based solution by simple diffusion, adsorption, or self-assembly. In other embodiments, the surfaces and/or pores of the magnetic nanoparticles or aggregates thereof are derivatized with a bonding agent that causes or promotes bonding of the FRP enzyme to the magnetic nanoparticles or aggregates thereof. The bonding agent can be, for example, a difunctional linker that possesses a reactive end that binds to the magnetic nanoparticle and another reactive end that binds to the FRP enzyme. In the case of metallic nanoparticles, the reactive end that binds to the magnetic nanoparticle can be, for example, an amino, mercapto, mercaptoether, or phosphine group. In the case of metal oxide nanoparticles, the reactive end that binds to the magnetic nanoparticle can be, for example, a phosphate, phosphonate, sulfate, or sulfonate group. In either case, the reactive end that binds to the FRP enzyme can be, for example, any of the amine-reactive groups (e.g., N-hydroxysuccinimide group) known in the art, or any of the other groups known in the art for conjugating an enzyme or other protein to another moiety. The bonding agent may alternatively be, for example, based on affinity coupling, e.g., producing a magnetic nanoparticle-biotin or -avidin conjugate and reacting this with a FRP-avidin or -biotin conjugate, respectively.

The magnetic nanoparticles or aggregates thereof or BNCs thereof may also be coated with a noble metal, such as gold, platinum, or palladium. Any suitable method for coating the magnetic nanoparticles may be used. For example, in particular embodiments, magnetic nanoparticles are dispersed in a solution containing a noble metal salt, and the noble metal salt subjected to reducing conditions. The foregoing method can be facilitated by binding difunctional molecules onto the surface of the magnetic nanoparticles before the noble metal salt is reduced. The difunctional molecules used for this purpose should contain a portion useful for binding to the magnetic nanoparticles (as described above) as well as a noble metal binding portion (e.g., an amine, thiol, phosphine, or chelating moiety) for binding noble metal ions. Optionally, once metal ions are bound to the nanoparticle surface, the magnetic nanoparticles can be washed of excess noble metal salt (e.g., by filtration or decanting). Since noble metal ions are attached to the surface, the foregoing methodology provides a more selective method for producing a noble metal coating (i.e., without concomitant production of noble metal nanoparticles) as well as a more uniform coating. In some embodiments, the noble metal coating is applied before FRP enzyme is included with the magnetic nanoparticles, in which case FRP enzyme is later bonded to the noble metal coating. The FRP enzyme can be bonded to the noble metal coating by, for example, functionalizing the noble metal coating with difunctional molecules that bind to the noble metal coating and possess another reactive group for binding to the FRP enzyme.

The enzyme-containing magnetic nanoparticles or aggregates thereof, or noble-metal coated versions thereof, may also be bonded or adhered onto (i.e., be made to reside onto) the surface of ferromagnetic microparticles. In one embodiment, the enzyme-containing magnetic nanoparticles or aggregates thereof, or noble-metal coated versions thereof, are made to adhere onto the surface of ferromagnetic microparticles by contacting them in an aqueous-based solution and allowing the nanoparticles to adhere onto the surface of the microparticles. In other embodiments, the nanoparticles and microparticles are suitably functionalized with surface agents to facilitate a binding interaction, which may be based on, for example, covalent, ionic, affinity, hydrogen bonding, or van der Waals (dispersion) interactions.

In another aspect, the invention is directed to a process for depolymerizing lignin, i.e., a lignin depolymerization process, in which any of the enzyme-bound magnetic nanoparticles or aggregates thereof (i.e., BNCs) described above is used for depolymerizing or facilitating the depolymerization of lignin. The lignin being depolymerized can be any lignin-containing material. The precursor lignin can be any of a wide variety of lignin compositions found in nature or as known in the art.

As known in the art, there is no uniform lignin composition found in nature. Lignin is a random polymer that shows significant compositional variation between plant species. Many other conditions, such as environmental conditions, age, and method of processing, influence the lignin composition. Lignins differ mainly in the ratio of three alcohol units, i.e., p-coumaryl alcohol, guaiacyl alcohol, and sinapyl alcohol. The polymerization of p-coumaryl alcohol, coniferyl alcohol, and sinapyl alcohol forms the p-hydroxyphenyl (H), guaiacyl (G) and syringyl (S) components of the lignin polymer, respectively. The precursor lignin can have any of a wide variety of relative weight percents (wt %) of H, G, and S components. Besides the natural variation of lignins, there can be further compositional variation based on the manner in which the lignin has been processed. For example, the precursor lignin can be a Kraft lignin, sulfite lignin (i.e., lignosulfonate), or a sulfur-free lignin.

Lignin is the most abundant aromatic based biopolymer on Earth, but it is chemically recalcitrant to conversion and bioconversion due to the apparent randomness of its chemical composition and physical structure. Lignin can be considered a "glue" or "epoxy" between polysaccharide fibers that provides strength, rigidity, and protection to the cell walls of vascular plants. From a chemical standpoint, lignin is a highly heterogeneous polymer formed by the polymerization of phenyl-propanoid molecules including coniferyl, sinapyl and coumaryl alcohols via aryl linkages, ether linkages, and carbon-carbon bonds.

Based on the assumption that 100 gallons of ethanol are produced from 1 ton of biomass and that biomass (e.g., wood and grass) contains on average about 20% lignin, one can quickly estimate that a biorefinery operating on a 100 million gallon per year capacity would produce about 200,000 tons of lignin material. To meet a 20% replacement of gasoline for the U.S. only by 2020, equivalent to about 35 billion gallons of ethanol, a total of approximately 700 million tons of lignin would be produced per year. The actual production of lignin, mostly Kraft lignin as byproduct of the paper industry, is approximately 90 million tons per year worldwide. In other words, the lignin production worldwide would be increased by more than an order of magnitude.

Lignin can be used for low- or high-priced products based on the application and the degree of chemical purity. Until recently, markets for lignin products have not been large, competitive, or attractive enough to compensate for the cost of isolation and purification compared to the recovered energy derived from its burning. This is mainly because the cost of oil is still low enough and the supplies are high enough to provide the building blocks for the chemical and material industries. However, in a carbohydrate economy framework based on biofuels and bioproducts co-production, high-purity isolated lignin dedicated for conversion could be estimated at $1.10 per kg of raw material compared to $0.04, when used for co-firing. Low-end applications are mostly directed to dispersants, soil conditioners for carbon sequestration, adsorbents for fertilizers and pesticides, as well as fuels, which require little or no further conversion after extraction. High-end applications requiring depolymerization of lignin include the production of phenolic precursors (DMSO, vanillin, phenol, and aromatic compounds) and polymer components (e.g., epoxy resins, polyurethane foams, phenolic resins powders, carbon fibers and glue and binders).

In nature, the conversion of lignin is performed by specialist microbes, particularly fungi and bacteria. Lignocellulosic bacteria and fungus have the ability to depolymerize lignin in order to gain access to cellulosic fractions of biomass. To that end, lignocellulosic bacteria and fungus excrete an array of oxidoreductase enzymes, which include laccases, oxidases, and peroxidases, along with organic acids and $H_2O_2$-producing catalases. The most potent oxidoreductase enzymes are produced by a specific group of fungi known as white rot fungi, which specialize in lignocellulosic degradation. Various types of fungal peroxidases differ in the nature of their substrates.

Lignin peroxidase (LiP, E.C. 1.11.1.14) catalyzes the oxidative cleavage of C—C bonds in a number of model compounds, and oxidizes benzyl alcohols to aldehydes or ketones. Typical reactions catalyzed by lignin peroxidases are $C\alpha$-$C\alpha$ cleavage, $C\alpha$ oxidation, alkyl aryl cleavage, aromatic ring cleavage, demethylation, hydroxylation and polymerization. Lignin peroxidases are involved in the oxidative breakdown of lignin in white-rot basidiomycetes. Lignin peroxidase catalyzes the oxidation of non-phenolic aromatic rings into aryl cation radicals by $H_2O_2$. A typical example is the oxidation of veratryl alcohol (3,4-dimethoxybenzyl alcohol) into veratryl aldehyde (3,4-dimethoxybenz aldehyde) via the intermediary formation of veratryl cation and benzyl radicals: veratryl alcohol+$H_2O_2$→veratryl aldehyde+2 $H_2O$. Manganese peroxidase (MnP; E.C. 1.11.1.13) has lower redox potentials (up to 1.1 V) than LiP (up to 1.5 V) and catalyzes the Mn-mediated oxidation of lignin and phenolic compounds. This enzyme catalyzes the oxidation of Mn(II) to Mn(III) by $H_2O_2$. The highly reactive Mn(III) is stabilized via chelation in the presence of dicarboxylic acid: 2 Mn(II)+2 $H^+$+$H_2O_2$→2 Mn(III)+2 $H_2O$. The purpose of MnP is to generate small and potent oxidizing agents that diffuse into the lignified cell wall and achieve depolymerization of lignin from within. Versatile peroxidase (syn.

hybrid peroxidase, manganese-lignin peroxidase: VeP EC 1.11.1.16) is a fairly new ligninolytic enzyme, combining catalytic properties of manganese peroxidase (oxidation of Mn(II)), lignin peroxidase (Mn-independent oxidation of non-phenolic aromatic compounds) and plant peroxidase (oxidation of hydroquinones and substituted phenols). Any one or a combination of the above-mentioned peroxidases may be used in the lignin depolymerization process described herein.

In a first embodiment, the lignin-containing material is a form of lignin partially or substantially separated from other components of wood (e.g., cellulosic and hemicellulosic components), as is generally provided from a pretreatment process of lignocellulosic material, the details of which are well known in the art of lignocellulosic processing and conversion. The pretreatment process serves to either separate lignin from other components of the lignin-containing source, or to weaken the bonds between lignin and the other components. As is also well known in the art, the lignin may be further isolated by, for example, extraction. In a second embodiment, the lignin-containing material is a lignin-containing consumable product, such as paper or cardboard, which may or may not be pretreated. In a third embodiment, the lignin-containing material is a lignin-containing natural source (i.e., raw lignocellulosic material), such as woodchips, grasses (e.g., switchgrass and mixed grasses), corn stover (e.g., leaves, husks, stalks, or cobs of corn plants), sugarcane, saw dust, hemp, or a combination thereof, all of which are generally pretreated to make the lignin sufficiently available for depolymerization.

In the lignin depolymerization process, any of the enzyme-bound magnetic nanoparticles or aggregates thereof, described above, is contacted with a lignin-containing material under conditions where partial or complete depolymerization of lignin occurs by free-radical activity of the enzyme-bound magnetic nanoparticles or aggregates thereof. The enzyme-bound magnetic nanoparticles or aggregates thereof and the lignin-containing material are generally made to contact by combining them in an aqueous solution, such as an aqueous solution used in a pretreatment process of the lignin-containing material. In some embodiments, a room temperature condition (e.g., at least 15, 18, 20, or 22° C. and up to 25° C. or 30° C.) is used during the depolymerization process. In other embodiments, an elevated temperature condition (e.g., above 30° C., or at least or above 35, 40, 45, 50, or 60° C., or up to the temperature that the FRP enzyme degrades or suffers a substantial loss in activity) is used during the depolymerization process. In other embodiments, a reduced temperature condition (e.g., below 15° C., or up to or below 10, 5, or 0° C.) is used during the depolymerization process. By being depolymerized, the lignin is broken down into shorter segments compared to its original form. A complete depolymerization results in the conversion of all or a substantial portion (e.g., at least 80, 90, or 95%) of the lignin into at least one or more of the basic building blocks of lignin, i.e., coniferyl, sinapyl, and coumaryl alcohols, and derivatives thereof. A partial depolymerization generally results in less than 80%, or up to 70, 60, 50, 40, 30, 20, 10, 5, or 1% of lignin being converted to primary building blocks, with the rest of the lignin being converted to segments containing two, three, four, or a higher multiplicity (even up to 10, 20, 50, 100, 200, 500, or 1000) of building blocks (e.g., p-hydroxyphenyl, guaiacyl, and syringyl units derived from coumaryl, coniferyl, and sinapyl alcohols, respectively). Since different degrees of lignin depolymerization may be preferred for different applications, the depolymerization conditions can be suitably adjusted to provide an appropriate degree of depolymerization or to favor one or more types of depolymerization products over others.

Since each lignin-containing material has a different distribution and relative amount of each building block, the relative amount of each product produced from depolymerization is very much dependent on the type of lignin-containing material. Other depolymerization products, e.g., aromatic aldehydes, ketones, alcohols, and acids, are generally also produced during the polymerization process, typically in lesser amounts. In embodiments where such other products are not desired, they may be advantageously minimized or eliminated as a product by adjustment of reaction conditions, including appropriate selection of the FRP-bound magnetic nanoparticle or aggregate thereof.

Any of the enzyme-bound magnetic nanoparticle and aggregate compositions described above can be used for the lignin depolymerization process. In particular embodiments, the FRP enzyme used in the lignin depolymerization process is a peroxidase, and particularly, a lignin-degrading peroxidase, such as a lignin peroxidase, versatile peroxidase, manganese peroxidase, or combination thereof (including a core-shell combination thereof). The FRP enzyme may also more particularly be a fungal, microbial, or plant peroxidase. In specific embodiments, the FRP enzyme is a system of two FRP enzymes, such as a fungal peroxidase combined with a glucose oxidase, or a peroxidase and/or oxidase combined with a laccase.

In some embodiments, the lignin depolymerization process is coupled (i.e., integrated) with a downstream process in which depolymerization product produced in the lignin depolymerization process is used for the production of other products. The downstream process may convert lignin depolymerization product into, for example, biofuel or an industrial chemical product, e.g., a polymer, plastic, polymer precursor (monomer), solvent, adhesive, paint, detergent, lubricant, food product, medicinal product, or aroma, or a precursor therefore. The downstream process may alternatively incorporate the lignin depolymerization product into any such end product.

In some embodiments, the lignin depolymerization process is coupled with an upstream process in which lignin-containing material is provided for use in the lignin depolymerization process described herein. The upstream process can be, for example, a paper or pulp producing process, a biomass-to-biofuel process (i.e., where primarily cellulosic material is hydrolyzed and converted to biofuel), or a biomass-to-ethanol fermentation process (i.e., where primarily cellulosic material is hydrolyzed and converted to ethanol).

In another aspect, the invention is directed to a process for removing aromatic contaminants from water (i.e., a water remediation process). In the process, water contaminated with one or more aromatic substances is contacted with any of the enzyme-bound magnetic nanoparticles or aggregates thereof, described above, to cause the aromatic substances to precipitate, i.e., as insoluble material. The precipitated (i.e., sedimented) material is preferably then further separated, such as by centrifugation or settling, and removed from the water by, for example, filtration or decanting. Without being bound by any theory, it is believed that the aromatic substances react with free radicals produced by the enzyme-bound magnetic nanoparticles to produce a polymerized material derived from the aromatic substances. The aromatic contaminant can be any aromatic substance, including those more commonly found in contaminated water. In some embodiments, the aromatic contaminant is benzene, or a benzene derivative, such as a halogenated benzene (e.g., chlorobenzene, dichlorobenzenes, bromobenzenes, or a polychlorinated biphenyl, i.e., PCB), alkylbenzene (e.g., toluene, ethylbenzene, or a xylene), phenolic substance (e.g., phenol, resorcinol, catechol, or a cresol), etherified benzene (e.g., anisole), fused ring compound (e.g., naphthalene, or polyaromatic hydrocarbon), aniline substance (e.g., aniline and N-alkyl or N,N-dialkyl substituted anilines), or benzoic acid compound (e.g., benzoic acid, esters thereof, and hydroxy-substituted derivatives of benzoic acid). In other embodiments, the aromatic contaminant is a heteroaromatic substance, such as furan, pyran, dioxin, thiophene, pyridine, pyrazine, pyrimidine, pyrrole, imidazole, indole, and derivatives thereof.

Any of the enzyme-bound magnetic nanoparticle and aggregate compositions described above can be used for the water remediation process. In particular embodiments, the FRP enzyme used in the water remediation process is horseradish peroxidase, or horseradish peroxidase in combination with an oxidase.

In another aspect, the invention is directed to a process for polymerizing monomers polymerizable by a free-radical mechanism. In the process, one or more types of monomers are reacted with any of the enzyme-bound magnetic nanoparticles or aggregates thereof, described above, to cause the monomers to polymerize. The monomers can be, for example, any of the substances provided above for the water remediation process. In particular embodiments, the monomers are or include vinyl-addition monomers. Upon polymerization, a vinyl-addition polymer is produced. Some examples of such monomers include ethylene, propylene, butadiene, the acrylates and esters thereof, methacrylates and esters thereof, acrylonitriles, vinyl acetate, styrene, divinylbenzene, vinyl fluorides, and vinyl chlorides. In other embodiments, the monomers are phenolic compounds. Upon polymerization, a phenolic resin or polymer is produced. The polymerization process can utilize any of the conditions and apparatuses well known in the art for practicing polymerization reactions, and in particular, free-radical initiated polymerization reactions.

For any of the processes described above, the enzyme-bound magnetic nanoparticles or aggregates thereof can advantageously be captured by magnetic separation in order to prevent contamination of the final product. Moreover, a further advantage of the enzyme-bound magnetic nanoparticles or aggregates thereof described herein is their ability in many cases to retain their activity and re-form after capture, which permits them to be re-used after capture. BNCs showing a loss of activity after several cycles can advantageously be easily extracted and concentrated to their solid form to provide a less wasteful and more efficient process. Metal-coated BNCs can be repurposed by denaturation of the enzymes, sonication, and purification in order to be restored and re-used with fresh functional enzymes. Micro-Bionanocatalysts (Micro-BNC) made of self-assembled BNCs magnetically trapped on a surface are attractive for process applications that use lower intensity magnetic fields. Larger and denser ferromagnetic particles have a higher mass susceptibility compared to mesoporous and low density aggregates of MNPs. MicroBNCs maintain stable, nanosized, and mesoporous structures, which helps to maintain enzyme activity while increasing the overall density and mass susceptibility of the magnetic catalyst. These ultrastructures lend themselves to easier manipulation by external magnetic fields as produced by permanent small magnets and weak field electromagnets. The reaction solution can be purged and replaced while the Micro-BNCs are magnetically trapped, hence allowing for sequential use of the Micro-BNC as long as the enzyme retains process level activities.

Examples have been set forth below for the purpose of illustration and to describe the best mode of the invention at the present time. However, the scope of this invention is not to be in any way limited by the examples set forth herein.

EXAMPLES

Reagents and Instrumentation

The enzymes used in this study were Horseradish Peroxidase (HRP, E.C. 1.11.1.7, type VI-A), Lignin Peroxidase (LiP, E.C. 1.11.1.14), Manganese Peroxidase (MnP; E.C. 1.11.1.13) Versatile Peroxidase (syn. hybrid peroxidase, manganese-lignin peroxidase: VeP EC 1.11.1.16), and laccase. All enzymes used herein were obtained from commercial sources. Horseradish Peroxidase (HRP, E.C. 1.11.1.7, type VI-A) had a Reinheitszahl index (OD $A_{403}/A_{280}$) of around 2.9. High activity forms were obtained by further purification by FPLC (AKTA Explorer, GE Bioscience) using an anionic exchange column (Resource Q, GE Bioscience). Laccase was used without further purification. Protein signal was monitored at 280 nm and the heme signal at 405 nm. For each enzyme, the fractions with a RZ above 1 were pulled together, concentrated and aliquoted. Phenol, homovanillic acid, veratryl alcohol, methoxylphenol, 4-aminoantipyrine (AAP), glucose (the foregoing being at 98% purity), sodium phosphate buffer (PBS) of pH 7.4 and 67 mM, magnetite microsphere powder, manganese sulfate, hydrogen peroxide, $FeCl_3.6H_2O$, and $FeCl_2.4H_2O$, O-phosphoethydiamine, gold tetrachlorohydrate, and malonate and tartrate disodium salts were obtained from commercial sources.

Synthesis of Iron Oxide Magnetic Nanoparticles

Magnetite nanoparticles were synthesized by co-precipitation of $Fe^{2+}$ and $Fe^{3+}$ under alkaline conditions in a bubbling nitrogen atmosphere at 25° C. (M25) or 90° C. (M90). An acidic solution (25 ml) of the iron salts (2 g of $FeCl_2.4H_2O$ and 5.2 g of $FeCl_3.6H_2O$) was added dropwise to NaOH (250 ml, 1.5 M) under constant stirring. Non-oxidizing conditions were achieved by bubbling all solutions with nitrogen for 15 minutes prior to reaction. The instantaneous black precipitation of $Fe_3O_4$ was captured with a neodymium magnet, washed, and neutralized, and kept in distilled water until further use.

Coating of Iron Oxide Magnetic Nanoparticles with Gold

The coating of magnetite nanoparticles was achieved by mild reduction of gold tetrachloroaurate ions onto O-phosphoethydiamine (OPEA) functionalized MNPs under sonication. The coating procedures were performed under nitrogen using a modified rotary evaporator apparatus coupled to a sonic bath. Briefly, 20 mg of MNPs (1 mg/ml) were sonicated for 30 min. OPEA (2 g) was added and allowed to react with the MNPs (40 mL final volume) under sonication and rotation for 2 hours. OPEA-functionalized MNPs were capture with a rare-earth magnet and rinsed 3 times to remove excess OPEA. OPEA-functionalized MNPs were re-suspended in milliQ water with 100 μL of nitric acid (1N) and were agitated for 1H under sonication. Gold tetrachloroaurate (10 up to 30 mg) was added to the OPEA-functionalized MNPs and allowed to react for 30 minutes. The temperature of the sonic bath was raised to 85° C., at which point citric acid/citrate (50:50, 50 mM total, pH5.5) was injected. The gold coating was performed under sonication and fast rotation speed in varying volume (up to 100 mL) and different coating times (up to 60 min). The reaction vessel was placed on ice and the reaction was stopped by adding 5 g of $CaCO_3$. MNP-OPEA-Au nanoparticles were captured magnetically, rinsed four times to remove excess reagents, and stored until further use.

Bionanocatalyst (BNC) Synthesis

All BNCs were formed with either M90 or M25 magnetite nanoparticles, gold-coated or not. The BNCs were formed with either Horseradish peroxidase, Lignin Peroxidase, Manganese Peroxidase or Versatile Peroxidase. Typical BNC synthesis required the MNPs to be initially monodispersed (i.e., individualized and non-aggregated MNPs). MNPs were sonicated in an ultrasonic bath for 20 minutes at room temperature and used immediately to form the BNCs. In preliminary experiments, the effects of buffer composition, buffer strength, and incubation time were investigated to measure their influence on the formation of the BNCs and the activity of the enzymes. Formation of BNCs in water for more than one hour was found to be the most efficient due to the lack of ionic compensative charges; this protocol was implemented for the rest of the study. The final concentration of the peroxidases used for the assays ranged from 0.1 to 10 nM. It was also found that the increased activity was higher for BNCs with 50% or less saturation (per surface area), and therefore, the quantity of MNPs added to the enzymes were adjusted accordingly. Typically, the final concentrations of MNPs in the assay were between 0.5 and 50 $\mu g \cdot ml^{-1}$. A typical ratio is 1 nM of enzyme (HRP) for 2 $\mu g \cdot ml^{-1}$ of MNPs (final concentrations in the assay). The enzyme and the MNPs were added simultaneously and were incubated under constant agitation at 4° C. for at least 12 hours. Typically, the BNCs were formed in stock solution at 5 or 10 times the concentration needed to perform the biochemical reactions. BNCs were finally diluted to the final concentration required in the assay just before the assay. For the synthesis of core/shell poly-enzyme systems BNCs, a core BNC was first formed by reacting the first enzyme (peroxidase or glucose oxidase core enzyme) and sonicated MNPs for 7 hours, then the second enzyme (peroxidase or glucose oxidase=shell enzyme) was added with the appropriate ratio of sonicated MNPs and incubated for a least 7 hours. For random BNCs of glucose oxidase and peroxidase, the sonicated MNPs and enzymes were added simultaneously and incubated for 14 hours.

Micro-Bionanoparticle (Micro-BNC) Synthesis

Micro-BNCs ($\mu$BNCs) were synthesized by reacting formed BNCs with commercial submicrometric magnetite particles. Submicroparticles were suspended in water and sonicated for 20 minutes in an ultrasonic bath. Preformed BNCs and sonicated microparticles were incubated for 6 hours in water under constant agitation and at 4° C. The quantity of submicrometric commercial particles was at least one order of magnitude higher than the quantity of the MPNs forming BNCs on a weight basis. The capture of the BNCs was considered complete when no nanoparticle was detected in the supernatant after magnetic capture with a small magnet.

Characterization of Magnetic Nanoparticles and Mesoporous Aggregates

Magnetic properties were measured using a MPMS XL® (Quantum Design) magnetometer utilizing Superconducting Quantum Interference Device (SQUID) technology. Magnetization hysteresis curves were determined at 300K for external magnetic fields ranging from 40 Oe to 50 kOe. Transmission electron microscopy (TEM) image processing was used to measure the average particle size, size distribution and cluster sizes. TEM measurements were performed with an UHV-STEM microscope (VG, UK). Images were processed using Image Analysis Image J software (NIH, Washington D.C.) and JMicroVision (V1.27). Nanoparticle and cluster size distributions were calculated from a minimum of 1000 particles. Nitrogen adsorption-desorption isotherms were obtained on a Micrometrics ASAP 2020 physisorption instrument. Pore size distributions were calculated from the $N_2$ adsorption isotherm using the Barrett-Joyner-Halenda (BJH) method.

Elucidation of Magnetic Nanoparticles

Figures 2A, 2B:
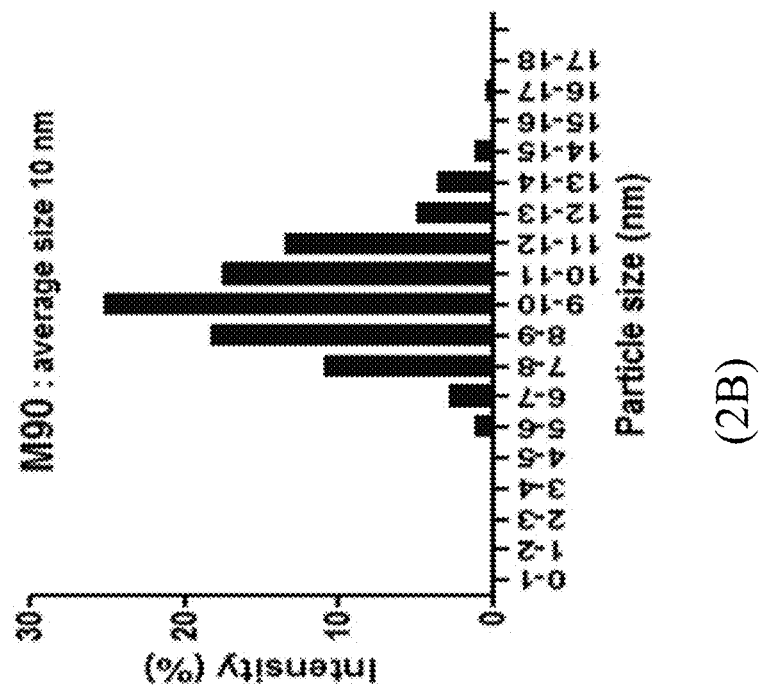
FIGS. 2A, 2B. Particle size distribution plots for magnetite nanoparticles synthesized at 25° C. and 90° C. The nanoparticles synthesized at synthesized at 25° C. and 90° C. have different particle size distributions. M25 nanoparticles (FIG. 2A) have an average size of 8 nm while the average size of M90 nanoparticles (FIG. 2B) is around 10 nm.
Figure 3:
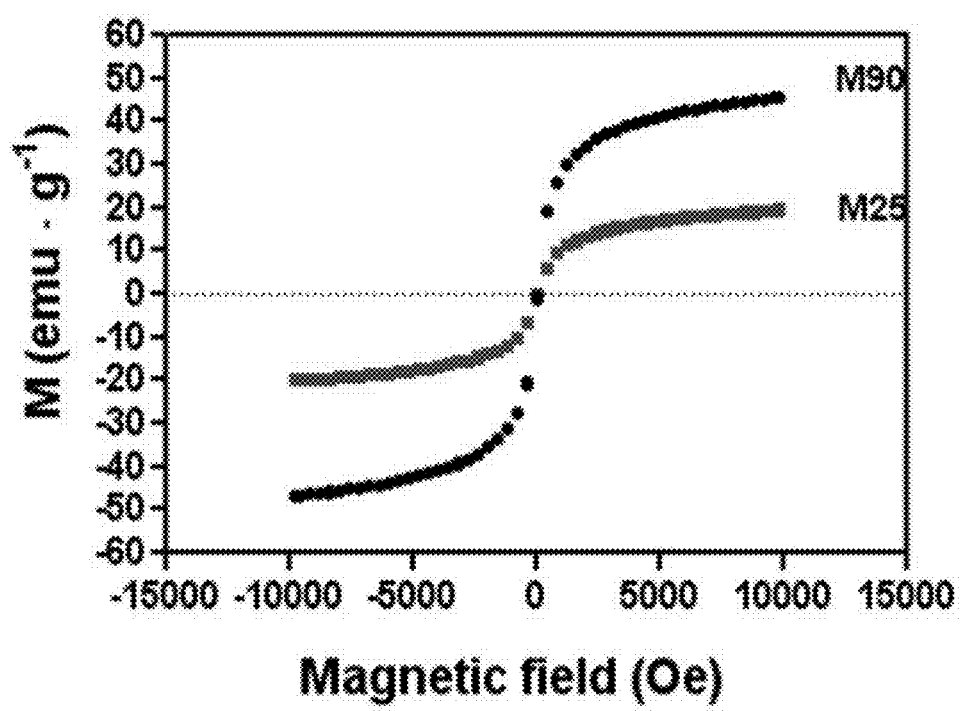
FIG. 3. Magnetization plot for magnetite nanoparticles synthesized at 25° C. and 90° C. The nanoparticles synthesized at 25° C. and 90° C. have a saturated magnetization ($M_s$) of about 20 and 50 emu g$^{-1}$ respectively. Both have negligible remanent magnetization ($M_r$) making them superparamagnetic. Their superparamagnetic properties allow for fairly monodispersed magnetic nanoparticles in solution after sonication.
Figure 7:
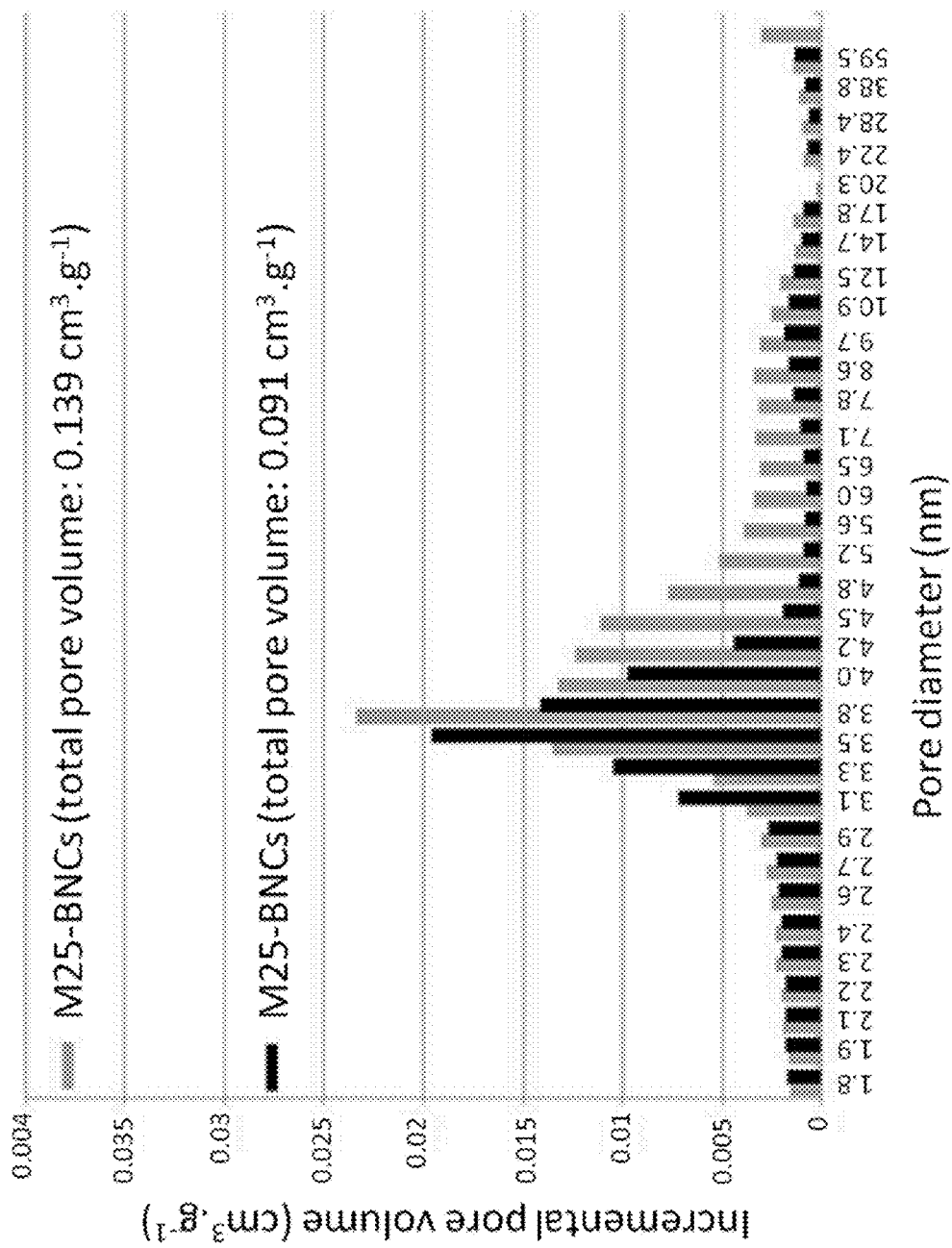
FIG. 7. Pore size distribution plot for M25 magnetic nanoparticles and M25-BNC enzyme clusters. M25-BNCs are mesoporous with pores below 50 nm in diameter. Smaller nanoparticles form aggregates with smaller pore size. The pore size distribution is affected by the presence of the enzyme, and the total pore volume is lower than the total pore volume of the M25 MNPs clusters, thus indicating that the enzymes occupy the mesoporous space.
Figure 8:
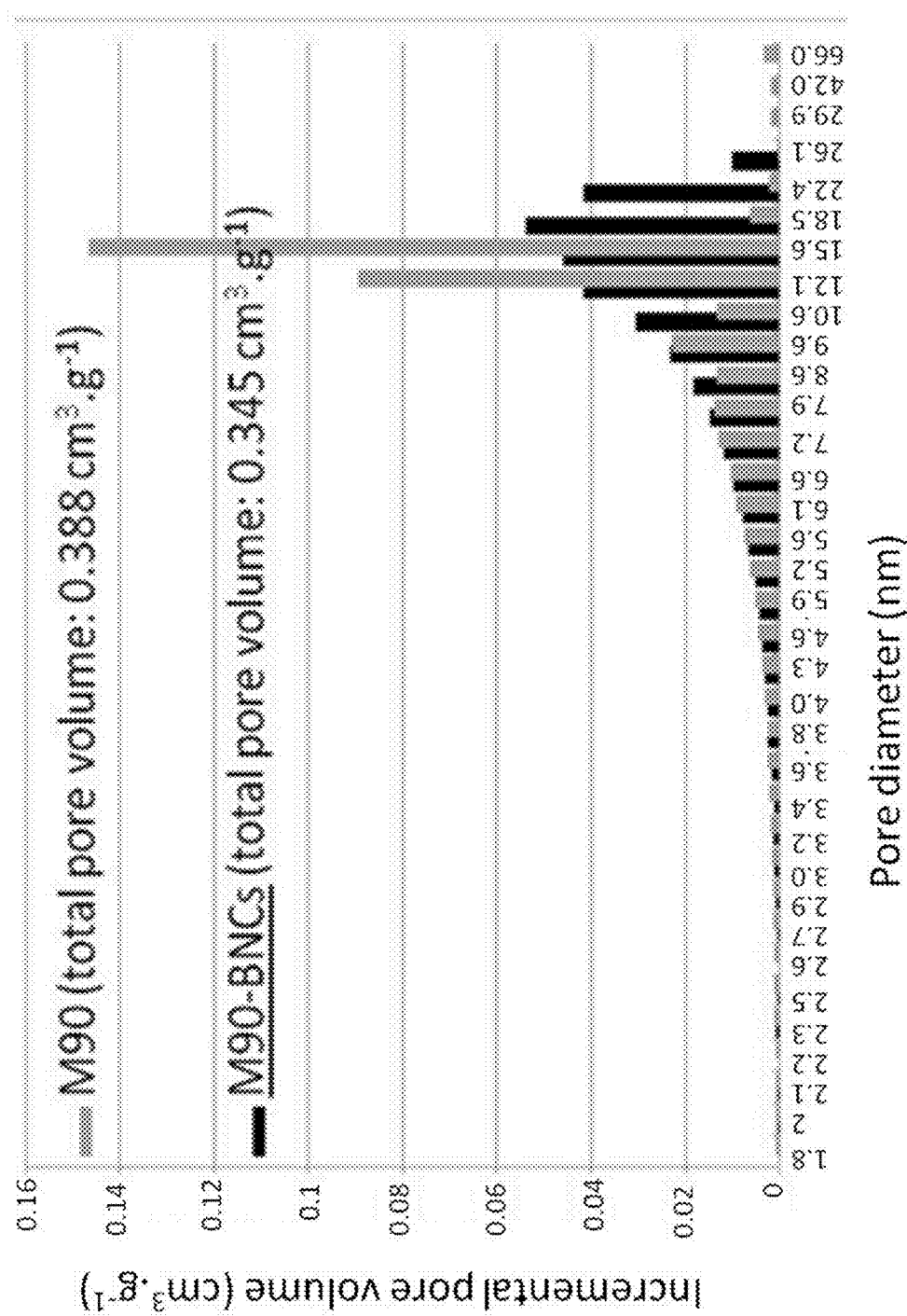
FIG. 8. Pore size distribution plot for M90 magnetic nanoparticles and M90-BNC enzyme clusters. The cluster formed by the aggregation of M90 MNPs are mesoporous, with pores below 50 nm in diameter. Larger nanoparticles form larger aggregates with larger pore size. The pore size distribution is affected by the presence of the enzyme, and the total pore volume is lower than the total pore volume of the M90 MNPs clusters, thus indicating that the enzymes occupy the mesoporous space.

The X-ray diffraction pattern shown in FIG. 1 confirms that the MNPs are made of magnetite. The synthesis described above uses low-cost reagents and can be easily tailored in size (FIGS. 2A, 2B) and magnetic field (FIG. 3). As shown by FIGS. 2A and 2B, M90 had a more uniform size distribution with an average size of 10 nm (±1), while M25 had a broader size range with an average size of 8 nm with particles as small as 5 nm. As shown by FIG. 3, both MNPs had overall negligible remanent magnetization ($M_R$), which is indicative of superparamagnetism. As shown by FIGS. 4A-4C and 5A, at the concentration of magnetite used for the assays, M25 MNPs were mostly monodisperse with small clusters and free nanoparticles, whereas M90 formed large clusters of 100 nm in diameter on average. As shown by FIGS. 7 and 8, the total pore volume was 0.39 $cm^3 \cdot g^{-1}$ and 0.14 $cm^3 \cdot g^{-1}$ for M90 and M25, respectively. The average density of the clusters when corrected for the porosity was found to be $\rho_{M25}$ of 3.03 $g \cdot cm^{-3}$ and $\rho_{M90}$ 1.72 $g \cdot cm^{-3}$.

Quantification of Entrapped Enzyme Using Horseradish Peroxidase (HRP)

Quantification of denatured HRP with magnetite nanoparticles was achieved by using a high-throughput FTIR spectrometer (HTS-XT-Vertex70, Bruker, Germany). Fifty microliters of BNC slurry was dried out on a transmittance silicon 96-well plate at 60° C. under vacuum for one hour and left to dry under vacuum at room temperature overnight. The spectra were recorded between 4,000 and 400 $cm^{-1}$, 32 scans, and the background was recorded before each sample. Samples were analyzed in triplicates; on-plate standards of magnetite and magnetite plus HRP were used to measure the concentration of proteins and nanoparticles in each sample. Adsorption isotherms parameters were extracted by fitting the quadratic form of the Langmuir equation using a least-square fitting method using Matlab software:

$$Q = \frac{Q_m K_a C^*}{1 + K_a C^*} \quad (1)$$

In Formula (1) above, Q is the adsorbed enzyme on the surface ($nmol \cdot m^{-2}$), $C^*$ is the initial enzyme concentration ($nmol \cdot m^{-2}$), $Q_m$ is the maximum amount of bound enzyme ($nmol \cdot m^{-2}$), and $K_a$ is the adsorption constant ($m^2 \cdot mol^{-1}$). These parameters were applied in the kinetic experiments to directly calculate the bound fraction of HRP at equilibrium from the initial concentration of HRP.

Characterization of Peroxidase Enzyme Activities

Phenol/AAP assay: The peroxidase activity of native HRP and BNC was monitored using the chromogenic phenol/AAP assay that generates phenoxy radicals that readily react with aminopyrene to form the pink-colored quinoneimine dye. An automated plate-reader (Synergy 4, Biotek) with injection capabilities and temperature-controlled chamber was used to record the absorbance of the solution at 510 nm in 96-well plates (4 replicates) for 30 minutes. The standard reagent concentrations of the assay (200 $\mu$l) were 80 mM and 13 mM for phenol and AAP respectively. Different buffer and buffer strength were tested. Hydrogen peroxide was injected to initiate the reaction with concentrations ranging between $10^{-7}$ M and 1 M. The background contribution due to the nanoparticles and substrates was subtracted. For HRP, the quantity of free enzymes was calculated by difference with the bound amount estimated with the Langmuir adsorption parameters as the quantity of free enzyme could not be estimated directly because of low HRP concentrations and high background from the MNPs. For each run, a velocity standard curve was established for the free enzyme and used to correct for the contribution of the free enzyme to the total activity when not all enzyme molecules were bound. The velocities (V) and specific activity, A ($mmol_{product} \cdot s^{-1} \cdot mmol_{enzyme}^{-1}$) were calculated based on the initial rates of the reaction.

Fungal Peroxidase activities using model substrates: Colorimetric assays were performed in 96-well UV transparent microplates (Falcon) using standardized colorimetric protocols in sodium tartrate or malonate (LiP: Veratryl alcohol, pH 3, 310 nm; MnP: 2,6 dimethoxyphenol, pH 4.5, 468 nm and 270 nm for the formation of $Mn^{3+}$-organic acid complex; VeP: veratryl alcohol or 2,6 methoxyphenol, pH 4.5, 310 nm, 468 nm, 270 nm).

Peroxidase activities with Homovanillic acid (HVA) fluorescent assay: A fluorescent assay was developed to measure the initial rate of the peroxidase kinetics. HVA free radicals can polymerize to form a fluorescent dimer ($\lambda_{ex}$ 310 nm, $\lambda_{em}$ 405 nm). An automated sequential procedure was implemented on a Biotek Plate Reader with syringe mixing capabilities to perform the dilution of the reaction initiators ($H_2O_2$ or glucose). A chemically-reacted stock of fluorescent dimer was synthesized by reacting HVA (10 mM) with sodium ferrocyanide (15 mM) and ammonium hydroxide (15 mM) and was used as quantitative standards in the buffers used for the enzymatic reactions. All the reactions were performed in triplicate and data expressed in relative fluorescent units (mRFU).

Lignin depolymerization assays: A Kraft lignin depolymerization assay was conducted using HRP, LiP, VeP and MnP, and BNCs thereof. MnP and VeP assays were performed in presence of manganese. Assays were performed in triplicates in sodium tartrate or sodium malonate buffer, pH 5.5. Kraft lignin slurries (10 mg/ml) were incubated for 1 or 4 hours then filtered through 0.2 μm pore membrane filter to remove particulates. The UV-Vis spectra of the solutions were acquired with a Biotek Plate Reader. The release of aromatic molecules from lignin depolymerization was monitored at 280 and 310 nm. The spectra were corrected for the background.

Phenol polymerization assays: The phenol removal assay was a two-step procedure. The first step consisted in forming polyphenols with Horseradish Peroxidase in 1 mM PBS buffer. Reaction volumes were fixed at 2 ml or 10 mL. The final concentration of phenol was fixed at 1 mM and HRP at 30 nM. The BNCs formed with M90 were varying in enzyme-to-nanoparticles ratio. The second step was the precipitation of these polyphenols by adding sodium chloride (500 mM). The samples were centrifuged at 12,000 g for 20 minutes and the supernatant collected. The soluble phenol in solution was measured at 280 nm with a Biotek Plate Reader.

Kinetic Parameters

The specific activity, A ($mmol_{product} \cdot s^{-1} \cdot mmol_{HRP}^{-1}$), was calculated as the ratio $V/mmol_{HRP}$ using the extinction of the respective products formed at the wavelength monitored. A $H_2O_2$ substrate inhibition model derived from the ping-pong bi-bi 2 substrate inhibition model was used to extract the kinetic parameter of the reaction with a least-square fitting method using GraphPad Prism (La Jolla, Calif., USA). The modified equation from the model is:

$$V = \frac{V_{max}[H_2O_2]}{K_m + [H_2O_2](1 + [H_2O_2]/K_i)} \quad (2)$$

In Formula (2), $V_{max}$ is the maximum enzyme velocity ($mmol \cdot s^{-1}$), the maximum rate the enzyme reaction can achieve, expressed in the same units as V, $K_m$ is the Michaelis-Menten constant (mM), $K_i$ is the inhibition constant for $H_2O_2$ (mM). $k_{cat}$ ($s^{-1}$) was calculated from $V_{max}$ and the total quantity of bound HRP.

Formation, Characterization and Activities of Magnetite BNCs Formed with HRP

Figure 4A:
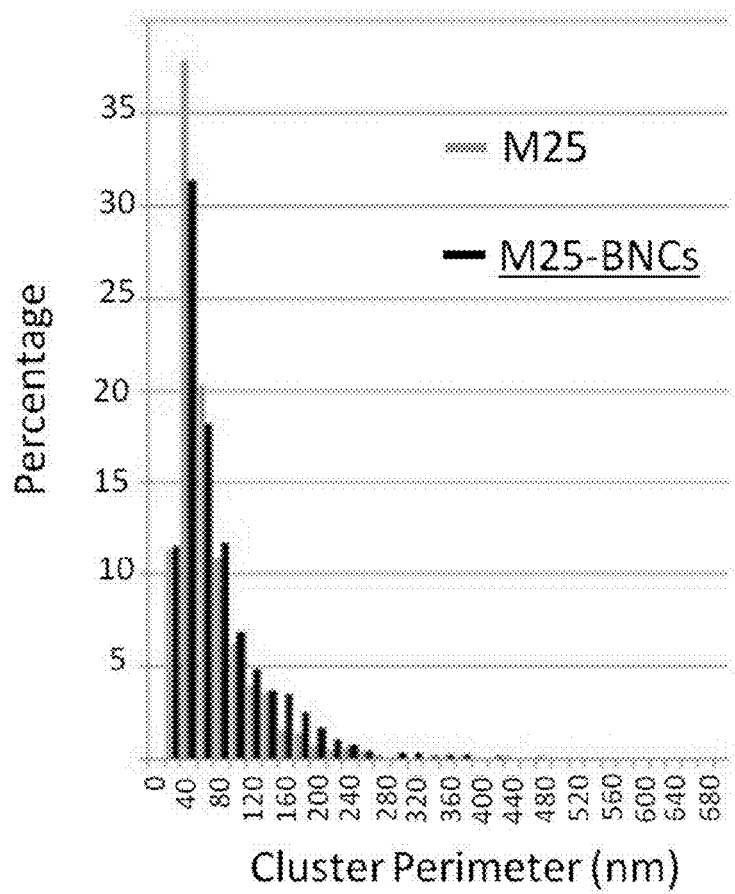
FIGS. 4A-4C. Particle size distribution plot for M25 and M25-BNC (FIG. 4A) and micrographs of M25 (FIG. 4B) and M25-BNC (FIG. 4C). The size of the M25 nanoparticle aggregates increases when the enzyme (HRP) is added to the initially monodispersed magnetic nanoparticles. The presence of the enzyme increases the overall diameter of the clusters.
Figures 4B, 4C:
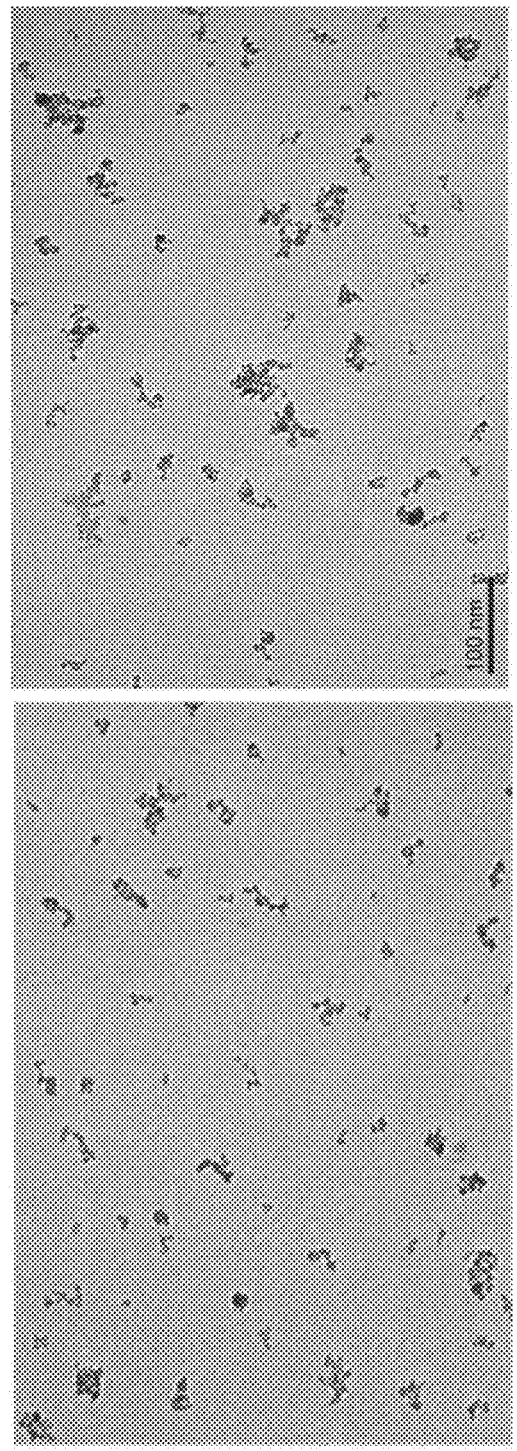
Figure 5A:
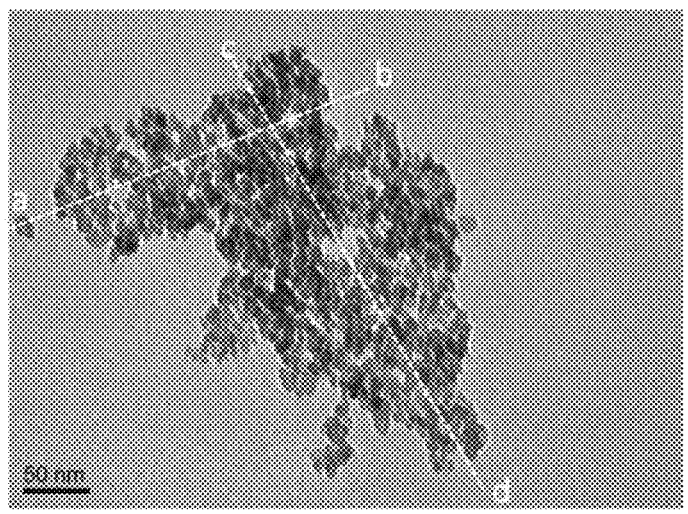
FIGS. 5A-5G. Micrograph of M90 nanoparticle clusters (FIG. 5A) and corresponding size plots (FIGS. 5B, 5C), micrograph of M90-BNC nanoparticle clusters (FIG. 5D) and corresponding size plots (FIGS. 5E, 5F), and size distribution plot comparing M90 and M90-BNC clusters (FIG. 5G).
Figure 5B:
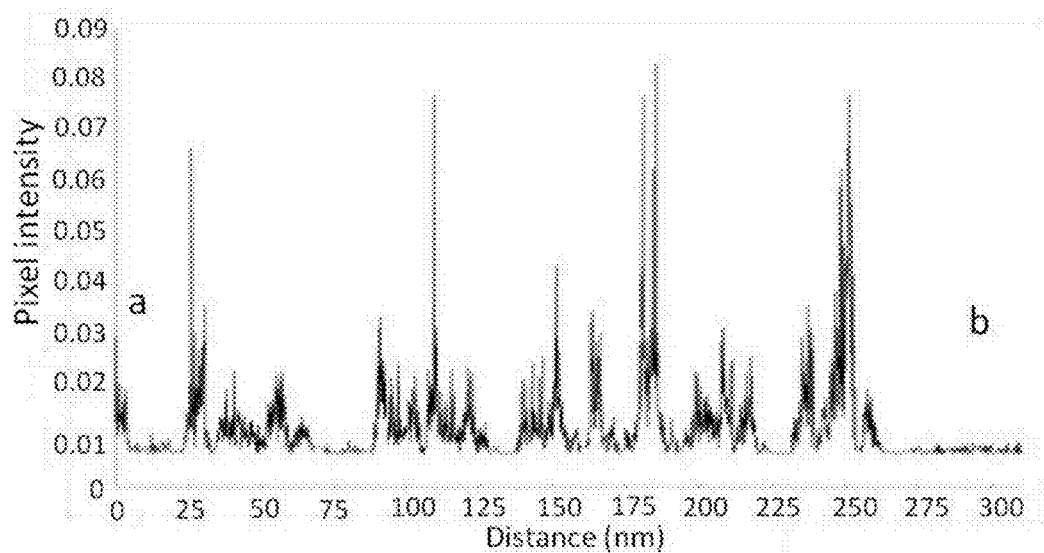
Figure 5C:
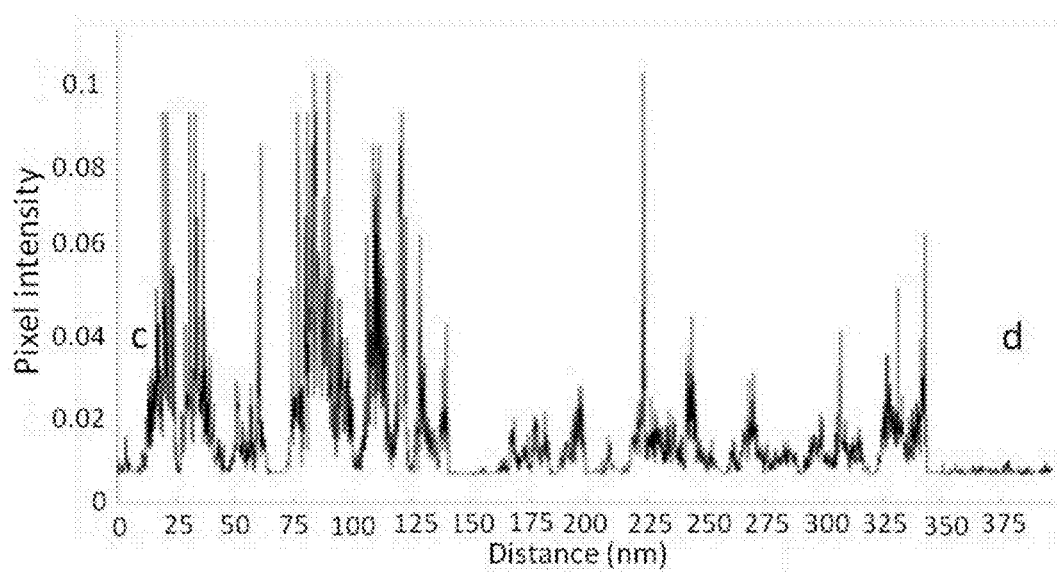
Figure 5D:
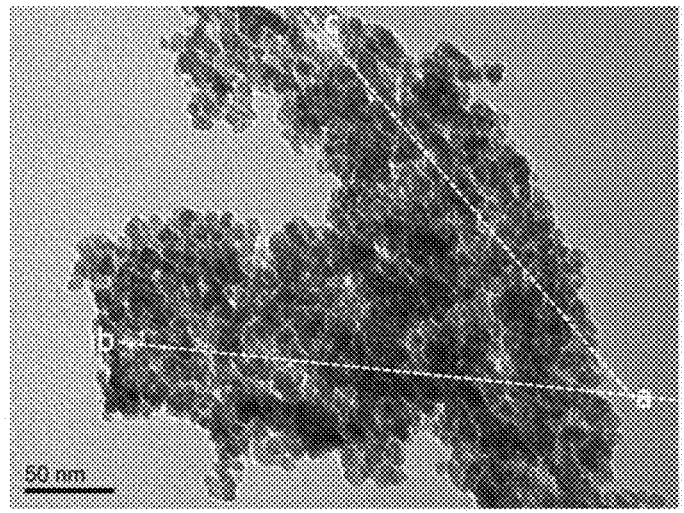
Figure 5E:
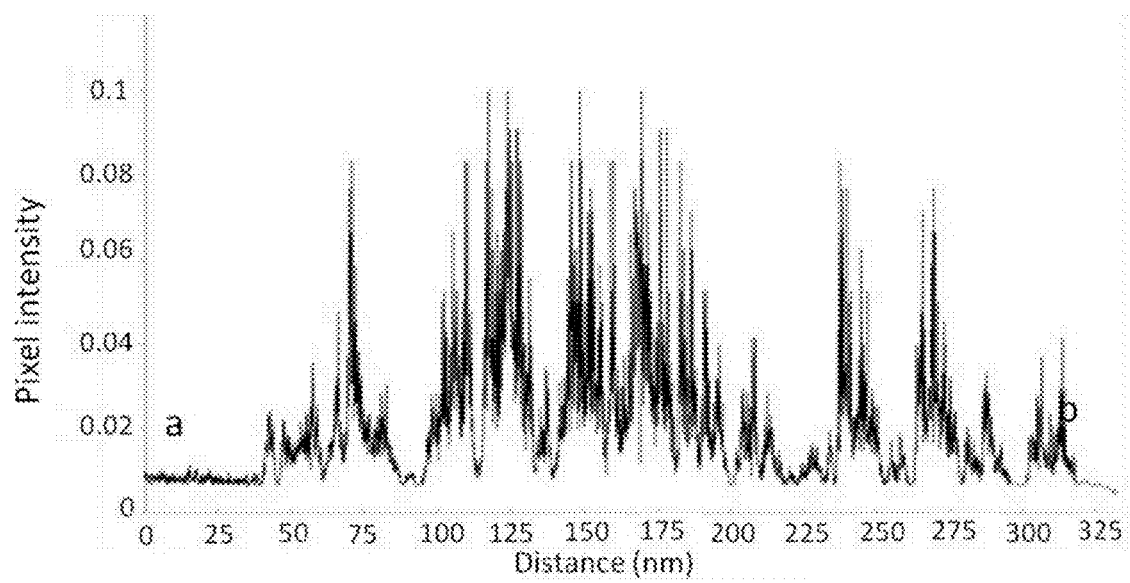
Figure 5F:
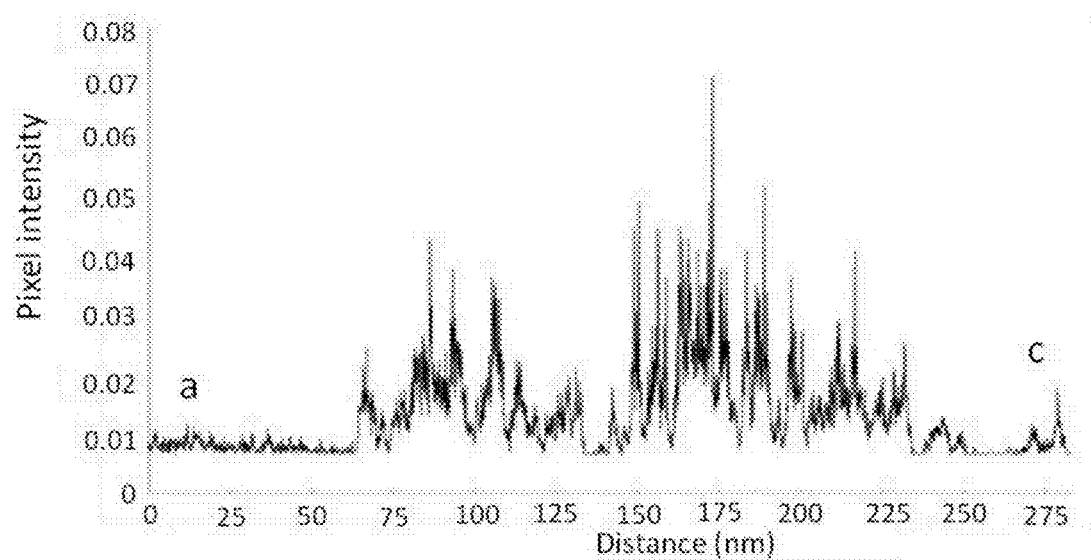
Figure 5G:
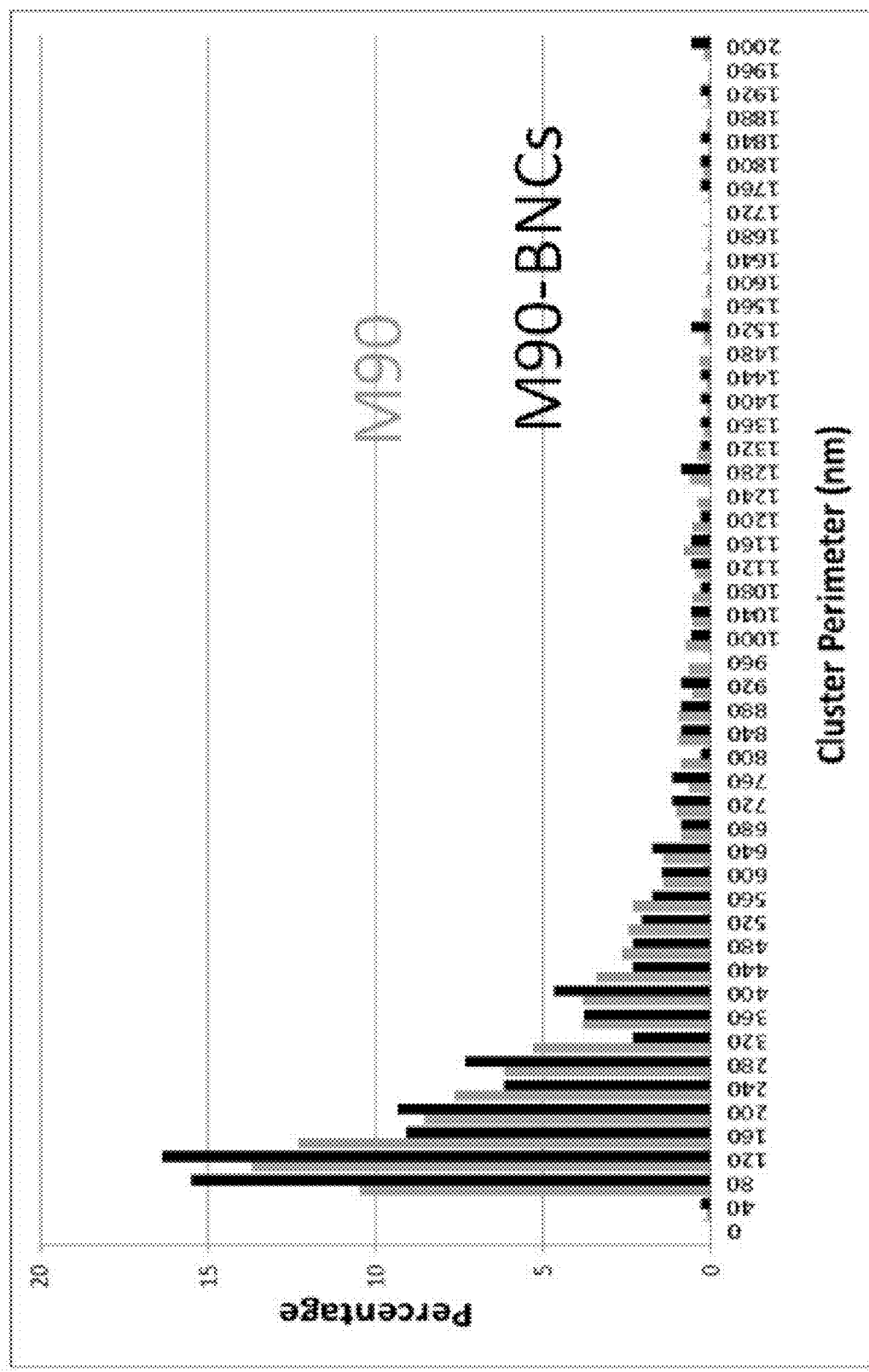
Figure 6:
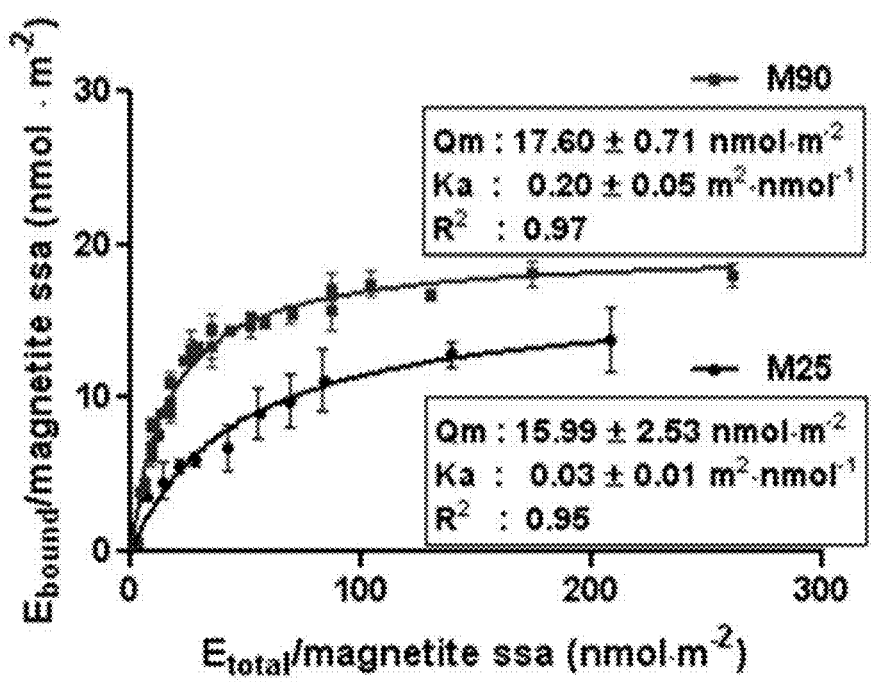
FIG. 6. Graph plotting the isotherms of the quantity of entrapped enzyme per quantity of enzyme in solution per available surface area of MNPs. The quantity of enzymes entrapped in the clusters (standardized per surface area of the MNPs) was measured for M90 and M25. The aggregate formed with M90 MNPs contains more enzyme than the one formed with M25 MNPs for an initial amount of enzyme in solution. Below 10 nmol·m$^{-2}$ of enzyme in solution, 100% of the enzymes are entrapped in the clusters formed with M90, while about 50% are trapped in the M25 clusters.

The entrapping of enzyme molecules in the MNP clusters was confirmed by the overall increase in size of the BNC clusters (FIGS. 4A and 5G). Both M25 MNPs (FIG. 4 B) and M25-BCNs (FIG. 4 C) had small cluster sizes although M25-BNCs size was slightly increased and had bigger clusters. A comparison of M90 MNPs (FIG. 5A) and M90-BNCs (FIG. 5D) demonstrates that the increase in size of the nanoparticle aggregates was higher for M90 than for M25. Moreover, the aggregates of M90 BNCs (FIGS. 5E and 5F) had a higher density, i.e. made of more MNPS and more compacted MNPs, than the aggregates of M90 alone (FIGS. 5B and 5C). The entrapping of enzyme molecules in the MNP clusters was further confirmed by the difference in HRP adsorption behavior between M25 and M90 (FIG. 6). Both BNCs were mesoporous (FIGS. 7 and 8) with pores below 50 nm. M90-BNCs had a higher total pore volume and higher average pore size than M25-BNCs. The differences in the formation of the complexes was consequently attributed to the ultrastructure of the MNPs clusters resulting from differences in magnetization of the nanoparticles and resulting mesoporosity of the clusters. In particular, M90-BNC self-assembly appears to result from a dual mechanism of surface adsorption and molecular entrapment in the mesoporous aggregates.

Figure 11A:
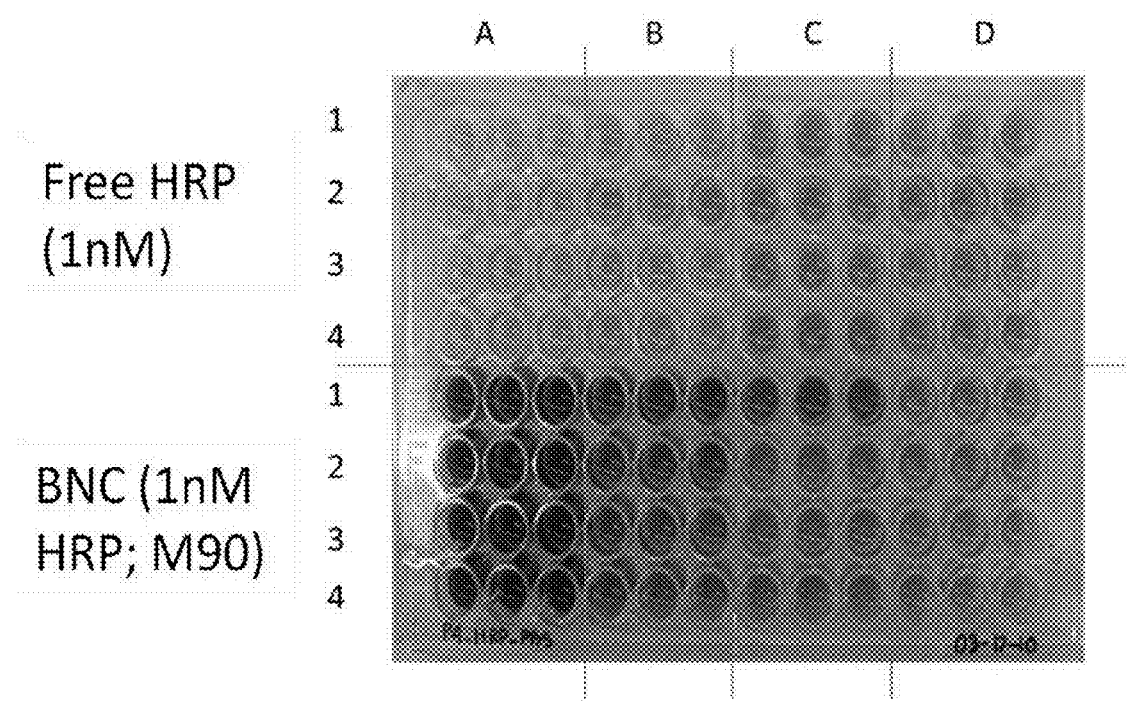
Figure 12A:
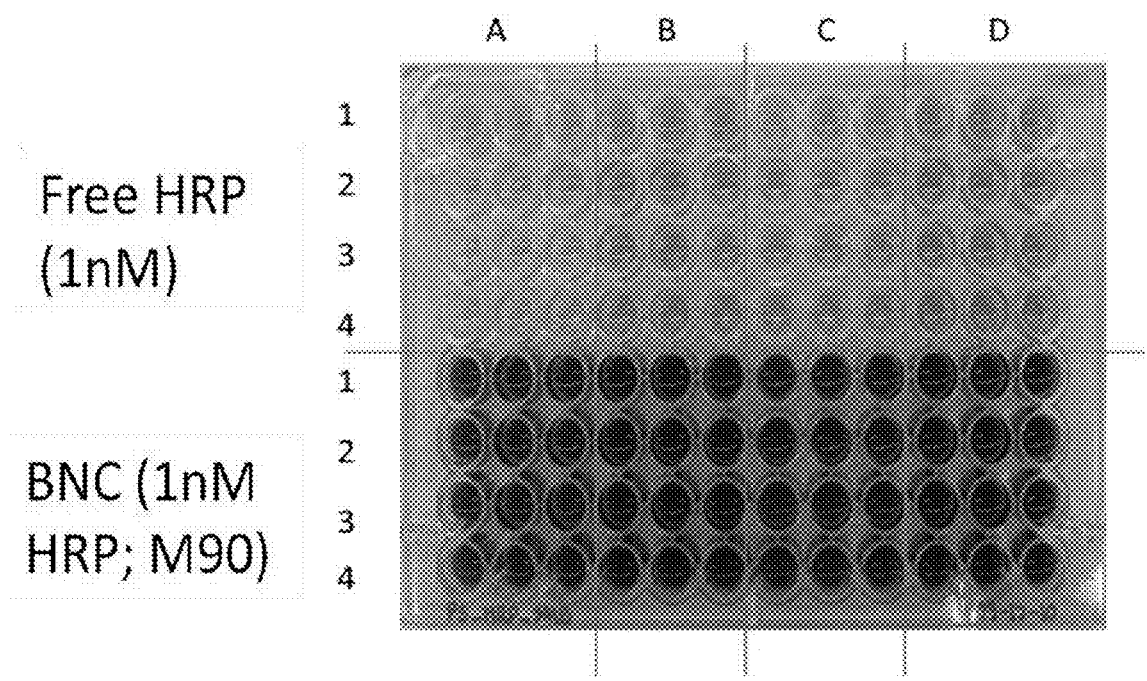
Figure 13A:
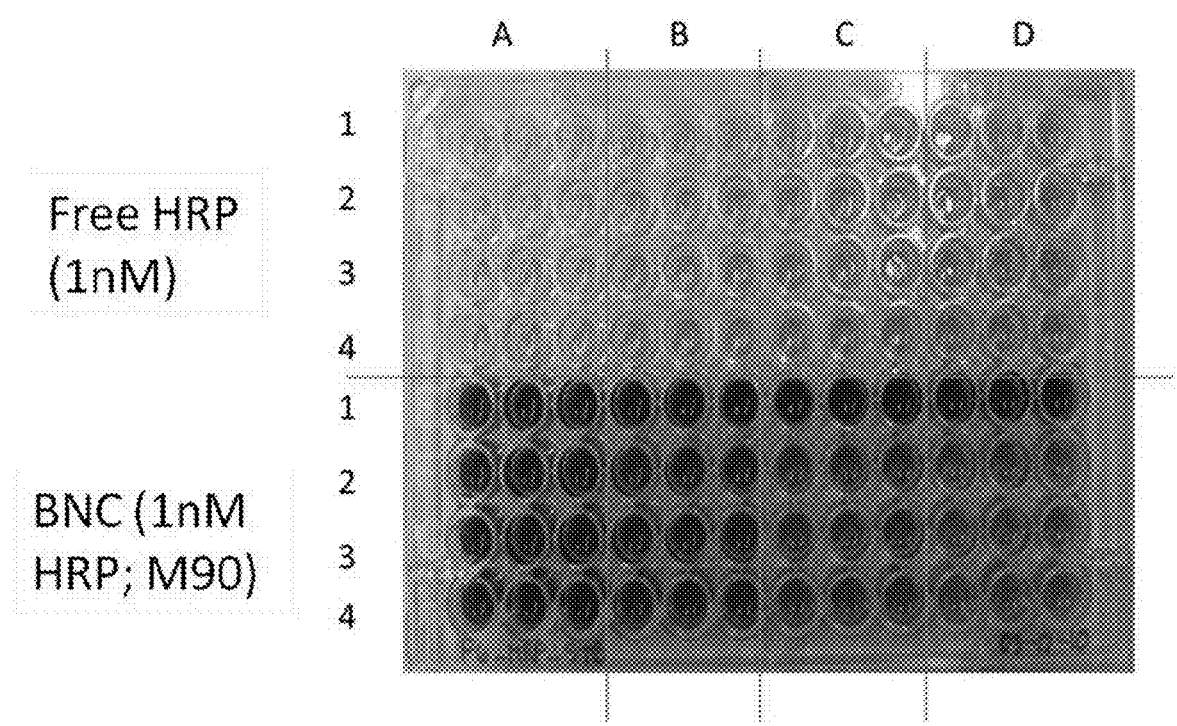

M90 had a higher $K_a$, thus indicating a higher affinity for the enzyme compared to M25 (FIG. 6). In quantifying the entrapped enzymes, it was found that less than 50% of the total HRP loaded could bind to M25 to form the M25-BNC complex when 1 nM HRP and 4 μg·ml$^{-1}$ magnetite particles were used, while 100% of the enzyme was captured in the case of M90. As shown by FIGS. 11A, 11B, 12A, 12B, and 13, the increased in activities varied as the BNCs were formed in different conditions. The most active BNCs were formed in ultrapure water at pH 6.5, which implies the presence of Fe—OH$^{2+}$ cationic species on the nanoparticle surfaces. At this pH and in the absence of any other compensating charges, a large surface of the HRP molecule remains negatively charged, which can allow for the formation of complexes with magnetite via electrostatic interactions. When the BNCs formed in PBS were tested (FIG. 11A), the increase in activity was lower than for the BNCs formed in water (FIG. 11B). BNCs formed in PBS had the lowest increase in activity of all. When the BNCs formed in malonate were tested (FIG. 12A), the increase in activity was in the same range or lower than for the BNCs formed in water (FIG. 11B). When the BNCs formed in tartrate were tested (FIG. 13A), the increase in activity was lower than for the BNCs formed in water (FIG. 13B). As also shown by FIGS. 11B, 12B and 13B, only BNCs formed in water consistently showed a higher increase in activity than BNCs formed in other ionic buffers, even at higher concentration of salts, when used in other buffers for the assays.

Figures 9A, 9B:
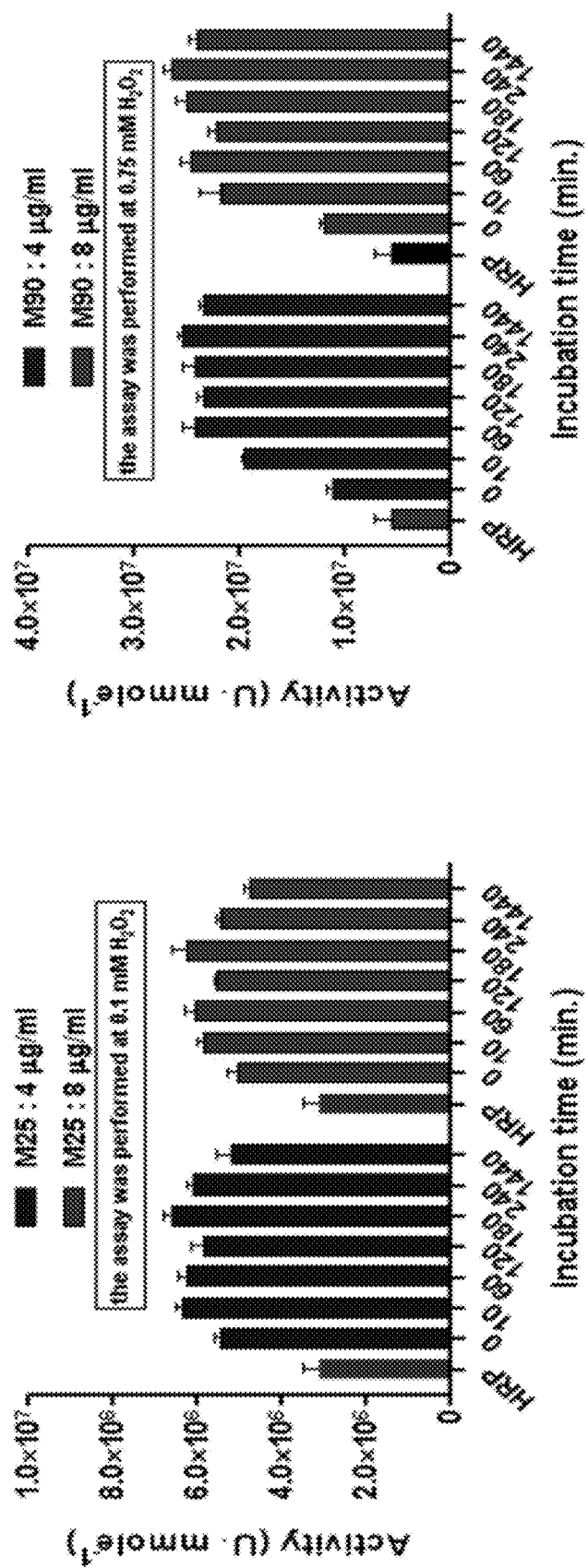
FIGS. 9A, 9B. Graphs plotting activity (Phenol AAP assay, in U·mmole$^{-1}$) as a function of incubation time for M25-BNC (FIG. 9A) and for M90-BNC (FIG. 9B) at 4 µg/mL and 8 µg/mL concentrations to determine the effect of incubation time on the activity of the BNC.
Figure 10:
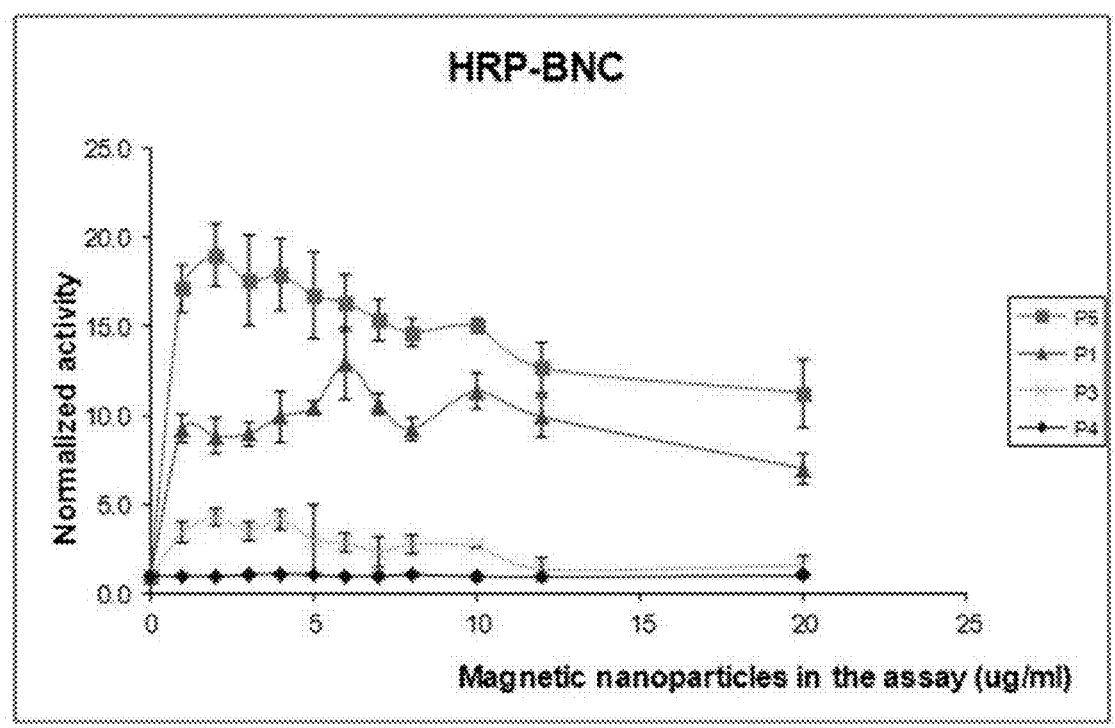
FIG. 10. Graph plotting normalized activity as a function of concentration of magnetic nanoparticles (HRP-BNC) used in the assay (in µg/mL) to determine effect of incubation time on the activity of the HRP-BNC. P5 protocol: 3% (vol/vol) premix from diluted 1:1 (vol/vol) solutions of HRP+nanoparticles (M90); P1 protocol: 3% (vol/vol) premix from high concentration stock solution of HRP and M90; P3 protocol: 14% (vol/vol) premix 1:1 (vol/vol) suspensions of HRP+nanoparticles; P4 protocol: no premix, add enzymes and particles separately in the assay mix. Protocols P5 and P1 are comparing the way to mix the enzyme and the nanoparticles (M90) to form BNCs. The effect of BNC concentration in the assay is shown by P3 and P5. For comparison, P4 shows the effect of no incubation at all. The self-assembly depends on the concentration of MNPs in the premix (enzyme+MNPs). High concentration of MNPs leads to lower activities due to over-agglomeration.
Figure 14:
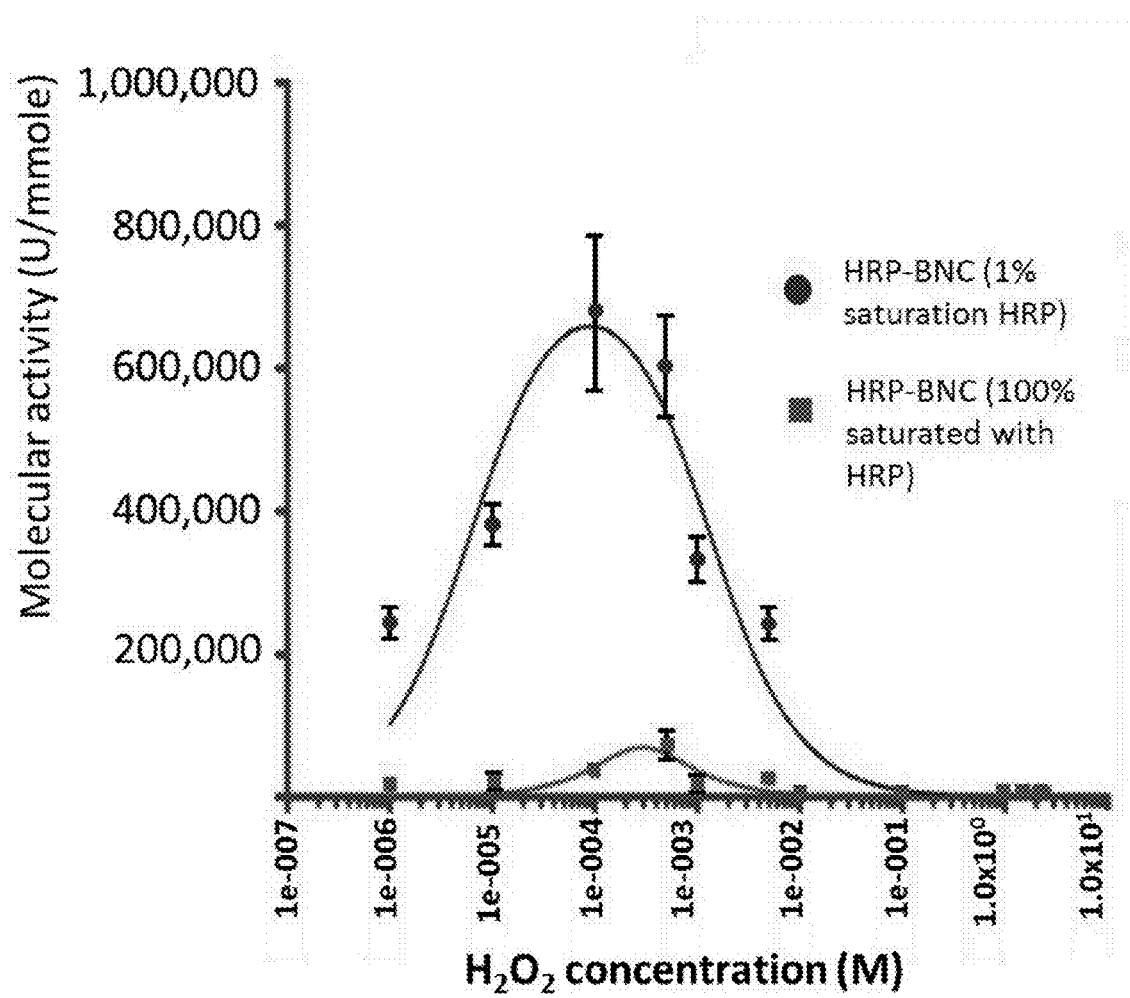
FIG. 14. Graph plotting molecular activity (Phenol/AAP assay, in U·mmole$^{-1}$) as a function of peroxide concentration for HRP-BNC nanoparticle aggregates to determine effect of enzyme saturation of the mesoporous spaces. Surprisingly, the MNP aggregates saturated with enzyme did not increase the enzyme activity, whereas BNCs with a non-saturated amount of enzyme showed increased activities.
Figure 15:
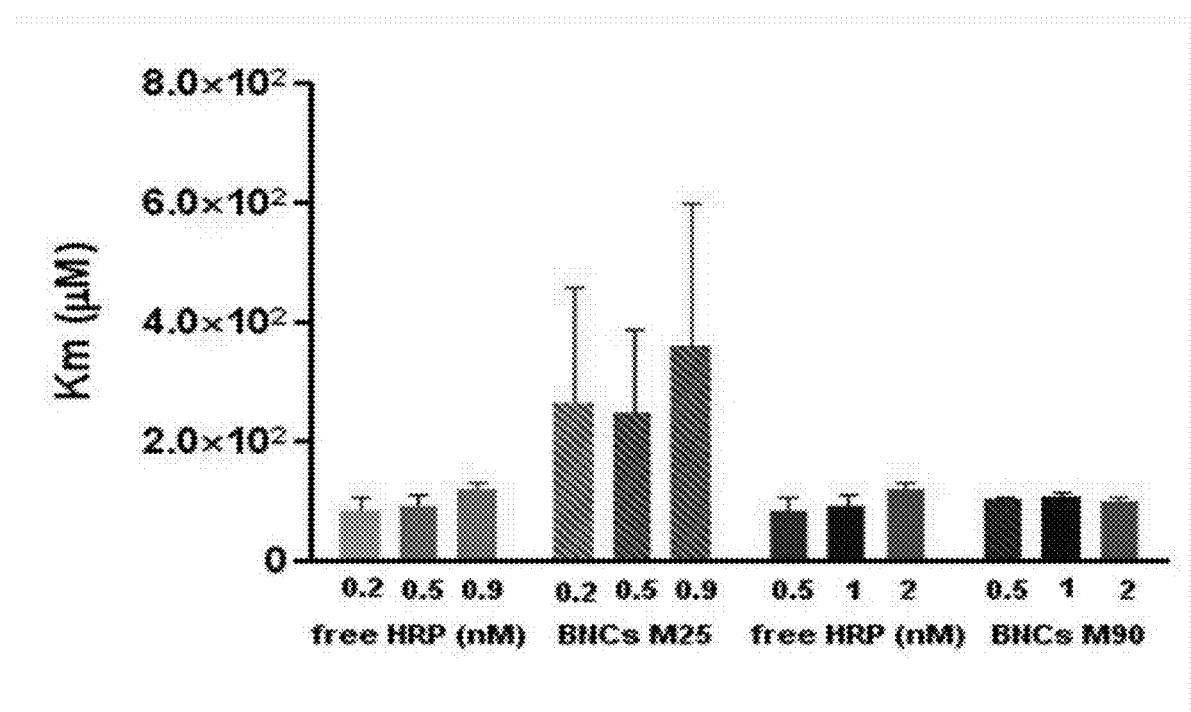
FIG. 15. Graph plotting $K_m$ kinetic constant as a function of nanoparticle concentration for free HRP, M25 BNC and M90 BNC in order to determine substrate affinity constant for free HRP and BNCs formed with M25 and M90. The $K_m$ kinetic constant estimated was by fitting the velocities plots of the HRP-BNCs. The affinity constant was increased in the case of BNCs formed with M25, thus indicating a better utilization of peroxide. No difference in $K_m$ was observed in the case of enzymes entrapped in the mesoporous space of the BNCs formed with M90.
Figure 16:
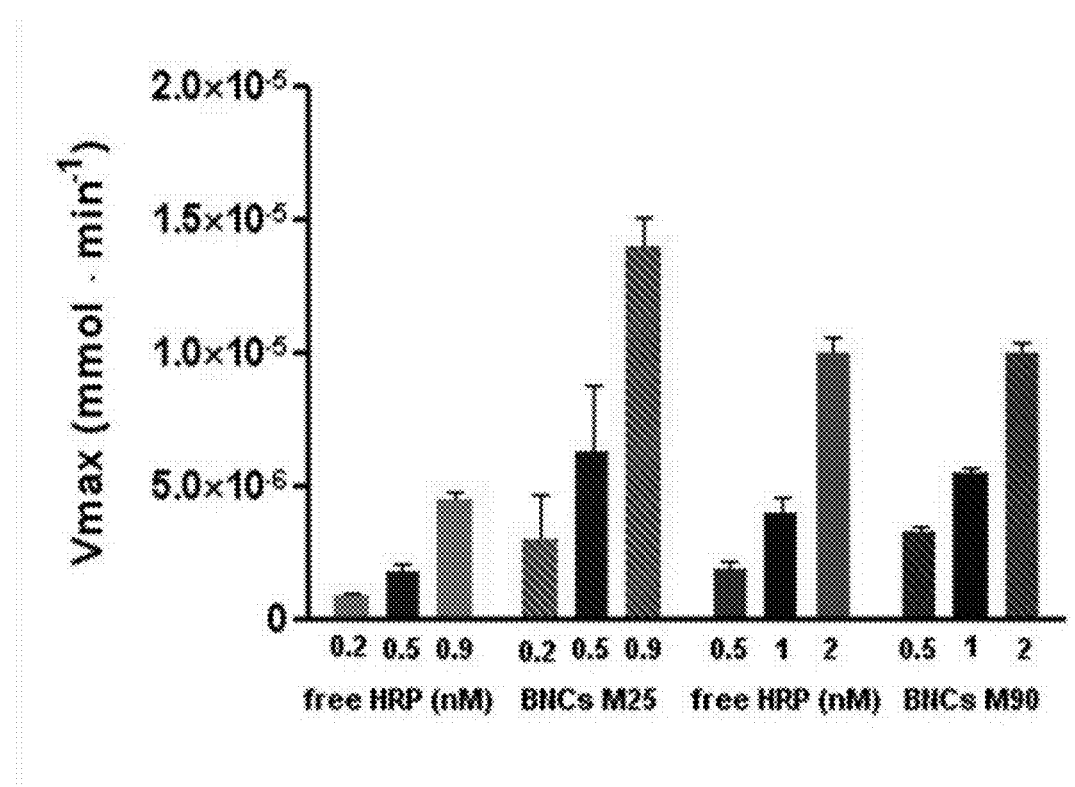
FIG. 16. Graph plotting $V_{max}$ as a function of nanoparticle concentration for free HRP, M25 BNC and M90 BNC in order to determine maximal velocity constant for free HRP and BNCs formed with M25 and M90. The $V_{max}$ kinetic constant was estimated by fitting the velocities plots of the HRP-BNCs. The maximal velocity was increased in the case of BNCs formed with M25 compared to the $V_{max}$ of the free enzymes, thus indicating a better utilization of peroxide. No difference in $V_{max}$ was observed in the case of the enzymes entrapped in the mesoporous space of the BNCs formed with M90 and their free counterpart.
Figure 17:
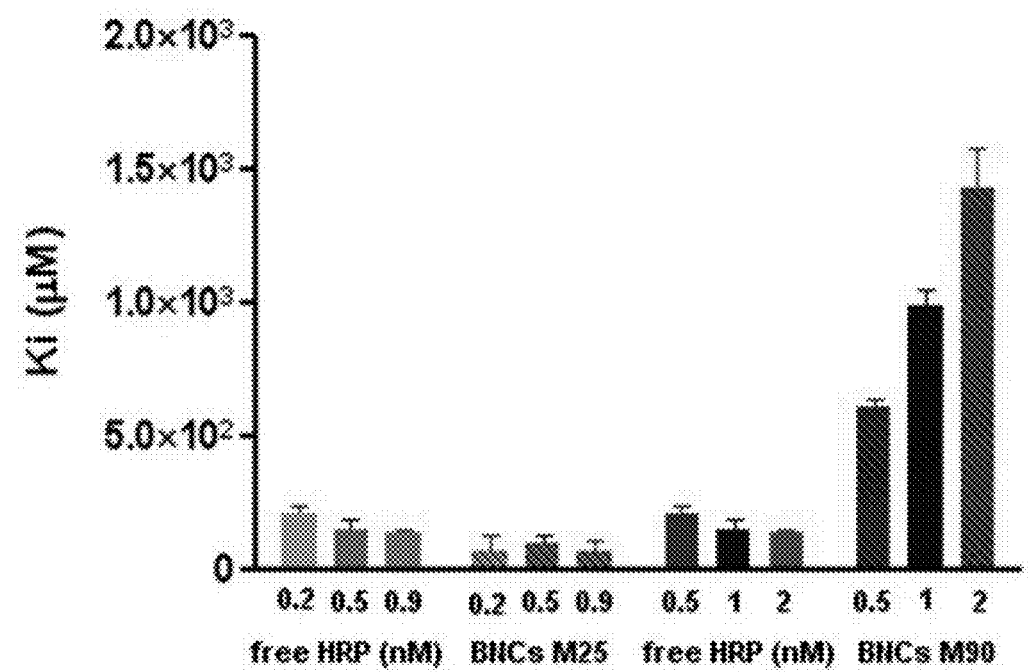
FIG. 17. Graph plotting $K_i$ kinetic constant as a function of nanoparticle concentration for free HRP, M25 BNC and M90 BNC in order to determine inhibition constants for free HRP and BNCs formed with M25 and M90. The $K_i$ kinetic constant was estimated by fitting the velocities plots of the BNCs made with HRP. The substrate inhibition constant was drastically increased in the case of BNCs formed with M90, thus indicating a better protection of the enzyme against inhibition when entrapped in the mesoporous space of the BNCs. Inhibition of M25-BNC was in the same range, if not lower, than for the free enzymes.
Figure 18:
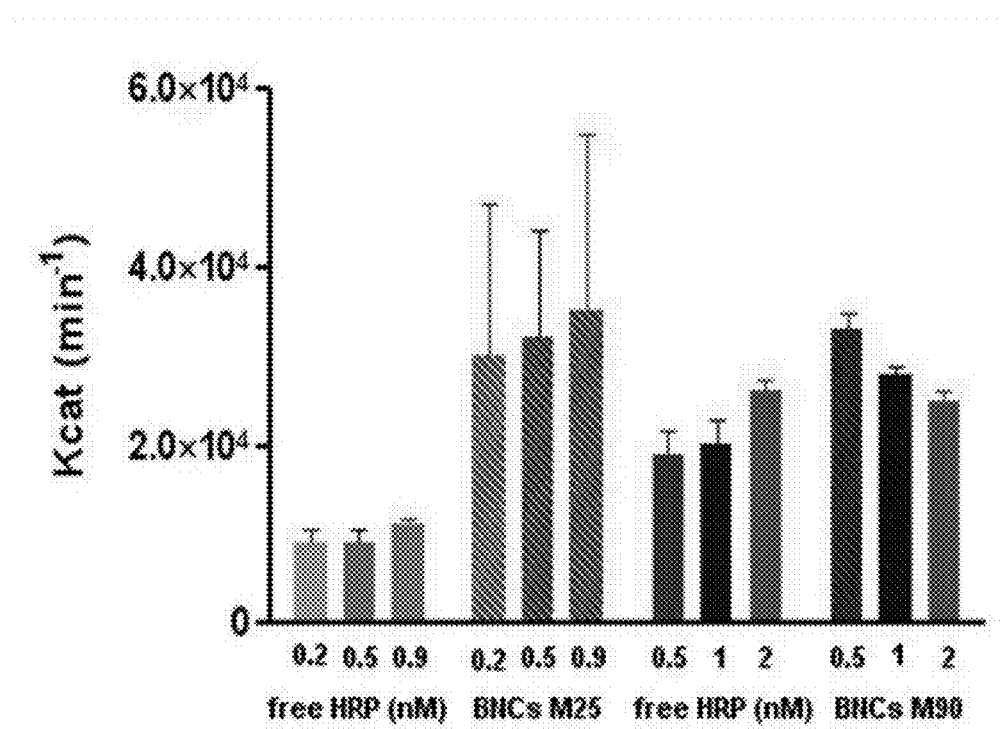
FIG. 18. Graph plotting $k_{cat}$ kinetic constant as a function of nanoparticle concentration for free HRP, M25 BNC and M90 BNC in order to determine turnover constant for free HRP and BNCs formed with M25 and M90. The $k_{cat}$ kinetic constant was estimated by fitting the velocities plots of the BNCs made with HRP. The turnover constant was drastically increased in the case of BNCs formed with M25 compared to the free enzyme, thus indicating a better utilization of the substrates. The $k_{cat}$ of M90-BNCs was also increased for lower concentrations of enzymes.
Figures 19A, 19B:
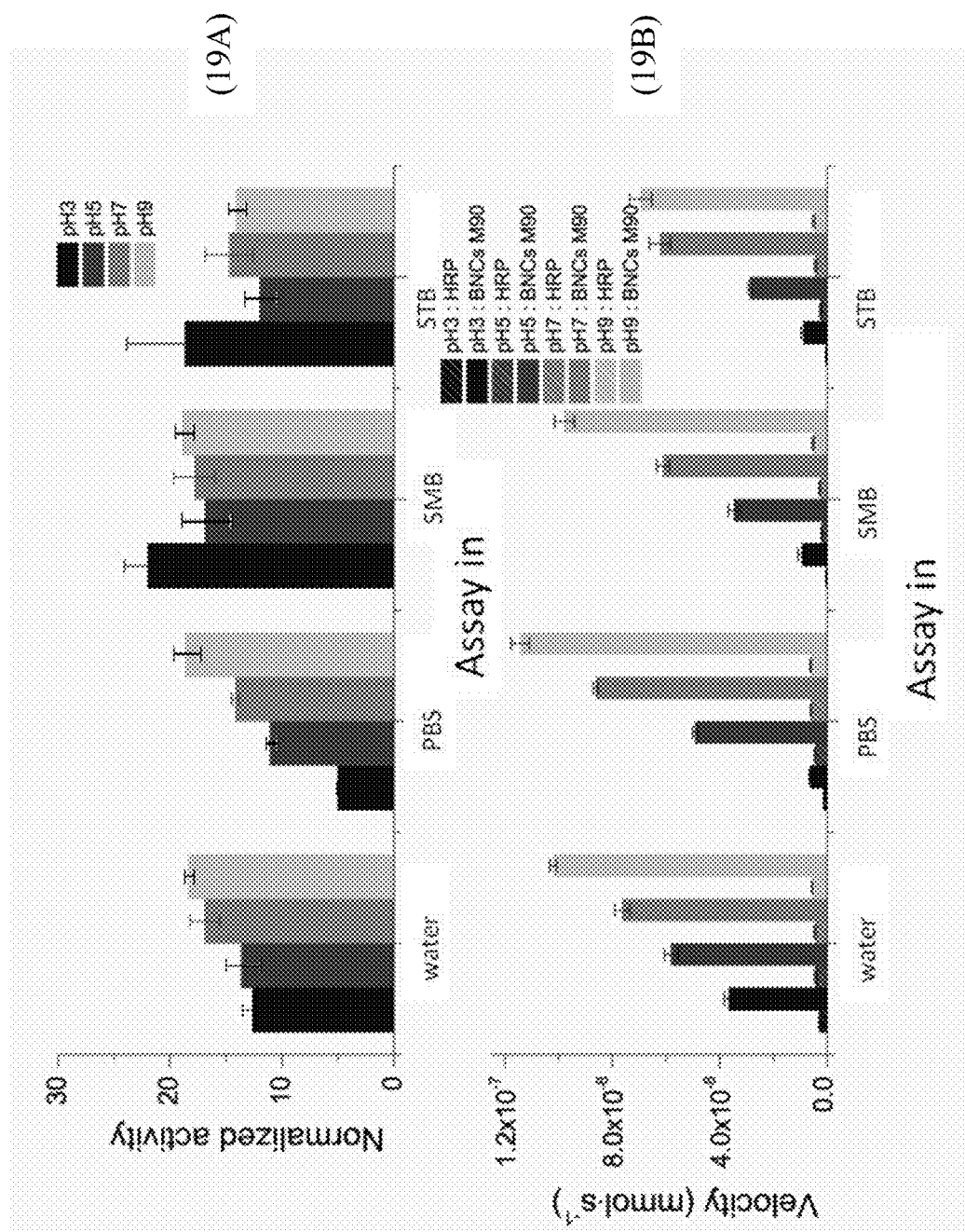
FIGS. 19A, 19B. Graphs plotting normalized activity (phenol/AAP assay) as a function of assay buffer and pH (FIG. 19A) and graphs plotting velocity as a function of assay buffer in pH (FIG. 19B). BNCs were formed with HRP (1 nM) and M90 MNPs (4 µg/ml) in water, and were tested at different pH conditions with the phenol/AAP assay at 5 mM peroxide and 5 mM buffers. The increase in activity was observed for all buffers and at all pHs.
Figures 20A, 20B:
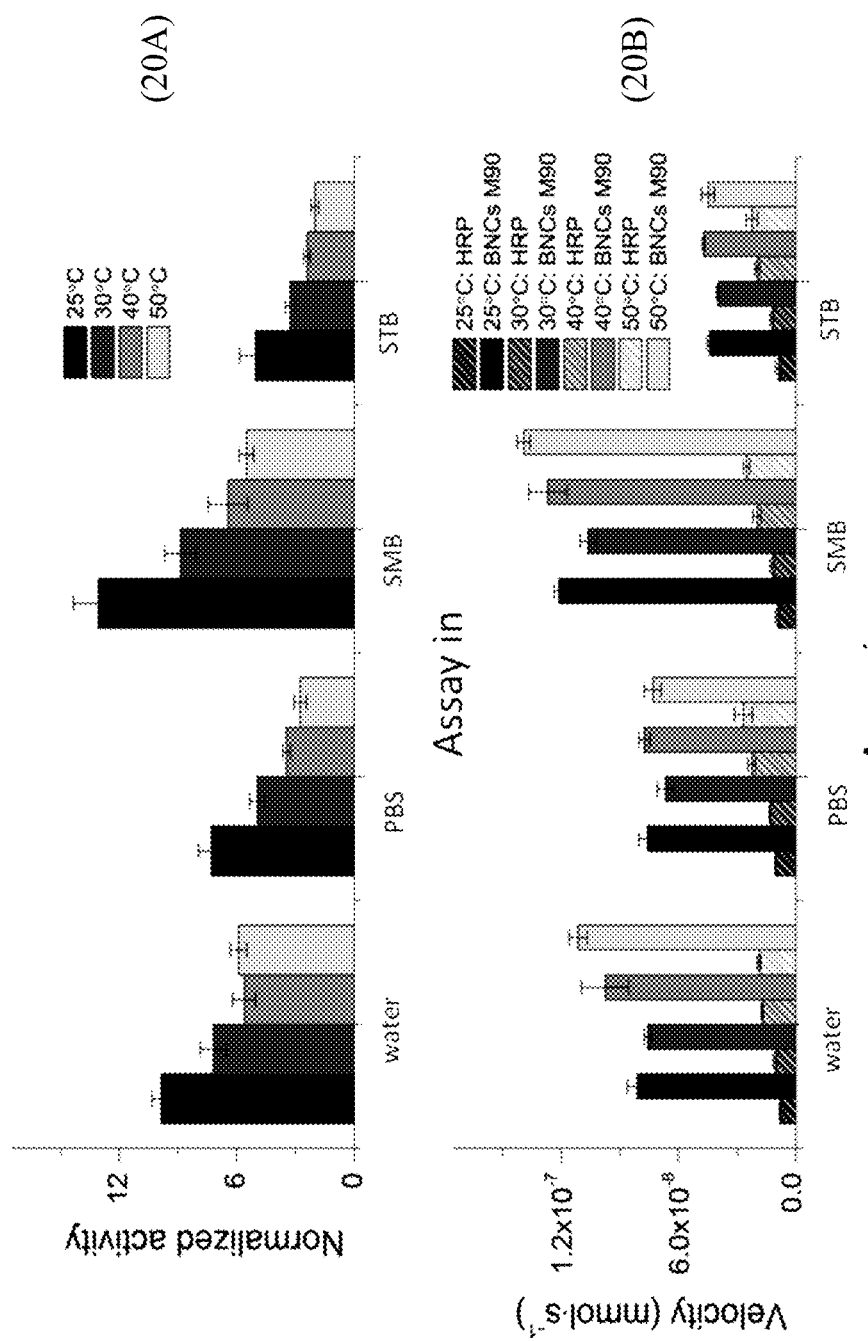
FIGS. 20A, 20B. Graphs plotting normalized activity as a function of assay buffer and pH (FIG. 20A) and graphs plotting velocity as a function of assay buffer in pH (FIG. 20B) for the phenol/AAP assay. BNCs were formed with HRP (1 nM) and M90 MNPs (4 µg/ml) in water, and were tested at different temperature conditions with the phenol/AAP assay at 5 mM peroxide and 3 mM buffers. The increase in activity was observed for all buffers and at all temperatures, and was maximal at 25° C. The observed increase compared to the free enzyme appears to be the result of the lower velocity of the free enzyme, thus indicating that the BNCs are more efficient at lower temperature.

Temporal free-radical concentrations were measured using the phenol/AAP assay, and these measurements were used to calculate the normalized activities of the BNC. Normalized activities were calculated as the ratio of the BNC activity divided by the free enzyme activity at the same concentration. For M90-BNC, the maximum activity compared to the free enzyme was reached after 1 hour of pre-incubation. The increase of normalized activity was shown to be stable over 24 hours. As shown by FIGS. 9A and 9B, M25-BNC reached the maximum increased activity after 10 minutes of incubation. These results clearly demonstrate that the increased activity is only due to the immobilized enzyme and not just the presence of the MNPs in solution. Moreover, as shown by FIG. 10, the results also demonstrate that the association of HRP with magnetite nanoparticles of different size, magnetism, and ratio yield different complexes with different specific activity. As shown by FIG. 14, the saturation of the BNCs with the maximal amount of entrapped enzyme consistently resulted in a decrease in activities.

Initial reaction velocities were used to estimate $K_m$, $V_{max}$, $K_i$ and $k_{cat}$, as further demonstrated by the plots shown in FIGS. 15-18, respectively. The $V_{max}$ of M25 or M90 MNPs was several orders of magnitude lower than those of the free HRP and BNCs. The turnover rates, $k_{cat}$, were very consistent with free HRP, M25-BNC, and M90-BNC datasets. BNC formed with M25 and M90 both had a higher $K_m$. M25-BNC had $V_{max}$ and $k_{cat}$ two to three times greater than the free enzyme at the same concentration. Also, the $k_{cat}$ of M25-BNCs increased with the fraction of bound enzyme while the $K_i$ was in the same range than the free HRP. At 0.5 nM of bound enzyme, the efficiencies of the MNPs, as estimated by $k_{cat}/K_m$, were $6.75 \times 10^3$ and $5.5 \times 10^3$ s$^{-1}$mM$^{-1}$ for M25-BNCs and M90-BNCs, respectively. These kinetic results are consistent with the trends observed with the reaction velocities. M90-BNC had a $K_i$ about 10 times greater than the free HRP, while its $V_{max}$ was similar. The higher $K_i$ for M90 indicated the lower extent of substrate inhibition from $H_2O_2$ compared to the free enzyme and M25-BNCs.

The M90-BNC activities were further investigated for different buffer, pH, and temperature (FIGS. 19A, 19B, 20A, and 20B). A similar increase in M90-BNC activity was also observed in inorganic and organic buffers and across the range of temperature tested. The BNCs were found to be more efficient at lower temperatures than the HRP alone, as the free enzyme had higher velocities at higher temperature. The M90-BNCS were found to be pH sensitive, with the velocities increasing with pH, while the normalized activities were pH dependent in inorganic buffers. No significant effect of pH was observed with the organic acid buffers.

BNCs Activities for other Enzyme Systems

Figure 21:
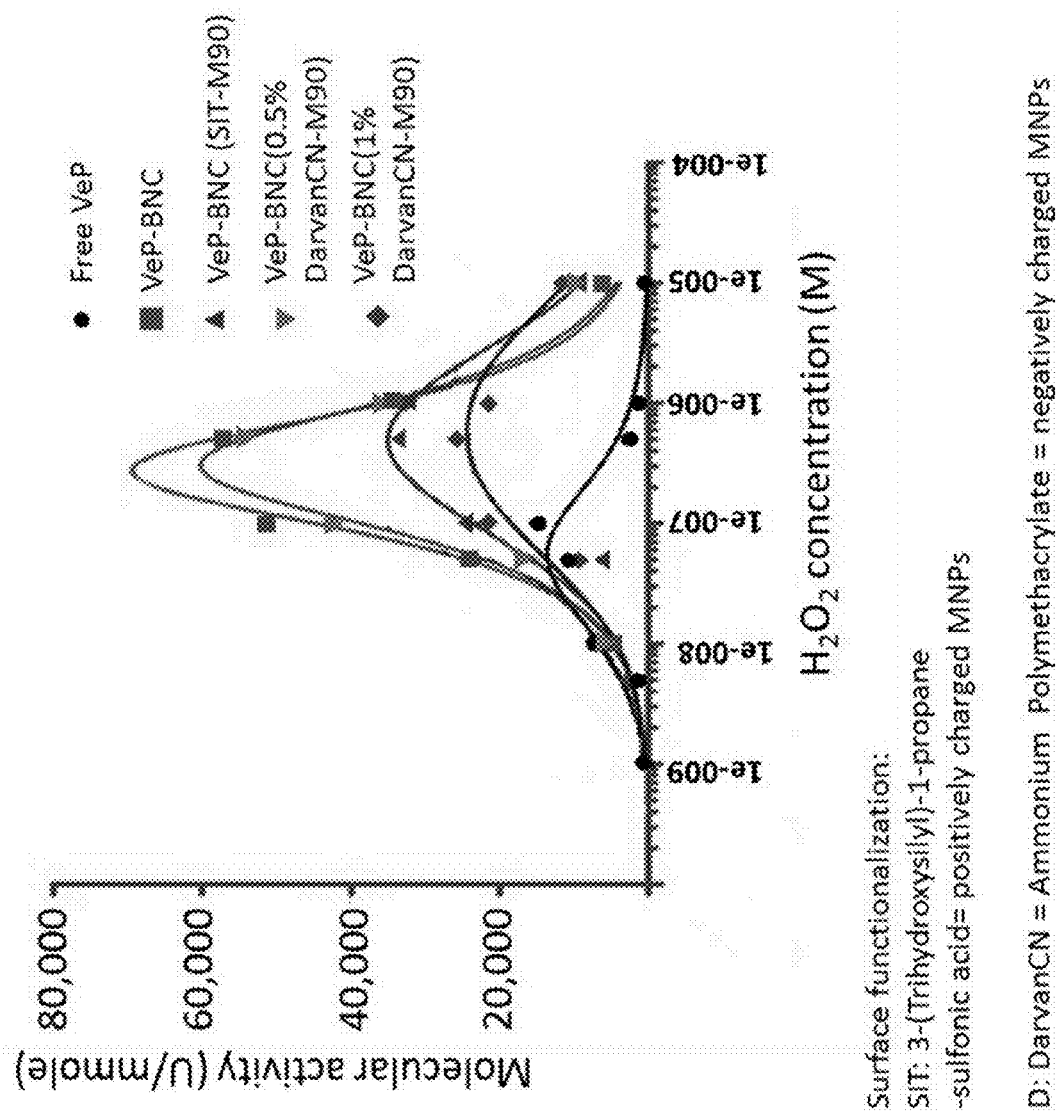
FIG. 21. Graph plotting molecular activity (phenol/AAP assay in U·mmole$^{-1}$) as a function of peroxide concentration (M) for BNCs formed with versatile peroxidase and M90 and functionalized M90. The BNCs were formed with Versatile Peroxidase (VeP: commercial form, no additional purification) and assayed with the Phenol/AAP (no manganese). M90-MNPs were functionalized with organic polymers to modify the charge of the surfaces. All BNCs showed increased activity compared to the free VeP. The maximal activity was observed for non-modified BNCs.

Activities of Versatile Peroxidase-BNCs: BNCs were formed with Versatile Peroxidase enzyme (FIG. 21). As shown by the activity plot in FIG. 21, the maximal activities were observed for BNCs formed with M90. Surface modifications with organic polymers only resulted in a modest increase in activities but lower inhibition from hydrogen peroxide.

Figure 22:
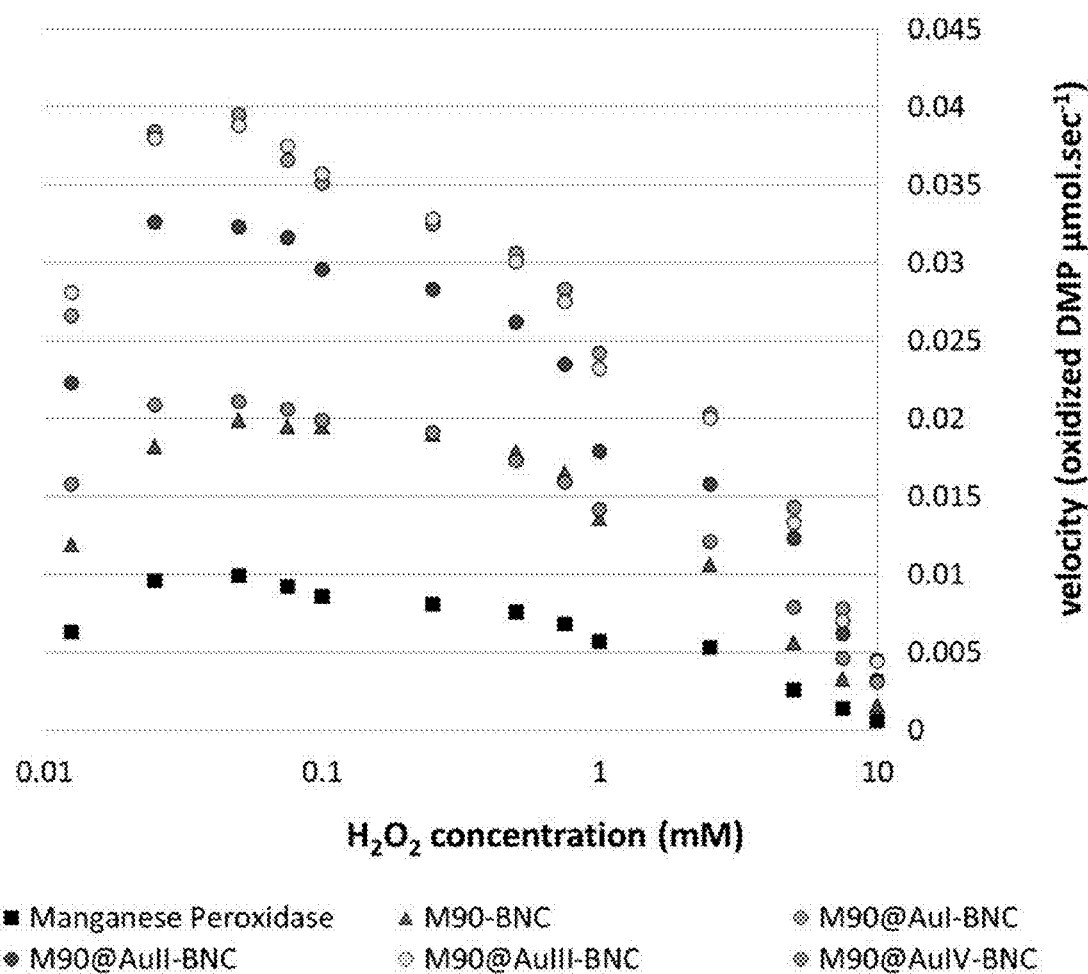
FIG. 22. Velocities plot of BNCs formed with Manganese Peroxidase and gold-coated MNPs compared with M90-MNPs. BNCs were formed with M90 or gold-coated M90 and Manganese Peroxidase (FLPC anion exchange purified form, 5 nM). In this assay, the Manganese Peroxidase produces $Mn^{3+}$ reactive cations, which complex with organic acids and oxidizes dimethoxyphenol (colorimetric reagent). The initial rate of the reaction was doubled in the case of BNCs formed with M90 compared to the free enzyme. The velocity of the reaction was multiplied by a factor of four with gold-coated BNCs compared to the free enzyme.

Activities of Manganese Peroxidase-BNCs: BNCs were formed with manganese peroxidase (FIG. 22). As shown by the velocities plot in FIG. 22, gold-coated MNPs further increase the velocity of the reaction compared to the non-coated magnetite nanoparticles. Differences were observed between the coating conditions (and nanoparticles sizes), resulting in different increases in velocities.

Figure 23:
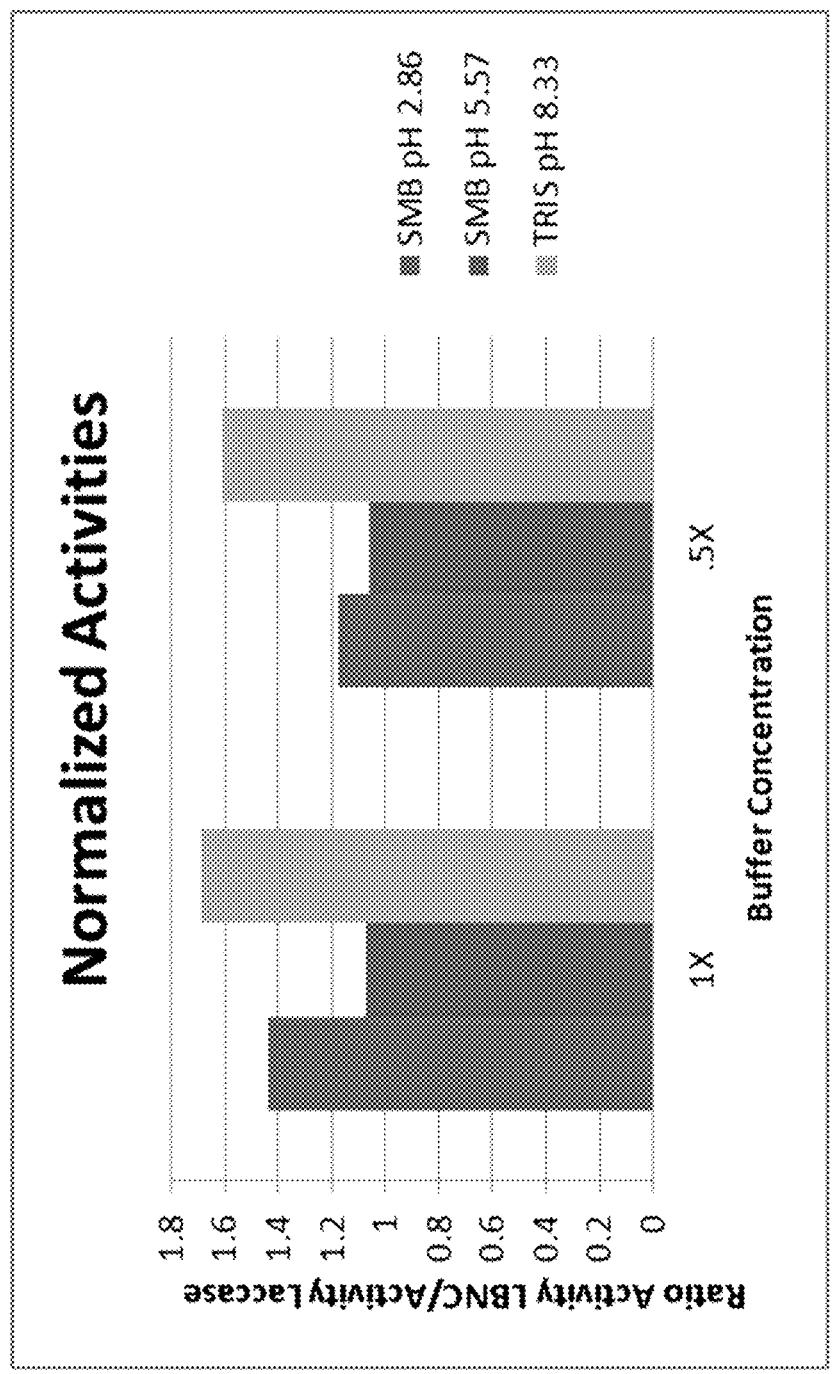
FIG. 23. Graph plotting increased activities of laccase BNCs (Lac-BNCs, normalized activity) as a function of buffer concentration and pH. The assay (phenol/AAP without peroxide) was conducted in different buffers at different pHs. The optimal pH for laccase enzymes is around 5. The increase in activity (up to 60%) was only observed for low and high pH and was higher for high molarity buffers.
Figures 24A, 24B, 24C, 24D:
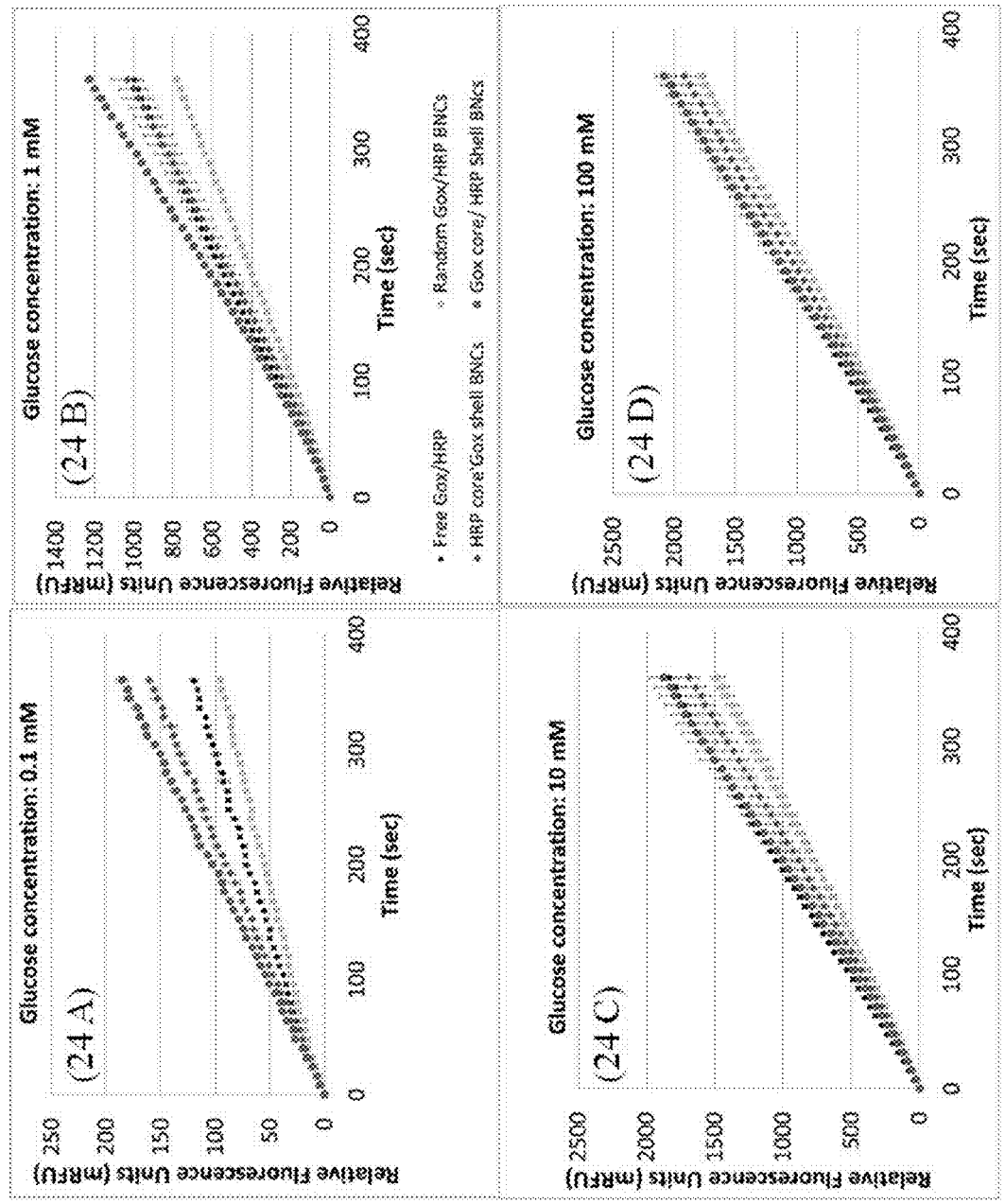
FIGS. 24A-24D. Graph plotting the kinetics of Homovanillic Acid fluorescent dimer formation to determine increased velocities of peroxidase using mixed enzyme BNCs, i.e., clusters with Horseradish Peroxidase (HRP) in the center (core) and Glucose Oxidase (Gox) in the outer layers (shell), clusters with Gox in the center and HRP at the outer layers, or random distribution. The BNCs were formed with gold-coated MNPs and a ratio of Gox to HRP of 1. The HVA assay was used with increasing concentration of glucose. In this system, the Glucose Oxidase converts the glucose to peroxide and gluconolactone and the HRP uses the peroxide to polymerize the homovanillic acid to its fluorescent dimer. The kinetics show that the distribution of the enzymes in the mesoporous space matters.
Figure 25:
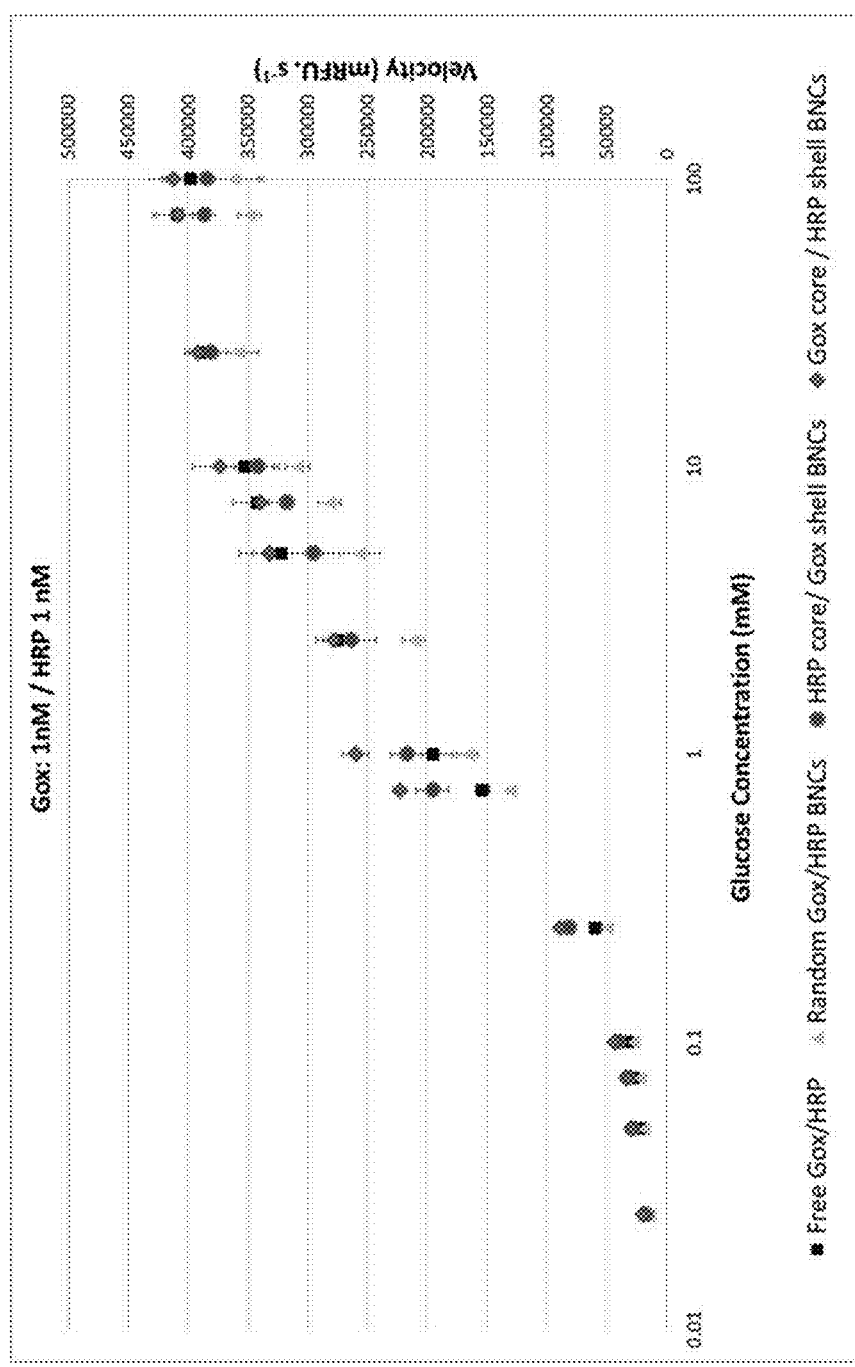
FIG. 25. Velocity plot of a mixed enzyme gold-coated BNC (HVA assay, Glucose Oxidase:HRP in a 1:1 ratio). In this configuration, the velocity (initial rate of the reaction) were higher for the Gox/HRP BNCs in the lower range of glucose compared to the free enzymes. In the higher glucose range, BNCs activity was similar to the one of the free enzyme. No substrate inhibition was observed for this ratio of Gox/HRP and glucose concentration range. The initial rate of the reaction was doubled for the HRP core BNCs compared to the randomly distributed ones. These results demonstrate that the polyenzyme systems can be used, and that the distribution of the enzymes can be controlled to favorably affect the activities of the system.

Activities of Laccase-BNCs: BNCs were formed with laccase (FIG. 23). As shown by the assay plot in FIG. 23, the increase in laccase activity was observed when the enzyme was used in non-optimal condition (low or high pH). The increase, in activity was not as high as the peroxidase enzymes but still significant compared to the free laccases. It is noteworthy that laccases do not require peroxide to function, and therefore, are not subjected to strong substrate inhibition. As previously observed, BNCs provide a strong protection against substrate inhibition and also harsher reaction conditions (e.g., pH, temperature, and ionic strength).

Activities of Glucose Oxidase and Peroxidase system: BNCs were formed with a dual glucose oxidase/peroxidase system (FIGS. 24A-24D and 25). In this configuration, the peroxide is provided by the activities of the glucose oxidase in order to activate the peroxidase. A different configuration was tested using the highly monodispersed gold coated MNPs. As shown by FIGS. 24A-24D and 25, in the ratio of Gox to HRP used, no inhibition of the enzyme system was observed. A core/shell design was implemented for which the HRP is at the core of the clusters and the Gox in the outer layers, and vice versa, or randomly distributed. Core/shell BNCs showed increased activities compared to the free enzymes and the randomly distributed BNCs at lower concentration of glucose. Significantly, this system permits replacing hydrogen peroxide with glucose, and glucose is much less costly, more plentiful, and less hazardous than hydrogen peroxide.

Figures 26A, 26B:
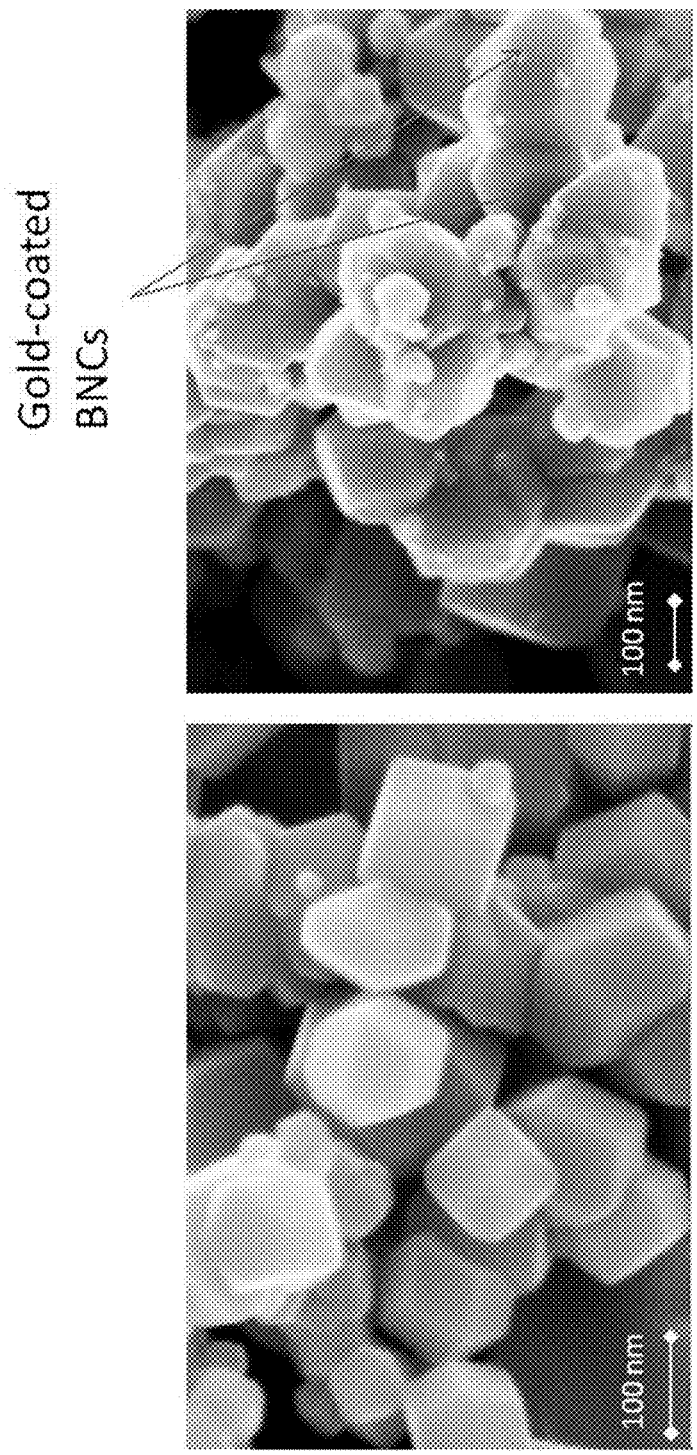
FIGS. 26A, 26B. SEM micrographs of commercial magnetic microparticles (FIG. 26A) and the microparticles surface-functionalized with gold-coated BNCs (Glucose Oxidase and HRP). The preformed BNCs can be immobilized on ferromagnetic microparticles with a remanent magnetization. This new material possesses the advantages of having the enzymes entrapped in the mesoporous space of the magnetic clusters and the additional advantage of having them immobilized on a stable and highly magnetic material.
Figure 27:
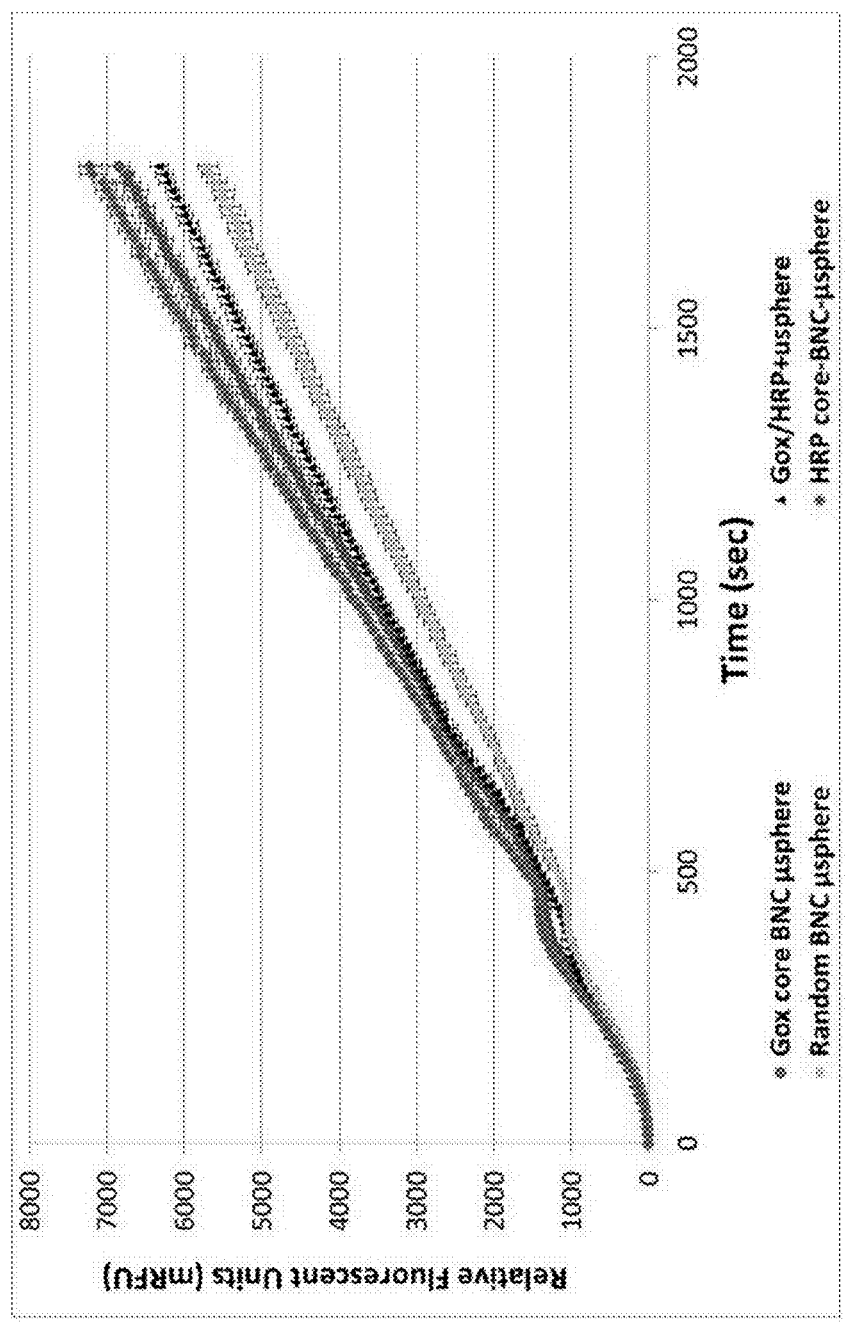
FIG. 27. Graph plotting the kinetics of Homovanillic Acid fluorescent dimer formation produced by Glucose Oxidase/HRP µBNCs. The µBNCs were made using gold-coated Gox/HRP BNCs with clusters with HRP in the center and Gox in the outer layers, clusters with Gox in the center and HRP at the outer layers, or random distribution. The velocity of the core/shell µBNCs was higher than the free enzyme or the randomly distributed BNCs. These results demonstrate that the BNCs can be immobilized on the microparticles and maintain the increase in activity observed for the BNCs alone. Gox:HRP=1:1. Enzyme:MNPs=1:2. MNPs:microsphere=1:100 (W/W).
Figures 28A, 28B, 28C:
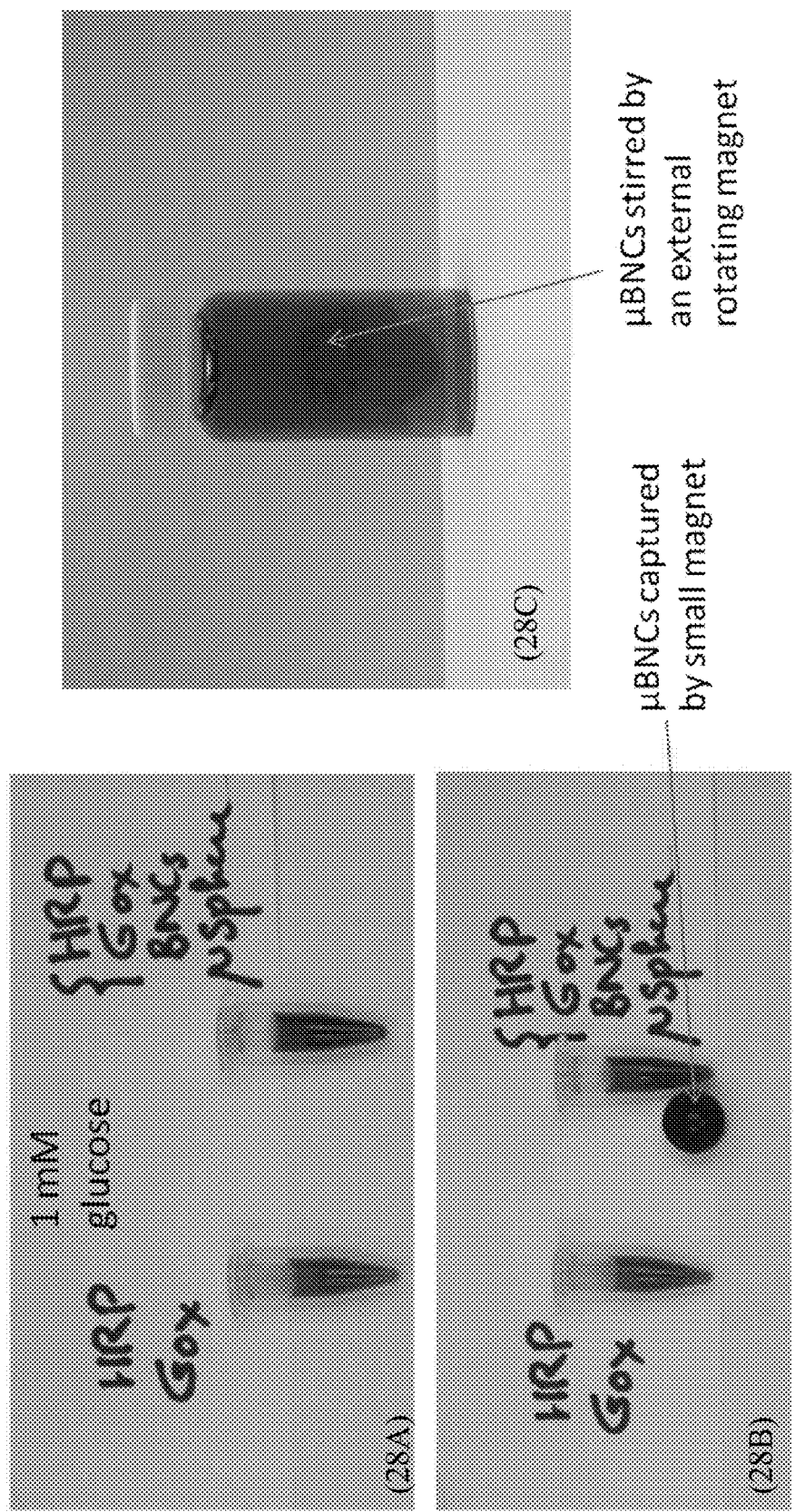
FIGS. 28A-28C. Photographs demonstrating the superior ability of µBNCs to be captured by an external magnet.

These new BNCs were further immobilized on larger ferromagnetic magnetite submicrometric particles. Scanning electron microscope (SEM) micrographs of commercial magnetic particles and their surface functionalization with BNCs are shown in FIGS. 26A and 26B. Although the aggregates of these ferromagnetic particles are micrometric in size, the individual crystallites are submicrometric. The ferromagnetic microparticles readily capture the smaller BNCs that form small clusters on their surface. Although MNPs are fairly magnetic, they require high field magnets to be captured. Also, the smaller and more monodisperse the MNPs, the longer it takes to capture them with an external magnetic field. The BNC-microparticle clusters substantially overcome this limitation. Moreover, as shown by FIGS. 27 and 28A-28C, the enzymatic activities in the BNC-microparticle clusters are similar to the activity of the BNCs (FIG. 27) and can be captured to be re-used or stirred (FIGS. 28A-28C) with very small magnets. This µBNC configuration makes the catalysts process-ready for real-world applications.

Lignin Depolymerization by Magnetite BNCs Formed with Fungal Peroxidases

Figure 29:
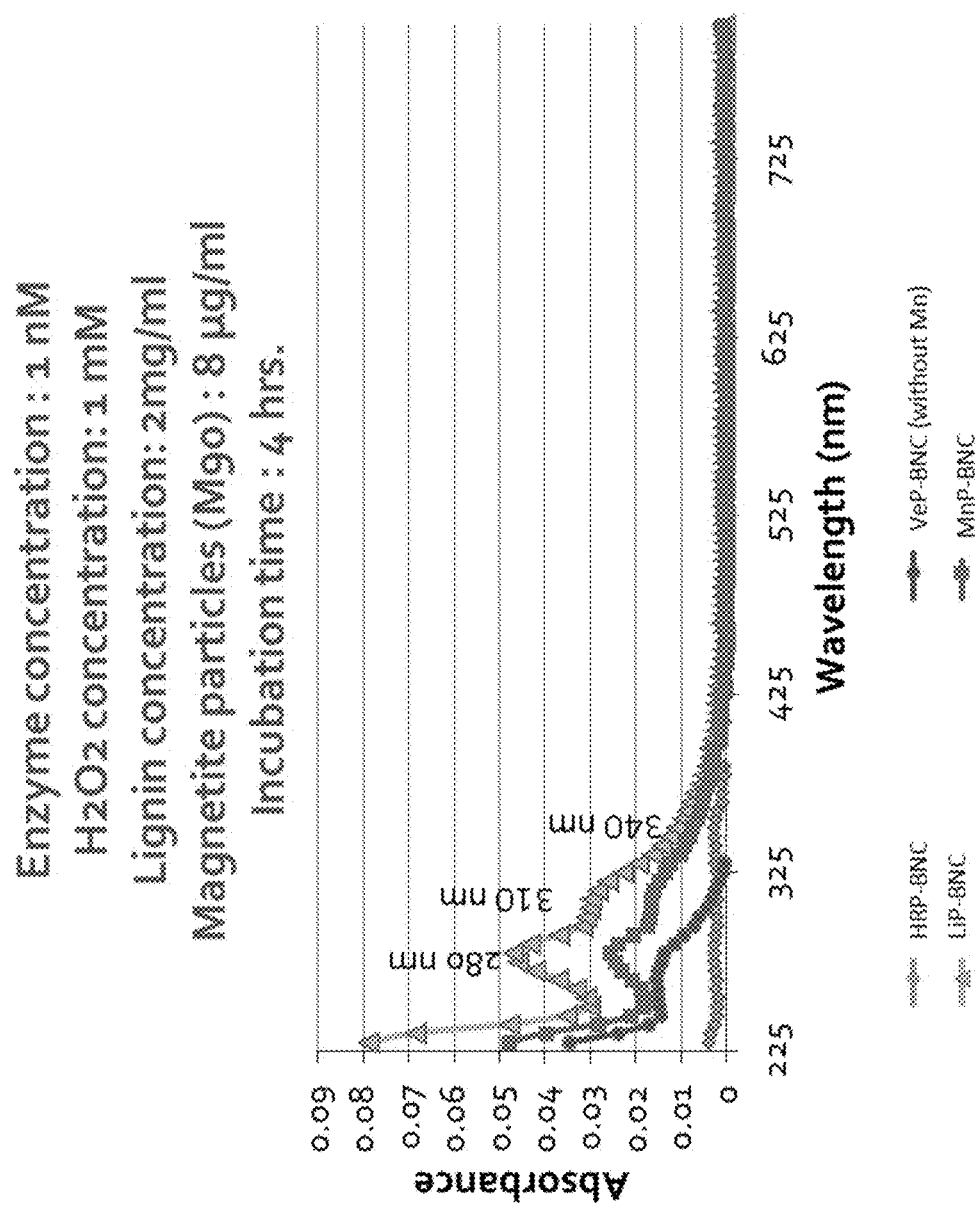
FIG. 29. Wavelength absorbance spectra for HRP-BNC, LiP-BNC, VeP-BNC (without Mn), and MnP-BNC using M90 magnetite nanoparticles. The spectra from the free enzyme at the same concentration were subtracted. The fungal peroxidases entrapped in the mesoporous space of M90-BNCs show higher activities relative their free counterpart (i.e., increased release of aromatics from lignin depolymerization).
Figure 30:
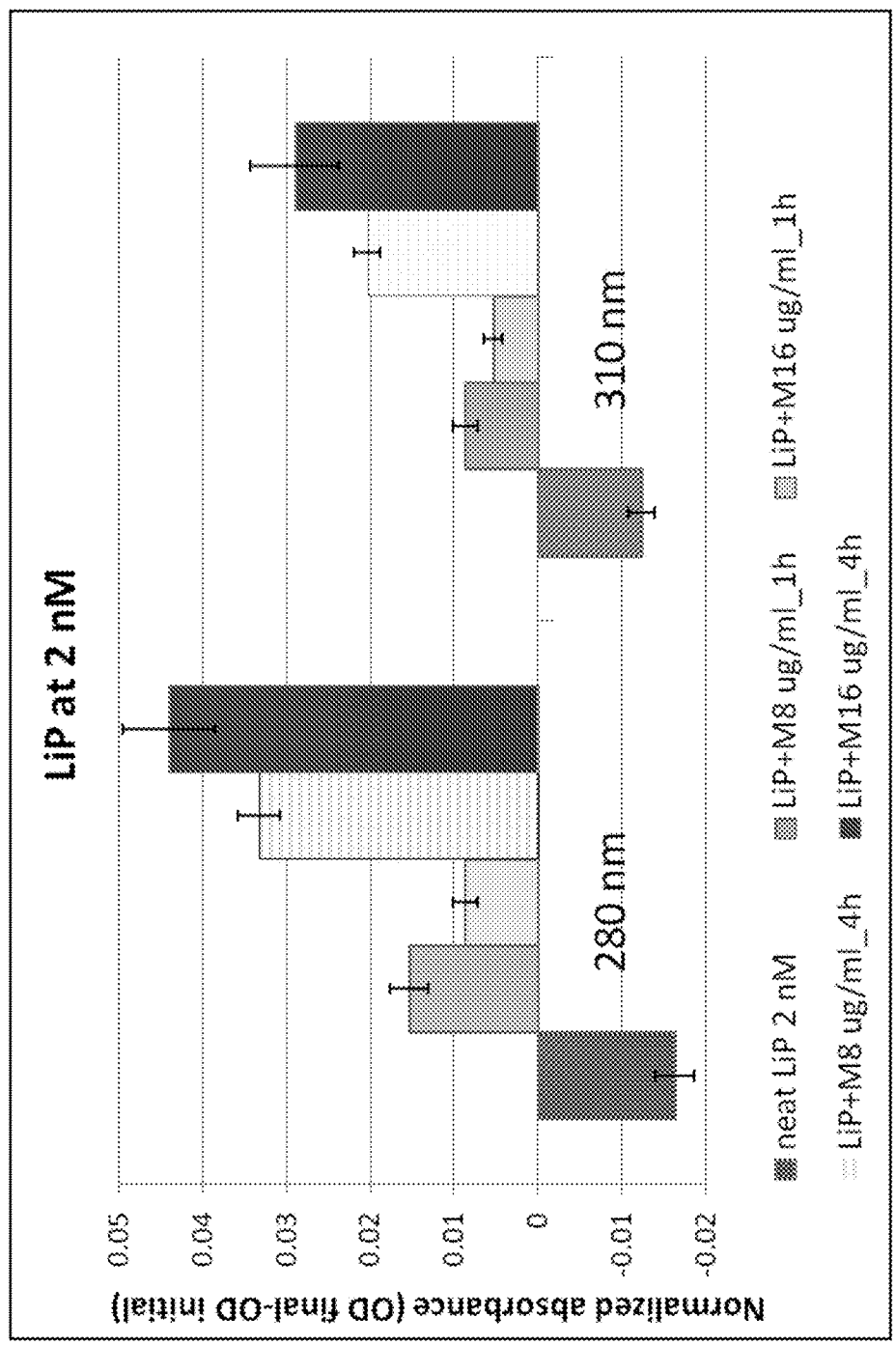
FIG. 30. Chart plotting the increase in soluble aromatic molecules from Kraft lignin with free lignin peroxidase (neat LiP), and LiP+M8 (BNC formed with 2 nM LiP and M90 at 8 μg/ml), and LiP+M16 (BNC formed with 2 nM LiP+M90 at 16 μg/ml). The release of soluble aromatics from Kraft lignin by BNCs was observed at characteristic absorbance wavelengths. BNCs were formed with Lignin Peroxidase at 2 nM enzyme (commercial form, not purified). The OD values for supernatant at T0 (initial condition) and the nanoparticle background were subtracted.
Figure 31:
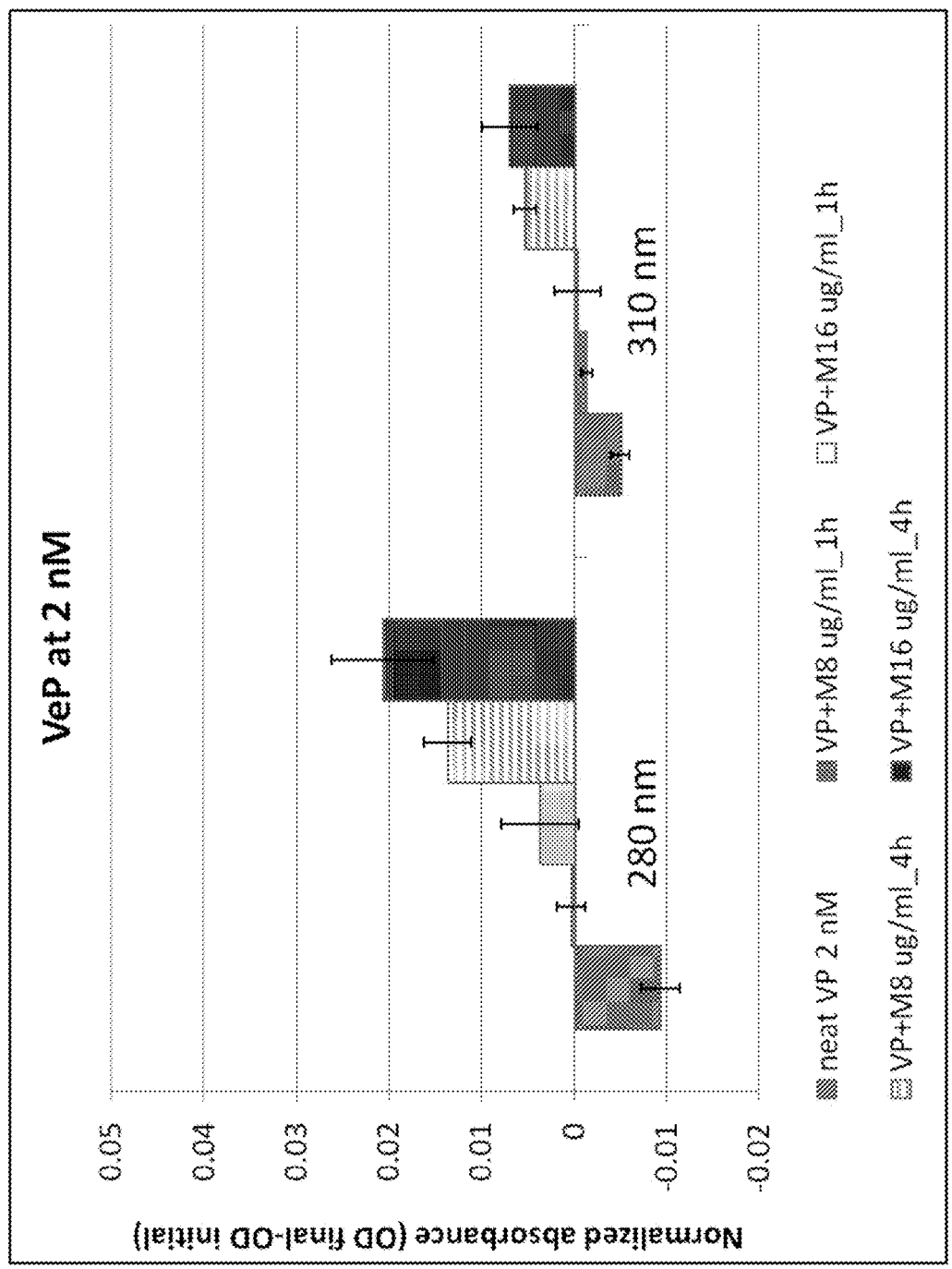
FIG. 31. Chart plotting the increase in soluble aromatic molecules from Kraft lignin with free Versatile Peroxidase (neat VP), VP+M8 (BNC formed with 2 nM VP and M90 at 8 μg/ml), and VP+M16 (BNC formed with 2 nM VP and M90 at 16 μg/ml). The release of soluble aromatics from Kraft lignin by BNCs was observed at characteristic absorbance wavelengths. BNCs were formed with Versatile Peroxidase at 2 nM enzyme (commercial form, not purified). The OD values for supernatant at T0 (initial condition) and the nanoparticle background were subtracted.
Figure 32:
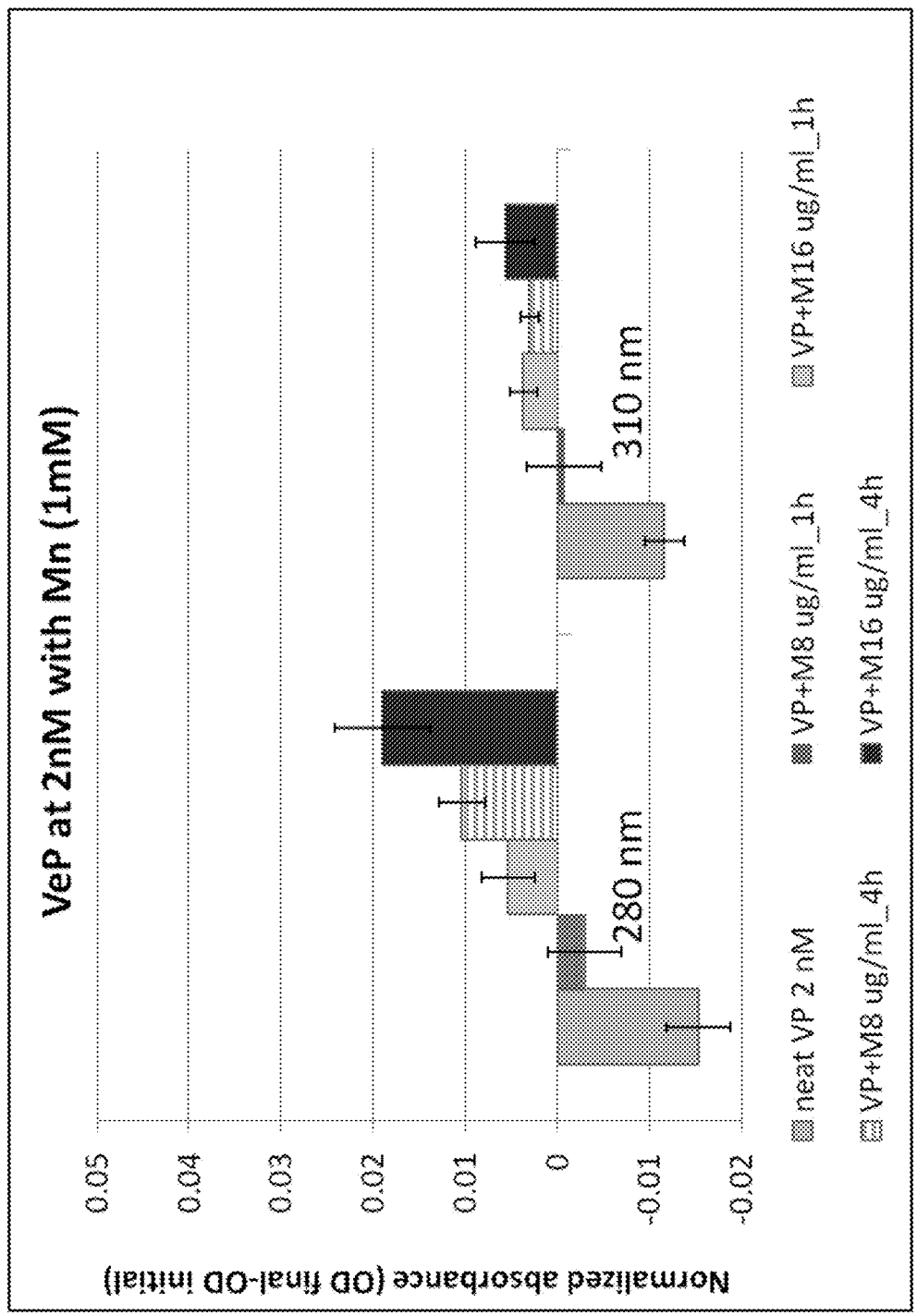
FIG. 32. Chart plotting the increase in soluble aromatic molecule from Kraft lignin with free Versatile Peroxidase (neat VP) in presence of Mn, VP+M8 (BNC formed with 2 nM VP and M90 at 8 μg/ml), and VP+M16 (BNC formed with 2 nM VP and M90 at 16 μg/ml). The release of soluble aromatics from Kraft lignin by BNCs was observed at characteristic absorbance wavelengths. BNCs were formed with Versatile Peroxidase at 2 nM enzyme (commercial form, not purified). The OD values for supernatant at T0 (initial condition) and the nanoparticle background were subtracted.
Figure 33:
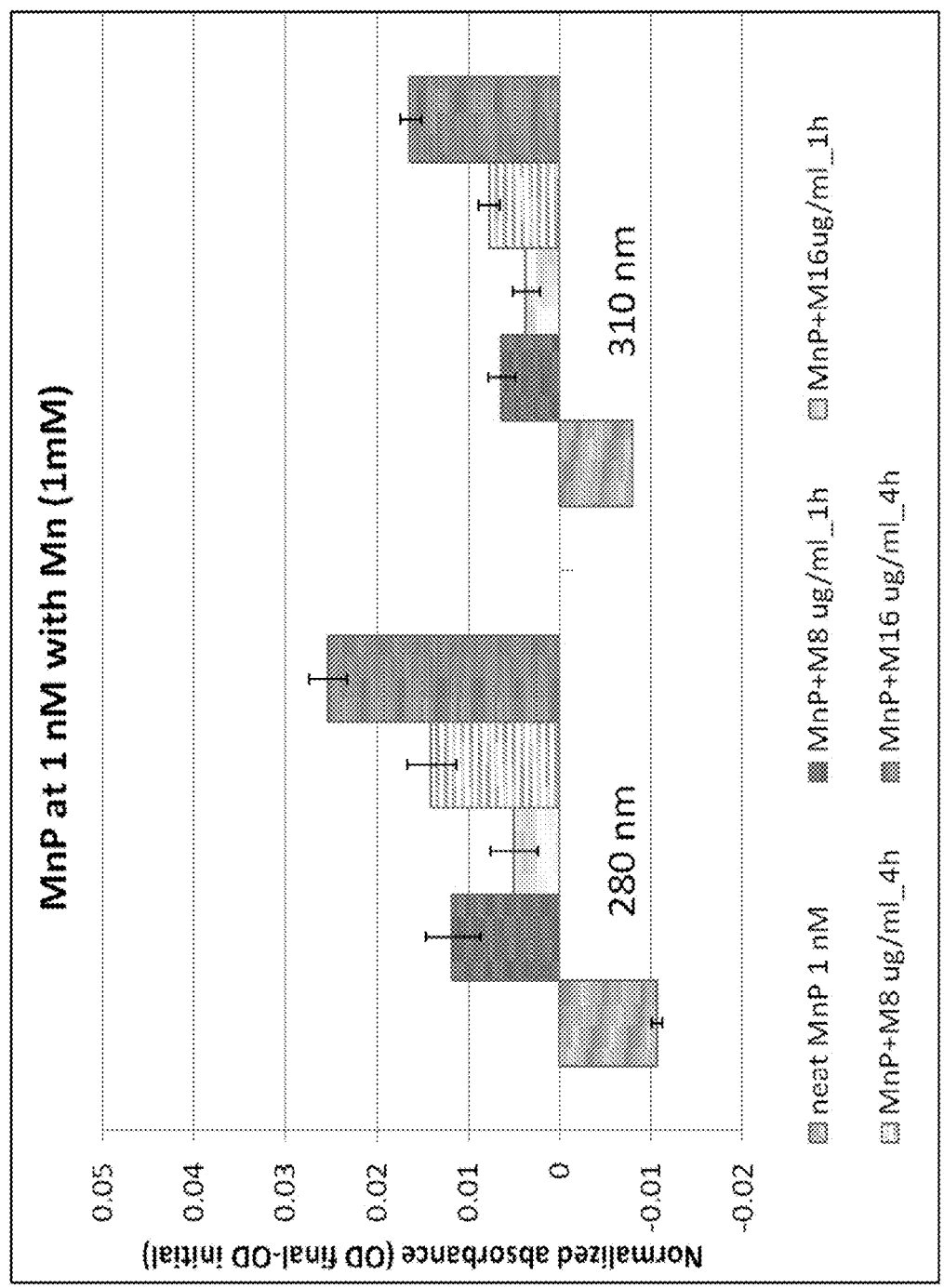
FIG. 33. Chart plotting the increase in soluble aromatic molecules from Kraft lignin with free Manganese Peroxidase (neat MnP), MnP+M8 (BNC formed with 1 nM MnP and M90 at 8 μg/ml), and MnP+M16 (BNC formed with 1 nM and M90 at 16 μg/ml). The release of soluble aromatics from Kraft lignin by BNCs was observed at characteristic absorbance wavelengths. BNCs were formed with Manganese Peroxidase at 1 nM enzyme (commercial form, not purified). The OD values for supernatant at T0 (initial condition) and the nanoparticle background were subtracted.

Lignin depolymerization using BNCs was demonstrated. A lignin depolymerization assay was conducted in order to detect the production of soluble aromatics (e.g., coniferyl, sinapyl, and coumaryl alcohols or derivatives thereof). As shown by the absorbance plot in FIG. 29, increased signals were observed at characteristic wavelengths with the fungal peroxidase system. As also shown by FIG. 29, the BNCs formed with horseradish peroxidase (plant peroxidase) did not release any aromatic molecules from lignin. As shown by FIGS. 30-33, depolymerization of lignin was observed with fungal peroxidase BNCs.

Polymerization of Phenol with BNCs Formed with HRP

Figure 34:
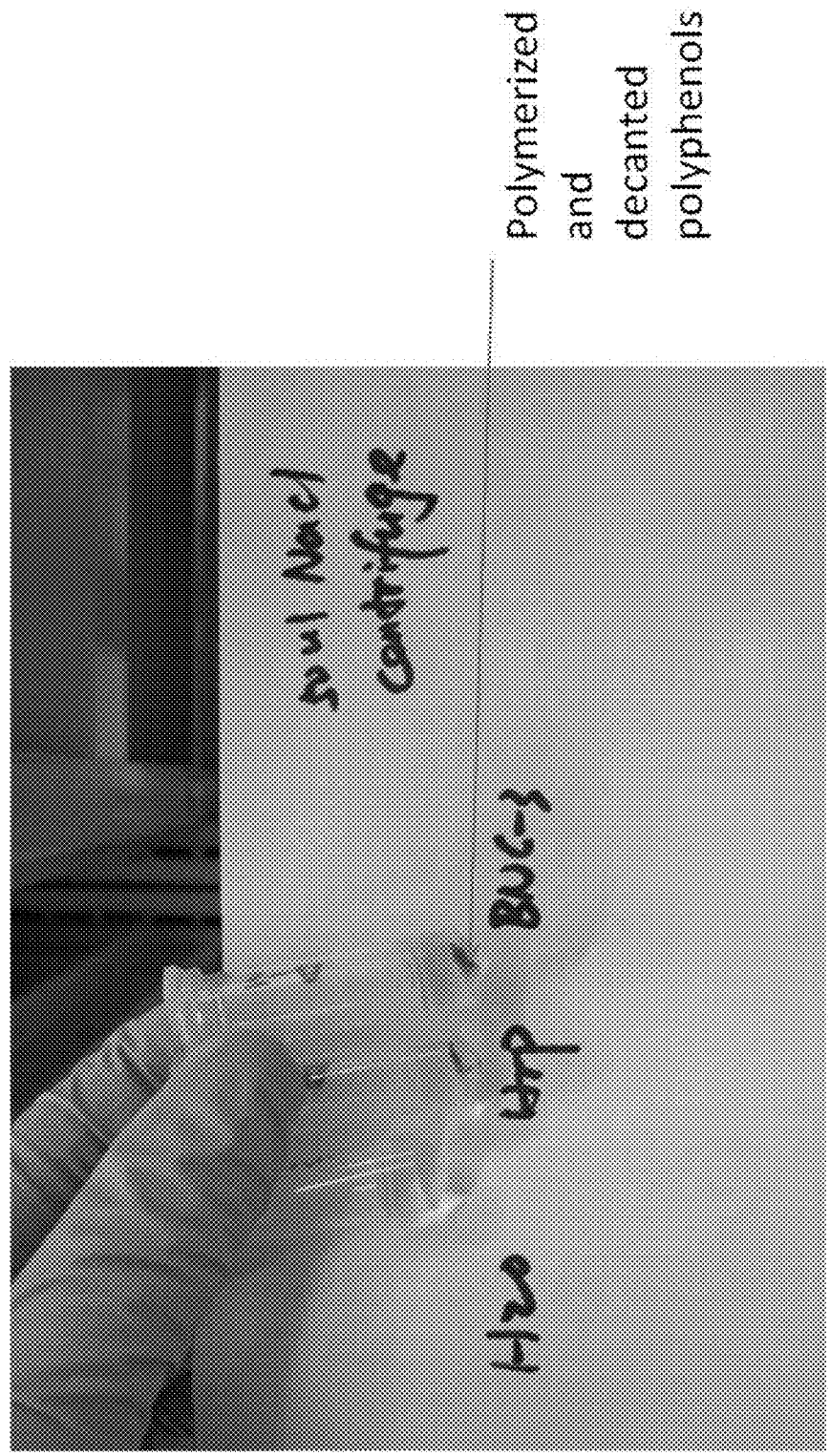
FIG. 34. Photograph demonstrating phenol polymerization and precipitation of polyphenols by HRP and BNCs formed with M90. The condensed polyphenols were precipitated by NaCl and centrifuged, and the remaining phenol in solution was measured by absorbance. The absorbance was corrected for the presence of MNPs.
Figure 35:
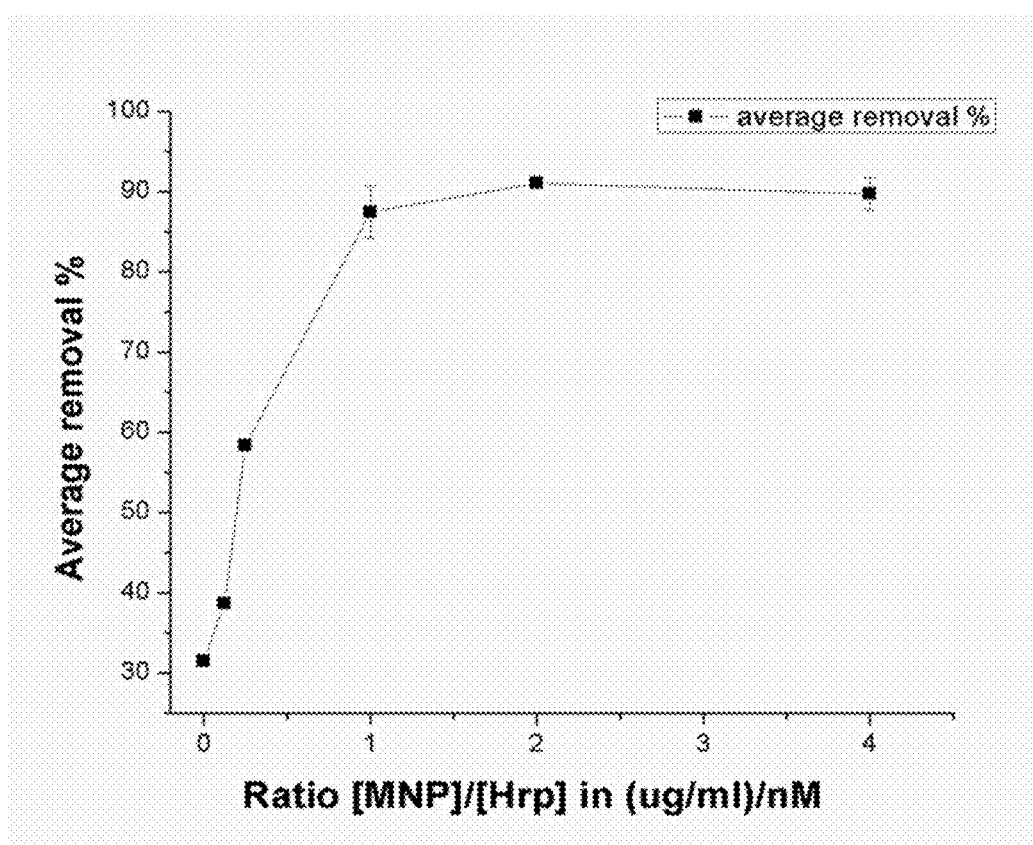
FIG. 35. Graph plotting average phenol removal (%) as a function of MnP/HRP ratio to determine effect of nanoparticle to enzyme ratio on the percentage of phenol removal. The total enzyme (horseradish peroxidase) quantity and peroxide and phenol concentrations (1 mM each) were fixed. The proportion of MNPs was increased to form the BNCs. The quantity of phenol removed from solution increased when the enzyme was entrapped in the mesoporous space of the magnetic clusters of M90. The efficiency of phenol removal was close to 95%.
Figure 36:
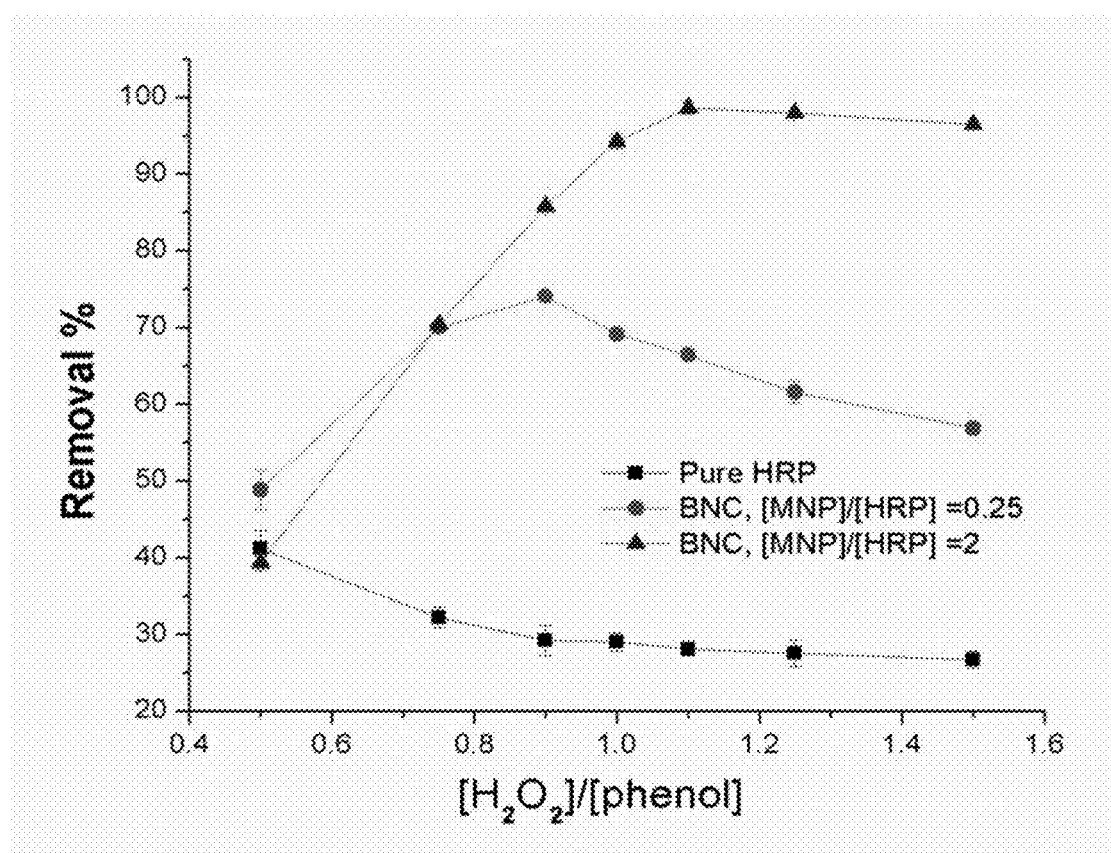
FIG. 36. Graph plotting % phenol removal as a function of the ratio of peroxide to phenol to determine the effect of hydrogen peroxide to phenol ratio on phenol removal by HRP and BNCs thereof. The phenol final concentration was fixed to 1 mM. The quantity of peroxide was varied. The efficiency of phenol removal increased up to 100% for a peroxide/phenol ratio of 1.1, for which the efficiency of the free enzyme was only around 30%. The efficiency of the free enzyme decreased when the peroxide concentration increased due to substrate inhibition. On the contrary, the BNCs showed little or no inhibition in the range tested depending on the MNP/HRP ratio.

Phenol removal using Horseradish Peroxidase using BNCs was demonstrated. As pictographically shown in FIG. 34, phenol polymerization assays were conducted using a two-step process: (i) enzymatic polymerization to polyphenols, and (ii) condensation of the polyphenol polymers by sodium chloride. As shown by the activity plot in FIG. 35, the BNCs formed with HRP and M90 MNPs were more efficient at removing the phenol than the free enzyme. The foregoing result demonstrates a marked improvement in phenol removal when using BNCs rather than a free HRP system. As shown in FIG. 36, besides the increased extent of phenol removal, there is a $H_2O_2$ concentration shift to reach the maximum removal (or polymerization) in the BNC system. This indicates that BNCs have a lower inhibition from $H_2O_2$ compared to the free enzyme. Moreover, the BNC system offers a broader $H_2O_2$ concentration range. These features demonstrate that BNCs can be used in unstable and harsher process conditions than their free counterpart.

While there have been shown and described what are at present considered the preferred embodiments of the invention, those skilled in the art may make various changes and modifications which remain within the scope of the invention defined by the appended claims.

What is claimed is:

1. A composition comprising self-assembled mesoporous aggregates of magnetic nanoparticles and a first free-radical producing enzyme, wherein said first enzyme is magnetically-entrapped without a bonding agent in mesopores formed by said aggregates of magnetic nanoparticles and said first enzyme functions by converting a diffusible substrate into a diffusible product.

2. The composition of claim 1, wherein said mesoporous aggregates of magnetic nanoparticles have an iron oxide composition.

3. The composition of claim 1, wherein said mesoporous aggregates of magnetic nanoparticles have a magnetic nanoparticle size distribution in which at least 90% of magnetic nanoparticles have a size of at least 3 nm and up to 30 nm, and an aggregated particle size distribution in which at least 90% of said mesoporous aggregates of magnetic nanoparticles have a size of at least 10 nm and up to 500 nm.

4. The composition of claim 1, wherein said mesoporous aggregates of magnetic nanoparticles possess a saturated magnetization of at least 10 emu/g.

5. The composition of claim 1, wherein said mesoporous aggregates of magnetic nanoparticles possess a remanent magnetization up to 5 emu/g.

6. The composition of claim 1, wherein said free-radical-producing enzyme is contained in said mesoporous aggregates of magnetic nanoparticles in up to 100% of saturation capacity.

7. The composition of claim 1, wherein said first free-radical-producing enzyme is an EC 1.11 oxidoreductase.

8. The composition of claim 7, wherein said free-radical-producing enzyme is comprised of a peroxidase.

9. The composition of claim 8, wherein said peroxidase is a class III peroxidase.

10. The composition of claim 9, wherein said class III peroxidase is horseradish peroxidase.

11. The composition of claim 1, wherein said mesopores are characterized by a pore size distribution in which at least 90% of the pore volume is attributed to pores having a pore size of at least 2 nm and up to 20 nm.

12. The composition of claim 1, further comprising a second enzyme that is an EC 1.1.3 enzyme, and wherein said first enzyme is a peroxidase.

13. The composition of claim 12, wherein said EC 1.1.3 enzyme is glucose oxidase EC 1.1.3.4.

14. The composition of claim 12, wherein said peroxidase is horseradish peroxidase.

15. The composition of claim 1, wherein said mesoporous aggregates of magnetic nanoparticles and free-radical producing enzyme further comprise a metallic surface layer.

16. Microparticles comprising the composition of claim 1.

17. The microparticles of claim 16, wherein said microparticles comprise magnetite.

18. The microparticles of claim 16, wherein said microparticles are ferromagnetic submicrometric particles having a size of at least 20 nanometers.

19. The composition of claim 1, wherein said mesoporous aggregates of magnetic nanoparticles have a magnetic nanoparticle size distribution in which at least 50% of magnetic nanoparticles have a size of at least 1 nm and up to 50 nm, and an aggregated particle size distribution in which at least 90% of said mesoporous aggregates of magnetic nanoparticles have a size of at least 10 nm and up to 500 nm, and wherein said free-radical producing enzyme is an oxidoreductase belonging to the EC1 family of enzymes.

* * * * *